United States Patent
Bischof et al.

(10) Patent No.: US 11,358,914 B2
(45) Date of Patent: Jun. 14, 2022

(54) ETHYLENE OLIGOMERIZATION PROCESSES

(71) Applicant: Chevron Phillips Chemical Company LP, The Woodlands, TX (US)

(72) Inventors: Steven M. Bischof, Humble, TX (US); Brooke L. Small, Kingwood, TX (US)

(73) Assignee: Chevron Phillips Chemical Company, LP, The Woodlands, TX (US)

( * ) Notice: Subject to any disclaimer, the term of this patent is extended or adjusted under 35 U.S.C. 154(b) by 0 days.

(21) Appl. No.: 17/213,638

(22) Filed: Mar. 26, 2021

(65) Prior Publication Data
US 2021/0214289 A1 Jul. 15, 2021

Related U.S. Application Data

(63) Continuation of application No. 15/394,411, filed on Dec. 29, 2016, now abandoned.

(51) Int. Cl.
*C07C 2/32* (2006.01)

(52) U.S. Cl.
CPC ............ *C07C 2/32* (2013.01); *C07C 2531/14* (2013.01); *C07C 2531/22* (2013.01); *Y02P 20/52* (2015.11)

(58) Field of Classification Search
CPC ....... C07C 2/32; C07C 11/02; C07C 2531/14; C07C 2531/22; C07C 2531/30; B01J 2231/20; B01J 2531/0244; B01J 2531/842; B01J 2531/845; B01J 31/1815
See application file for complete search history.

(56) References Cited

U.S. PATENT DOCUMENTS

| | | | |
|---|---|---|---|
| 5,451,645 | A | 9/1995 | Reagen |
| 5,955,555 | A | 9/1999 | Bennett |
| 6,103,946 | A | 8/2000 | Brookhart, III |
| 6,214,761 | B1 | 4/2001 | Bennett |

(Continued)

FOREIGN PATENT DOCUMENTS

| | | |
|---|---|---|
| CA | 2020509 C | 4/1998 |
| CN | 104418690 B | 5/2016 |

(Continued)

OTHER PUBLICATIONS

"Group notation revised in periodic table," Feb. 4, 1985, C&EN, p. 27.

(Continued)

*Primary Examiner* — Sharon Pregler
(74) *Attorney, Agent, or Firm* — Conley Rose, P.C.

(57) ABSTRACT

A process comprising A) continuously introducing into a reaction zone i) ethylene, ii) an iron salt, iii) a pyridine bisimine, iv) an organoaluminum compound, and v) an organic reaction medium, and B) forming an oligomer product in the reaction zone, the reaction zone having i) an iron of the iron salt concentration in a range of $5 \times 10^{-4}$ mmol/kg to $5 \times 10^{-3}$ mmol/kg, ii) an aluminum of the organoaluminum compound to iron of the iron salt molar ratio in a range of 300:1 to 800:1, ii) an ethylene partial pressure in a range of 750 psig to 1200 psig, iv) an ethylene to organic reaction medium mass ratio in a range of 0.8 to 4.5, v) a temperature in a range of 75° C. to 95° C., and optionally vi) a hydrogen partial pressure of at least 5 psi.

23 Claims, 1 Drawing Sheet

(56) References Cited

U.S. PATENT DOCUMENTS

| | | |
|---|---|---|
| 6,291,733 B1 | 9/2001 | Small |
| 6,417,305 B2 | 7/2002 | Bennett |
| 6,423,848 B2 | 7/2002 | Bennett |
| 6,432,862 B1 | 8/2002 | Bennett |
| 6,451,939 B1 | 9/2002 | Britovsek |
| 6,455,660 B1 | 9/2002 | Clutton |
| 6,458,739 B1 | 10/2002 | Kimberley |
| 6,458,905 B1 | 10/2002 | Schmidt |
| 6,461,994 B1 | 10/2002 | Gibson |
| 6,472,341 B1 | 10/2002 | Kimberley |
| 6,489,497 B1 | 12/2002 | Brookhart, III |
| 6,534,691 B2 | 3/2003 | Culver |
| 6,545,108 B1 | 4/2003 | Moody |
| 6,555,723 B2 | 4/2003 | Schiffino |
| 6,559,091 B1 | 5/2003 | Moody |
| 6,657,026 B1 | 12/2003 | Kimberley |
| 6,683,187 B2 | 1/2004 | De Boer |
| 6,710,006 B2 | 3/2004 | De Boer |
| 6,740,715 B2 | 5/2004 | Brookhart, III |
| 6,911,505 B2 | 6/2005 | Small |
| 6,911,506 B2 | 6/2005 | Small |
| 7,001,964 B2 | 2/2006 | Small |
| 7,037,988 B2 | 5/2006 | De Boer |
| 7,045,632 B2 | 5/2006 | Small |
| 7,049,442 B2 | 5/2006 | De Boer |
| 7,053,020 B2 | 5/2006 | De Boer |
| 7,053,259 B2 | 5/2006 | Culver |
| 7,056,997 B2 | 6/2006 | Small |
| 7,129,304 B1 | 10/2006 | Small |
| 7,223,893 B2 | 5/2007 | Small |
| 7,268,096 B2 | 9/2007 | Small |
| 7,271,121 B2 | 9/2007 | Small |
| 7,297,806 B2 | 11/2007 | Brookhart, III |
| 7,304,159 B2 | 12/2007 | De Boer |
| 7,442,819 B2 | 10/2008 | Ionkin |
| 7,456,284 B2 | 11/2008 | Small |
| 7,683,149 B2 | 3/2010 | Ionkin |
| 7,902,415 B2 | 3/2011 | Small |
| 7,994,376 B2 | 8/2011 | Small |
| 9,586,872 B2 | 3/2017 | Small |
| 2002/0016425 A1 | 2/2002 | De Boer |
| 2004/0026795 A1 | 2/2004 | Kulinsky |
| 2005/0014983 A1 | 1/2005 | De Boer |
| 2005/0187418 A1 | 8/2005 | Small |
| 2007/0112150 A1 | 5/2007 | Small |
| 2007/0221608 A1 | 9/2007 | Axe |
| 2010/0274065 A1 | 10/2010 | Sydora |
| 2013/0172651 A1* | 7/2013 | Small ............... B01J 31/1815 585/523 |
| 2013/0211168 A1 | 8/2013 | Breuil |
| 2016/0229766 A1 | 8/2016 | Sydora |

FOREIGN PATENT DOCUMENTS

| | | |
|---|---|---|
| CN | 105884565 A | 8/2016 |
| EP | 1229020 B1 | 1/2011 |
| WO | 2004026795 A2 | 4/2004 |
| WO | 2005005354 A1 | 1/2005 |
| WO | 2010051415 A1 | 5/2010 |
| WO | 2011126787 A1 | 10/2011 |
| WO | 2013101387 A1 | 7/2013 |

OTHER PUBLICATIONS

Agapie, T., "Selective Ethylene Oligomerization: Recent advances in chromium catalysis and mechanistic Investigations," Coordination Chemistry Reviews, 2011, vol. 255, pp. 861-880, Elsevier B.V.
Bennett, A. et al., "Novel, highly active iron and cobalt catalysts for olefin polymerization," CHEMTECH, Jul. 1999, pp. 24-28, vol. 29, American Chemical Society.
Boudier, et al. "Novel Catalytic System for Ethylene Oligomerization: An Iron(III) Complex with an Anionic N,N,N Ligand." Organometallics, 2011, vol. 30, pp. 2640-2642. American Chemical Society.
Britovsek, G. et al., "Iron and Cobalt Ethylene Polymerization Catalysts bearing 2,6-Bis(imino)Pyridyl Ligands: Synthesis, Structures and Polymerization Studies," Journal of the American Chemical Society, 1999, pp. 8728-8740, vol. 121, American Chemical Society.
Britovsek, G. et al., "Novel olefin polymerization catalysts based on iron and cobalt," Chemical Communication, 1998, pp. 849-850, vol. 7.
Britovsek, G. et al., "Oligomerization of Ethylene by Bis(imino)pyridyliron and -cobalt Complexes," Chemistry—A European Journal, 2000, pp. 2221-2231, vol. 6, No. 12, Wiley-VCH.
Chen, Y., et al., "Fluoro-Substituted 2,6-Bis(imino)pyridyl Iron and Cobalt Complexes: High-Activity Ethylene Oligomerization Catalysts," Organometallics, 2003, pp. 1231-1236, vol. 32, American Chemical Society.
Chen, Y., et al., Halogen-Substituted 2,6-Bis{imino)pyridyl Iron and cobalt Complexes: Highly Active Catalysts for Polymerization and Oligomerization of Ethylene, Organometallics, 2003, pp. 4312-4321, vol. 22, American Chemical Society.
Dixon, J., et al., "Advances in selective ethylene trimerisation—a critical overview," Journal of Organometallic Chemistry, 2004, vol. 689, pp. 3641-3668, Elsevier B. V.
International Search Report and Written Opinion for PCT/US2017/068274. dated Jun. 7, 2018. 23 pages.
International Search Report and Written Opinion for PCT/US2017/068281. dated Apr. 9, 2018. 13 pages.
International Search Report and Written Opinion for PCT/US2017/268278. dated May 30, 2018. 18 Pages.
Ionkin, A., et al., "High-Temperature Catalysts for the Production of a-Olefins Based on Iron{II} and Cobalt{II}-ridentate Bis{imino}pyridine Complexes with a Double Pattern of Substitution: o-Methyl plus o-Fluorine in the Same Imine Arm," Organometallics, 2008, pp. 1147-1156, vol. 27, American Chemical Society.
Ionkin, A., et al., "High-Temperature Catalysts for the Production of a-Olefins Based on Iron{II} and Iron{III} Tridentate Bis{imino)pyridine Complexes with Double Pattern of Substitution: ortho-Methyl plus meta-Aryl," Organometallics, 2006, pp. 2987-2992, vol. 25, American Chemical Society.
Ionkin, A., et al., "High-Temperature Catalysts for the Production of a-Olefins Based on Iron{II} and Iron{III} Tridentate Bis{imino)pyridine Complexes Modified by Nitrilo Group," J_Poly. Sci.: Part A Poly. Chem., 2008, pp. 585-611, vol. 46.
Ionkin, A., et al., "Modification of Iron{II} Tridentate Bis{imino)pyridine Complexes by a Boryl Group for the Production of a-Olefins at High Temperature," Organometallics, 2008, pp. 1902-1911, vol. 27, American Chemical Society.
Manyik, R., et al., "A Soluble Chromium-based Catalyst for Ethylene Trimerization and Polymerization," Journal of Catalysis, 1977, vol. 47, pp. 197-209, Academic Press, Inc.
McNaught, Alan D., et al., "Compendium of Chemical Terminology," IUPAC Recommendations, Second edition, 1997, 5 pages, Wiley-Blackwell.
Schmiege, B., et al., "Alternatives to pyridinediimine ligands: syntheses and structures of metal complexes supported by donor-modified a-diimine ligands," Dalton Transactions, 2007, vol. 24, pp. 2547-2562, Royal Society of Chemistry.
Small, B. et al., "Highly Active Iron and Cobalt Catalysts for the Polymerization of Ethylene," Journal of the American Chemical Society, 1998, pp. 4049-4050, vol. 120, American Chemical Society.
Small, B. et al., "Iron-Based Catalysts with Exceptionally High Activities and Selectivities for Oligomerization of Ethylene to Linear a-Olefins," Journal of the American Chemical Society, 1998, pp. 7143-7144, vol. 120, American Chemical Society.
Small, B. et al., "Polymerization of Propylene by a New Generation of Iron Catalysts: Mechanisms of Chain Initiation, Propagation, and Termination," Macromolecules, Oct. 29, 1999, pp. 2120-2130, vol. 32, American Chemical Society.

(56) References Cited

OTHER PUBLICATIONS

Small, B., et al., "Oligomerization of Ethylene using New Iron Catalysts Bearing Pendant Donor Modified a-Diimine Ligands," Organometallics, 2007, vol. 26, pp. 1744-1749, American Chemical Society.

Small, B., et al., "Oligomerization of Ethylene Using New Tridentate Iron Catalysts Bearing a-Diimine Ligands with Pendant S and P Donors," Organometallics, 2010, vol. 29, pp. 6723-6731, American Chemical Society.

Sun, et al. "Iron Complexes Bearing 2-lmino-10,10-phenanthrolinyl Ligands as Highly Active Catalysts for Ethylene Oligormerization." Organometallics, 2006, vol. 25, pp. 666-677. American Chemical Society.

Walsh, R., et al. "Tetramerisation Process Technology Review." The IP.com Prior Art Database. Jul. 13, 2004. Sasol Technology (Pty) Ltd. 28 pages.

Zhang, Z., et al., "Ethylene oligomerization catalyzed by a novel iron complex containing fluoro and methyl substituents," Journal of Molecular catalysis A: Chemical, 2004, pp. 249-254, vol. 219, Elsevier B.V.

\* cited by examiner

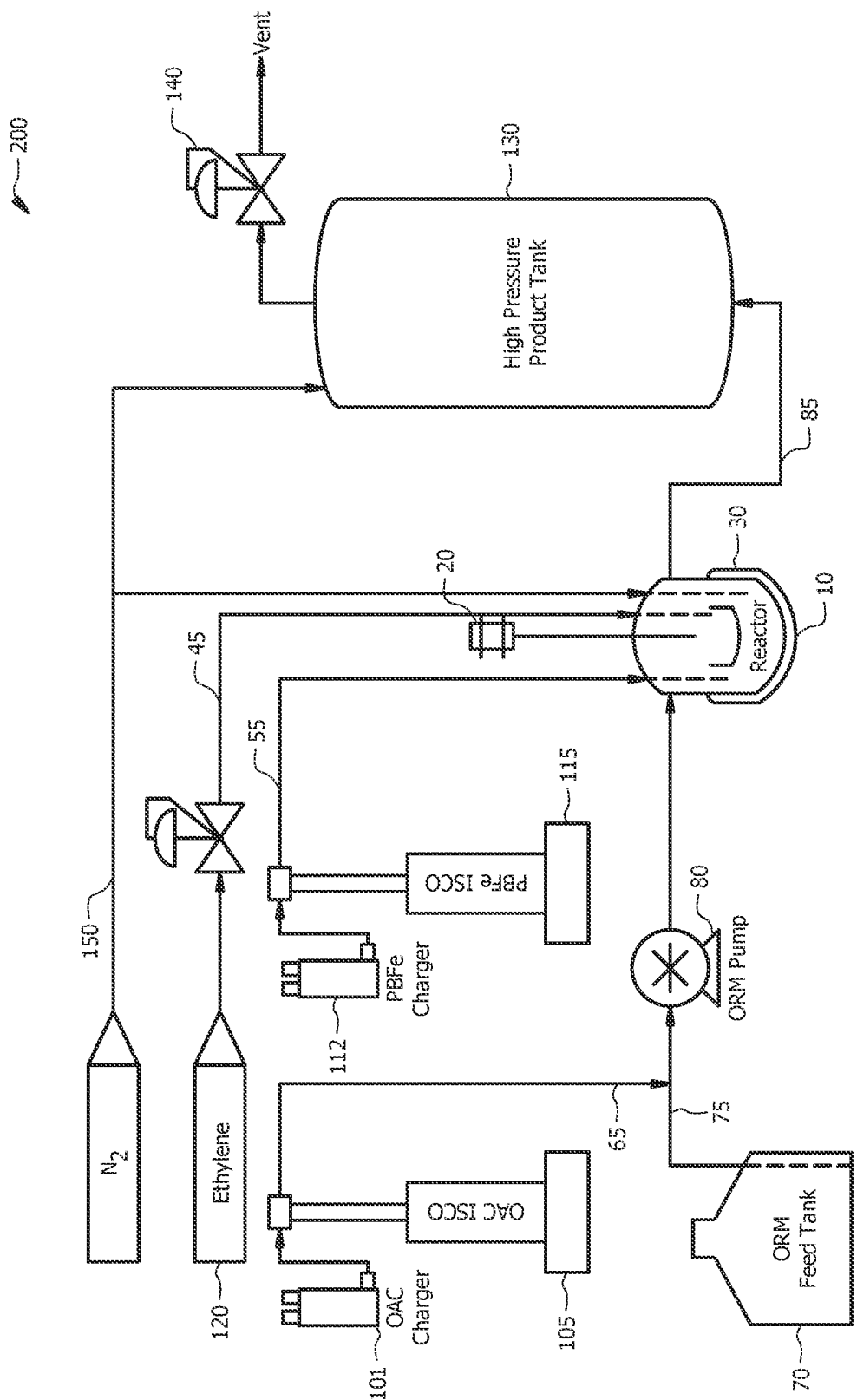

ETHYLENE OLIGOMERIZATION PROCESSES

CROSS-REFERENCE TO RELATED APPLICATIONS

This application is a continuation of and claims priority to U.S. patent application Ser. No. 15/394,411 filed Dec. 29, 2016, published as U.S. Patent Application No. US 2018/0186708 A1, and entitled "Ethylene Oligomerization Processes," which is incorporated by reference herein in its entirety.

FIELD

The present disclosure relates to processes for producing alpha olefins. More particularly, the present disclosure relates to improved processes for oligomerizing ethylene.

BACKGROUND

Alpha olefins are important items of commerce. Their many applications include employment as intermediates in the manufacture of detergents, as precursors to more environmentally friendly refined oils, as monomers, and as precursors for many other types of products. One method of making alpha olefins is via oligomerization of ethylene in a catalytic reaction involving various types of catalysts and/or catalyst systems. Examples of catalysts and catalyst systems used commercially to produce alpha olefins include alkylaluminum compounds, certain nickel-phosphine complexes, titanium halides with a Lewis acid (e.g., diethyl aluminum chloride), zirconium halides and/or zirconium alkoxides with alkylaluminum compounds. Additionally, there is a selective ethylene trimerization and/or tetramerization catalyst system for producing 1-hexene that uses a chromium containing compound (e.g., a chromium carboxylate), a nitrogen-containing ligand (e.g., a pyrrole), and a metal alkyl (e.g., alkyl aluminum compounds).

Several non-commercial oligomerization catalyst systems to produce alpha olefins are based upon metal complexes of pyridine bisimines, metal complexes of α-diimine compounds having a metal complexing group, and selective trimerization and/or tetramerization catalyst systems using a metal compound (e.g., a chromium compound) complex of a diphosphinylamine, phosphinyl formamidine, phosphinyl amidine, or phosphinyl guanidine. These catalyst systems typically use an organoaluminum compound (e.g., aluminoxane) as a component of the catalyst systems for olefin oligomerization.

Applications and demand for olefins (e.g., alpha olefins) continue to multiply, and competition to supply them correspondingly intensifies. Thus, additional novel and improved catalyst systems and processes for olefin oligomerization are desirable.

SUMMARY

Disclosed herein is a process comprising A) continuously introducing into a reaction zone i) ethylene, ii) an iron salt, iii) a pyridine bisimine, iv) an organoaluminum compound, and v) an organic reaction medium, and B) forming an oligomer product in the reaction zone, the reaction zone having i) an iron of the iron salt concentration in a range of $5\times10^{-4}$ mmol/kg to $5\times10^{-3}$ mmol/kg, ii) an aluminum of the organoaluminum compound to iron of the iron salt molar ratio in a range of 300:1 to 800:1, iii) an ethylene partial pressure in a range of 750 psig to 1200 psig, iv) an ethylene to organic reaction medium mass ratio in a range of 0.8 to 4.5, v) a temperature in a range of 75° C. to 95° C., and optionally vi) a hydrogen partial pressure of at least 5 psi.

Also disclosed herein is a process comprising A) continuously introducing into a reaction zone i) ethylene, ii) an pyridine bisimine iron salt complex, iii) an organoaluminum compound, and iv) an organic reaction medium; and B) forming an oligomer product in the reaction zone, the reaction zone having i) an iron of the pyridine bisimine iron salt complex concentration in a range of $5\times10^{-4}$ mmol/kg to $5\times10^{-3}$ mmol/kg, ii) an aluminum of the organoaluminum compound to iron of the pyridine bisimine iron salt complex molar ratio in a range of 300:1 to 800:1, iii) an ethylene partial pressure in a range of 750 psig to 1200 psig, iv) an ethylene to organic reaction medium mass ratio of 0.8 to 4.5, and v) an average temperature in a range of 75° C. to 95° C.; and optionally vi) a hydrogen partial pressure of at least 5 psi.

Also disclosed herein is a process comprising A) continuously introducing into a reaction zone i) ethylene, ii) an iron salt iii) a pyridine bisimine, iv) an organoaluminum compound, and v) an organic reaction medium comprising one or more $C_8$ to $C_{18}$ aliphatic hydrocarbons; and B) forming an oligomer product in the reaction zone, the reaction zone having an average temperature in a range of 75° C. to 95° C.

Also disclosed herein is a process comprising A) continuously introducing into a reaction zone i) ethylene, ii) a pyridine bisimine iron salt complex, iii) an organoaluminum compound, and iv) an organic reaction medium comprising one or more $C_8$ to $C_{18}$ aliphatic hydrocarbons; and B) forming an oligomer product in the reaction zone, the reaction zone having an average temperature in a range of 75° C. to 95° C.

BRIEF DESCRIPTION OF THE DRAWINGS

The FIGURE is an illustration of the oligomerization reaction system utilized in the examples.

DETAILED DESCRIPTION

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Groups of elements of the periodic table are indicated using the numbering scheme indicated in the version of the periodic table of elements published in Chemical and Engineering News, 63(5), 27, 1985. In some instances a group of elements can be indicated using a common name assigned to the group; for example alkali metals for Group 1 elements, alkaline earth metals for Group 2 elements, transition metals for Group 3-12 elements, and halogens for Group 17 elements.

Regarding claim transitional terms or phrases, the transitional term "comprising", which is synonymous with "including," "containing," "having," or "characterized by,"

is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. A "consisting essentially of" claim occupies a middle ground between closed claims that are written in a "consisting of" format and fully open claims that are drafted in a "comprising" format. Absent an indication to the contrary, when describing a compound or composition "consisting essentially of" is not to be construed as "comprising," but is intended to describe the recited component that includes materials which do not significantly alter the composition or method to which the term is applied. For example, a feedstock consisting essentially of a material A can include impurities typically present in a commercially produced or commercially available sample of the recited compound or composition. When a claim includes different features and/or feature classes (for example, a method step, feedstock features, and/or product features, among other possibilities), the transitional terms comprising, consisting essentially of, and consisting of apply only to the feature class which is utilized and it is possible to have different transitional terms or phrases utilized with different features within a claim. For example, a method can comprise several recited steps (and other non-recited steps) but utilize a catalyst system preparation consisting of specific or alternatively, consist of specific steps and/or utilize a catalyst system comprising recited components and other non-recited components. In another instance, the disclosure using a specified material of a can be interpreted as comprising (consisting essentially of, or consisting of) at least one of the specified material, or can be interpreted as comprising (consisting essentially of, or consisting of) one of more of the specified materials. For example, in general, a claim feature reciting "consisting essentially of a $C_6$ to $C_{16}$ compound" can be interpreted or rewritten to recite "consisting essentially of at least one $C_6$ to $C_{16}$ compound," or "consisting essentially of one or more $C_6$ to $C_{16}$ compounds."

While compositions and methods are described in terms of "comprising" various components or steps, the compositions and methods can also "consist essentially of" or "consist of" the various components or steps.

In the specification and claims, the terms "a," "an," and "the" are intended, unless specifically indicated otherwise, to include plural alternatives, e.g., at least one, or one or more. For instance, the disclosure of "a trialkylaluminum compound" is meant to encompass one trialkylaluminum compound, or mixtures or combinations of more than one trialkylaluminum compound unless otherwise specified. In another instance, the disclosure using a specified material can be interpreted as comprising (consisting essentially of, or consisting of) at least one of the specified material, or can be interpreted as comprising (consisting essentially of, or consisting of) one of more of the specified materials. For example, in general, a claim feature reciting "consisting essentially of a $C_6$ to $C_{16}$ compound" can be interpreted or rewritten to recite "consisting essentially of at least one $C_6$ to $C_{16}$ compound," or "consisting essentially of one or more $C_6$ to $C_{16}$ compounds."

In this disclosure, the terms first, second, and third, among others, can be utilized to differentiate multiple occurrences of a similar element. For example a method can utilize two or more solvents in different steps of a method, or alternatively, two different solvents in a mixture. The differentiating term can be applied to any element described herein when necessary to provide a differentiation. It should be understood that the numerical or alphabetical precedence of the differentiating terms do not imply a particular order or preference of the element in a method or compound described herein unless specifically specified otherwise.

In this disclosure, a process can have multiple steps or can include features having a number of different elements (e.g., components in a catalyst system or components in an olefin oligomerization process, among other features). These steps and/or elements can be designated utilizing the series a), b), c), etc., i), ii), iii), etc., (a), (b), (c), etc., and/or (i), (ii), (iii), etc. (among other designation series) as necessary to provide a designation for each process step and/or element. It should be understood that the numerical or alphabetical precedence of the designations within a designation series does not imply a particular order or preference of the process step in a process described herein, the feature(s) described herein, and/or an element(s) in a feature unless specifically specified otherwise or necessitated by other process steps, elements, and/or element features. Additionally, these designations series are provided to differentiate different process steps and/or elements in a feature and can be utilized as necessary, and without regard to the designation series utilized for a particular step, element, or feature utilized within this description as long as the designation series consistently distinguish different features, different process steps, and/or different elements of a feature.

For any particular compound disclosed herein, the general structure or name presented is also intended to encompass all structural isomers, conformational isomers, and stereoisomers that can arise from a particular set of substituents, unless indicated otherwise. Thus, a general reference to a compound includes all structural isomers unless explicitly indicated otherwise; e.g., a general reference to pentane includes n-pentane, 2-methyl-butane, and 2,2-dimethylpropane while a general reference to a butyl group includes an n-butyl group, a sec-butyl group, an iso-butyl group, and a tert-butyl group. Additionally, the reference to a general structure or name encompasses all enantiomers, diastereomers, and other optical isomers whether in enantiomeric or racemic forms, as well as mixtures of stereoisomers, as the context permits or requires. For any particular formula or name that is presented, any general formula or name presented also encompasses all conformational isomers, regioisomers, and stereoisomers that can arise from a particular set of substituents. Thus, a general reference to a compound includes all structural isomers unless explicitly indicated otherwise; e.g., a general reference to a $C_6$ hydrocarbon refers to all hydrocarbon having 6 carbon atoms, a general reference to pentane includes n-pentane, 2-methyl-butane, and 2,2-dimethylpropane, and a general reference to a butyl group includes an n-butyl group, a sec-butyl group, an iso-butyl group, and a tert-butyl group.

A chemical "group" is described according to how that group is formally derived from a reference or "parent" compound, for example, by the number of hydrogen atoms formally removed from the parent compound to generate the group, even if that group is not literally synthesized in this manner. These groups can be utilized as substituents or coordinated or bonded to metal atoms. By way of example, an "alkyl group" formally can be derived by removing one hydrogen atom from an alkane, while an "alkylene group" formally can be derived by removing two hydrogen atoms from an alkane. Moreover, a more general term can be used to encompass a variety of groups that formally are derived by removing any number ("one or more") hydrogen atoms from a parent compound, which in this example can be described as an "alkane group," and which encompasses an "alkyl group," an "alkylene group," and materials have three or more hydrogens atoms, as necessary for the situation, removed from the alkane. Throughout, the disclosure that a substituent, ligand, or other chemical moiety can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedure, unless specified otherwise or the context requires otherwise.

The term "substituted" when used to describe a group, for example, when referring to a substituted analog of a particular group, is intended to describe any non-hydrogen moiety that formally replaces a hydrogen in that group, and is intended to be non-limiting. A group or groups can also be referred to herein as "unsubstituted" or by equivalent terms such as "non-substituted," which refers to the original group in which a non-hydrogen moiety does not replace a hydrogen within that group. "Substituted" is intended to be non-limiting and include inorganic substituents or organic substituents.

The term "organyl group" is used herein in accordance with the definition specified by IUPAC: an organic substituent group, regardless of functional type, having one free valence at a carbon atom. Similarly, an "organylene group" refers to an organic group, regardless of functional type, derived by removing two hydrogen atoms from an organic compound, either two hydrogen atoms from one carbon atom or one hydrogen atom from each of two different carbon atoms. An "organic group" refers to a generalized group formed by removing one or more hydrogen atoms from carbon atoms of an organic compound. Thus, an "organyl group," an "organylene group," and an "organic group" can contain organic functional group(s) and/or atom(s) other than carbon and hydrogen, that is, an organic group can comprise functional groups and/or atoms in addition to carbon and hydrogen. For instance, non-limiting examples of atoms other than carbon and hydrogen include halogens, oxygen, nitrogen, phosphorus, and the like. Non-limiting examples of functional groups include ethers, aldehydes, ketones, esters, sulfides, amines, phosphines, and so forth.

For the purposes of this application, the term or variations of the term "organyl group consisting essentially of inert functional groups" refers to an organyl group (having a free valence on a carbon atom) wherein the organic functional group(s) and/or atom(s) other than carbon and hydrogen present in the functional group are restricted to those functional group(s) and/or atom(s) other than carbon and hydrogen which do not complex with a metal compound and/or are inert under the process conditions defined herein. Thus, the term or variation of the term "organyl group consisting essentially of inert functional groups" further defines the particular organyl groups that can be present within the organyl group consisting essentially of inert functional groups. Additionally, the term "organyl group consisting essentially of inert functional groups" can refer to the presence of one or more inert functional groups within the organyl group. The term or variation of the term "organyl group consisting essentially of inert functional groups" definition includes the hydrocarbyl group as a member (among other groups). Similarly, an "organylene group consisting essentially of inert functional groups" refers to an organic group formed by removing two hydrogen atoms from one or two carbon atoms of an organic compound consisting of inert functional groups and an "organic group consisting essentially of inert functional groups" refers to a generalized organic group consisting essentially of inert functional groups formed by removing one or more hydrogen atoms from one or more carbon atoms of an organic compound consisting of inert functional groups.

For purposes of this application, an "inert functional group" is a group having a free valence on a heteroatom which does not substantially interfere with the process described herein in which the material having an inert functional group takes part and/or does not complex with the metal compound of the metal complex. The term "does not complex with the metal compound" can include groups that could complex with a metal compound but in particular molecules described herein may not complex with a metal compound due to its positional relationship within a ligand. For example, while a hydrocarboxy group can complex with a metal compound, a hydrocarboxy group located at a para position of a substituted pyridine ring or substituted imine phenyl group can be an inert functional group because a single metal compound molecule cannot complex with the three nitrogen atoms of a pyridine bisimine ligand and the para hydrocarboxy group within the same metal complex molecule. Thus, the inertness of a particular functional group is not only related to the functional group's inherent inability to complex the metal compound but can also be related to the functional group's position within the metal complex. Non-limiting examples of inert functional groups which do not substantially interfere with processes described herein can include a halide (fluoride, chloride, bromide, and iodide), nitro, hydrocarboxy groups (e.g., alkoxy, and/or aroxy, among others), and/or hydrocarbosulfidyl groups (e.g., RS-), among others.

The term "hydrocarbon" whenever used in this specification and claims refers to a compound containing only carbon and hydrogen. Other identifiers can be utilized to indicate the presence of particular groups in the hydrocarbon (e.g., halogenated hydrocarbon indicates that the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon. Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as necessary for the particular group) from a hydrocarbon. A "hydrocarbyl group," "hydrocarbylene group," and "hydrocarbon group" can be acyclic or cyclic groups, and/or can be linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene, alkyl, alkylene, alkane, cycloalkyl, cycloalkylene, cycloalkane, aralkyl, aralkylene, and aralkane groups, among other groups, as members.

The term "alkane" whenever used in this specification and claims refers to a saturated hydrocarbon compound. Other identifiers can be utilized to indicate the presence of particular groups in the alkane (e.g., halogenated alkane indicates that the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic groups, and/or can be linear or branched unless otherwise specified.

A cycloalkane is a saturated cyclic hydrocarbon, with or without side chains, for example, cyclobutane. Unsaturated cyclic hydrocarbons having one or more endocyclic double or one triple bond are called cycloalkenes and cycloalkynes, respectively. Cycloalkenes and cycloalkynes having only one, only two, only three, etc. . . . endocyclic double or triple bonds, respectively, can be identified by use of the term "mono," "di," "tri, etc. . . . within the name of the cycloalkene or cycloalkyne. Cycloalkenes and cycloalkynes can further identify the position of the endocyclic double or triple bonds.

A "cycloalkyl group" is a univalent group derived by removing a hydrogen atom from a ring carbon atom of a cycloalkane. For example, a 1-methylcyclopropyl group and a 2-methylcyclopropyl group are illustrated as follows.

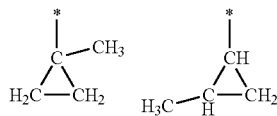

Similarly, a "cycloalkylene group" refers to a group derived by removing two hydrogen atoms from a cycloalkane, at least one of which is a ring carbon. Thus, a "cycloalkylene group" includes both a group derived from a cycloalkane in which two hydrogen atoms are formally removed from the same ring carbon, a group derived from a cycloalkane in which two hydrogen atoms are formally removed from two different ring carbons, and a group derived from a cycloalkane in which a first hydrogen atom is formally removed from a ring carbon and a second hydrogen atom is formally removed from a carbon atom that is not a ring carbon. A "cycloalkane group" refers to a generalized group formed by removing one or more hydrogen atoms (as necessary for the particular group and at least one of which is a ring carbon) from a cycloalkane. It should be noted that according to the definitions provided herein, general cycloalkane groups (including cycloalkyl groups and cycloalkylene groups) include those having zero, one, or more than one hydrocarbyl substituent groups attached to a cycloalkane ring carbon atom (e.g., a methylcyclopropyl group) and is member of the group of hydrocarbon groups. However, when referring to a cycloalkane group having a specified number of cycloalkane ring carbon atoms (e.g., cyclopentane group or cyclohexane group, among others), the base name of the cycloalkane group having a defined number of cycloalkane ring carbon atoms refers to the unsubstituted cycloalkane group (including having no hydrocarbyl groups located on cycloalkane group ring carbon atom). Consequently, a substituted cycloalkane group having a specified number of ring carbon atoms (e.g., substituted cyclopentane or substituted cyclohexane, among others) refers to the respective group having one or more substituent groups (including halogens, hydrocarbyl groups, or hydrocarboxy groups, among other substituent groups) attached to a cycloalkane group ring carbon atom. When the substituted cycloalkane group having a defined number of cycloalkane ring carbon atoms is a member of the group of hydrocarbon groups (or a member of the general group of cycloalkane groups), each substituent of the substituted cycloalkane group having a defined number of cycloalkane ring carbon atoms is limited to hydrocarbyl substituent group. One can readily discern and select general groups, specific groups, and/or individual substituted cycloalkane group(s) having a specific number of ring carbons atoms which can be utilized as member of the hydrocarbon group (or a member of the general group of cycloalkane groups).

The term "olefin" whenever used in this specification and claims refers to hydrocarbon compounds that have at least one carbon-carbon double bond that is not part of an aromatic ring or an aromatic ring system. The term "olefin" includes aliphatic and aromatic, cyclic and cyclic, and/or linear and branched compounds having at least one carbon-carbon double bond that is not part of an aromatic ring or ring system unless specifically stated otherwise. Olefins having only one, only two, only three, etc. . . . carbon-carbon double bonds can be identified by use of the term "mono," "di," "tri," etc. . . . within the name of the olefin. The olefins can be further identified by the position of the carbon-carbon double bond(s).

The term "alkene" whenever used in this specification and claims refers a linear or branched aliphatic hydrocarbon olefin that has one or more carbon-carbon double bonds. Alkenes having only one, only two, only three, etc. . . . such multiple bond can be identified by use of the term "mono," "di," "tri," etc. within the name. Alkenes can be further identified by the position of the carbon-carbon double bond(s). Other identifiers can be utilized to indicate the presence or absence of particular groups within an alkene. For example, a haloalkene refers to an alkene having one or more hydrogen atoms replace with a halogen atom.

The term "alpha olefin" as used in this specification and claims refers to an olefin that has a carbon-carbon double bond between the first and second carbon atom of the longest contiguous chain of carbon atoms. The term "alpha olefin" includes linear and branched alpha olefins unless expressly stated otherwise. In the case of branched alpha olefins, a branch can be at the 2-position (a vinylidene) and/or the 3-position or higher with respect to the olefin double bond. The term "vinylidene" whenever used in this specification and claims refers to an alpha olefin having a branch at the 2-position with respect to the olefin double bond. By itself, the term "alpha olefin" does not indicate the presence or absence of other carbon-carbon double bonds unless explicitly indicated.

The term "normal alpha olefin" whenever used in this specification and claims refers to a linear aliphatic mono-olefin having a carbon-carbon double bond between the first and second carbon atoms. It is noted that "normal alpha olefin" is not synonymous with "linear alpha olefin" as the term "linear alpha olefin" can include linear olefinic compounds having a double bond between the first and second carbon atoms and additional double bonds.

An aliphatic compound is an acyclic or cyclic, saturated or unsaturated, carbon compound, excluding aromatic compounds. An "aliphatic group" is a generalized group formed by removing one or more hydrogen atoms (as necessary for the particular group) from the carbon atom of an aliphatic compound. Aliphatic compounds and therefore aliphatic groups can contain organic functional group(s) and/or atom(s) other than carbon and hydrogen.

An aromatic compound is a compound containing a cyclically conjugated double bond system that follows the Hückel (4n+2) rule and contains (4n+2) pi-electrons, where n is an integer from 1 to 5. Aromatic compounds include "arenes" (hydrocarbon aromatic compounds) and "heteroarenes," also termed "hetarenes" (heteroaromatic compounds formally derived from arenes by replacement of one or more methine (—C=) carbon atoms of the cyclically conjugated double bond system with a trivalent or divalent heteroatoms, in such a way as to maintain the continuous pi-electron system characteristic of an aromatic system and a number of out-of-plane pi-electrons corresponding to the Bickel rule (4n+2). While arene compounds and heteroarene compounds are mutually exclusive members of the group of aromatic compounds, a compound that has both an arene group and a heteroarene group are generally considered a heteroarene compound. Aromatic compounds, arenes, and heteroarenes can be monocyclic (e.g., benzene, toluene, furan, pyridine, methylpyridine) or polycyclic unless otherwise specified. Polycyclic aromatic compounds, arenes, and heteroarenes, include, unless otherwise specified, compounds wherein the aromatic rings can be fused (e.g., naphthalene, benzofuran, and indole), compounds where the aromatic groups can be separate and joined by a bond (e.g., biphenyl or 4-phenylpyridine), or compounds where the aromatic groups are joined by a group containing linking atoms (e.g., carbon—the methylene group in diphenylmethane; oxygen—diphenyl ether; nitrogen—triphenyl amine; among others linking groups). As disclosed herein, the term "substituted" can be used to describe an aromatic group, arene, or heteroarene wherein a non-hydrogen moiety formally replaces a hydrogen in the compound, and is intended to be non-limiting.

An "aromatic group" refers to a generalized group formed by removing one or more hydrogen atoms (as necessary for the particular group and at least one of which is an aromatic ring carbon atom) from an aromatic compound. For a univalent "aromatic group," the removed hydrogen atom must be from an aromatic ring carbon. For an "aromatic group" formed by removing more than one hydrogen atom from an aromatic compound, at least one hydrogen atom must be from an aromatic hydrocarbon ring carbon. Additionally, an "aromatic group" can have hydrogen atoms removed from the same ring of an aromatic ring or ring system (e.g., phen-1,4-ylene, pyridin-2,3-ylene, naphth-1,2-ylene, and benzofuran-2,3-ylene), hydrogen atoms removed from two different rings of a ring system (e.g., naphth-1,8-ylene and benzofuran-2,7-ylene), or hydrogen atoms removed from two isolated aromatic rings or ring systems (e.g., bis(phen-4-ylene)methane).

An arene is aromatic hydrocarbon, with or without side chains (e.g., benzene, toluene, or xylene, among others). An "aryl group" is a group derived from the formal removal of a hydrogen atom from an aromatic ring carbon of an arene. It should be noted that the arene can contain a single aromatic hydrocarbon ring (e.g., benzene, or toluene), contain fused aromatic rings (e.g., naphthalene or anthracene), and contain one or more isolated aromatic rings covalently linked via a bond (e.g., biphenyl) or non-aromatic hydrocarbon group(s) (e.g., diphenylmethane).

Similarly, an "arylene group" refers to a group formed by removing two hydrogen atoms (at least one of which is from an aromatic ring carbon) from an arene. An "arene group" refers to a generalized group formed by removing one or more hydrogen atoms (as necessary for the particular group and at least one of which is an aromatic ring carbon) from an arene. It should be noted that according the definitions provided herein, general arene groups (including an aryl group and an arylene group) include those having zero, one, or more than one hydrocarbyl substituent groups located on an aromatic hydrocarbon ring or ring system carbon atom (e.g., a toluene group or a xylene group, among others) and is a member of the group of hydrocarbon groups. However, a phenyl group (or phenylene group) and/or a naphthyl group (or naphthylene group) refer to the specific unsubstituted arene groups (including no hydrocarbyl group located on an aromatic hydrocarbon ring or ring system carbon atom). Consequently, a substituted phenyl group or substituted naphthyl group refers to the respective arene group having one or more substituent groups (including halogens, hydrocarbyl groups, or hydrocarboxy groups, among others) located on an aromatic hydrocarbon ring or ring system carbon atom. When the substituted phenyl group and/or substituted naphtyl group is a member of the group of hydrocarbon groups (or a member of the general group of arene groups), each substituent is limited to a hydrocarbyl substituent group. One having ordinary skill in the art can readily discern and select general phenyl and/or naphthyl groups, specific phenyl and/or naphthyl groups, and/or individual substituted phenyl or substituted naphthyl groups which can be utilized as a member of the group of hydrocarbon groups (or a member of the general group of arene groups).

An "aralkyl group" is an aryl-substituted alkyl group having a free valance at a non-aromatic carbon atom (e.g., a benzyl group, or a 2-phenyleth-1-yl group, among others). Similarly, an "aralkylene group" is an aryl-substituted alkylene group having two free valencies at a single non-aromatic carbon atom or a free valence at two non-aromatic carbon atoms while an "aralkane group" is a generalized aryl-substituted alkane group having one or more free valencies at a non-aromatic carbon atom(s). It should be noted that according the definitions provided herein, general aralkane groups include those having zero, one, or more than one hydrocarbyl substituent groups located on an aralkane aromatic hydrocarbon ring or ring system carbon atom and is a member of the group of hydrocarbon groups. However, specific aralkane groups specifying a particular aryl group (e.g., the phenyl group in a benzyl group or a 2-phenylethyl group, among others) refer to the specific unsubstituted aralkane groups (including no hydrocarbyl group located on the aralkane aromatic hydrocarbon ring or ring system carbon atom). Consequently, a substituted aralkane group specifying a particular aryl group refers to a respective aralkane group having one or more substituent groups (including halogens, hydrocarbyl groups, or hydrocarboxy groups, among others). When the substituted aralkane group specifying a particular aryl group is a member of the group of hydrocarbon groups (or a member of the general group of aralkane groups), each substituent is limited to a hydrocarbyl substituent group. One can readily discern and select substituted aralkane groups specifying a particular aryl group which can be utilized as a member of the group of hydrocarbon groups (or a member of the general group of aralkane groups).

A "primary carbon atom group," a "secondary carbon atom group," a "tertiary carbon atom group," and a "quaternary carbon atom group" describe the type of carbon atom which would be created when the group is attached to a base structure. A "primary carbon atom group" is a group wherein the carbon atom bonded to the base structure is also bonded to three monovalent atoms (e.g., hydrogen or halides) in addition to the base structure. A methyl group, a trifluormethyl group (among other group) attached to a base structure represent potential "primary carbon atom groups." A "secondary carbon atom group" is a group wherein the carbon atom bonded to the base structure is bonded to one other non-monovalent atom (e.g., carbon, nitrogen, or oxygen, among others) and two monovalent atoms. An ethyl group, a 1-chloroeth-1-yl group, and a methoxymethyl group (among others) attached to a base structure represent potential "secondary carbon atom groups." A "tertiary carbon group" is a group wherein the carbon atom bonded to the base structure is bonded to two other non-monovalent atoms and one monovalent atom. An isopropyl group, a 2-chloroprop-1-yl group, a phenyl group, and a 1-methoxyethy-1-yl group (among others) attached to a base structure represent potential "tertiary carbon groups." A "quaternary carbon group" is a group wherein the carbon atom bonded to the base structure is also bonded to three other non-monovalent atoms. A tert-butyl group and a 2-methoxyprop-2-yl group (among others) attached to a base structure represent potential "quaternary carbon groups."

A "halide" has its usual meaning; therefore, examples of halides include fluoride, chloride, bromide, and iodide.

Within this disclosure the normal rules of organic nomenclature will prevail. For instance, when referencing substituted compounds or groups, references to substitution patterns are taken to indicate that the indicated group(s) is (are) located at the indicated position and that all other non-indicated positions are hydrogen. For example, reference to a 4-substituted phenyl group indicates that there is a non-hydrogen substituent located at the 4 position and hydrogens located at the 2, 3, 5, and 6 positions. By way of another example, reference to a 3-substituted naphth-2-yl indicates that there is a non-hydrogen substituent located at the 3 position and hydrogens located at the 1, 4, 5, 6, 7, and 8 positions. References to compounds or groups having substitutions at positions in addition to the indicated position will be reference using comprising or some other alternative language. For example, a reference to a phenyl group comprising a substituent at the 4-position refers to a group having a non-hydrogen atom at the 4-position and hydrogen or any other non-hydrogen group at the 2-, 3-, 5-, and 6-positions.

The term "reaction zone effluent," and it derivatives (e.g., oligomerization reaction zone effluent) generally refers to all the material which exits the reaction zone. The term "reaction zone effluent," and its derivatives, can also be prefaced with other descriptors that limit the portion of the reaction zone effluent being referenced. For example, the term "reaction zone effluent" would refer to all material exiting the reaction zone (e.g., product and solvent or diluent, among others), while the term "olefin reaction zone effluent" refers to only the olefins within the reaction zone effluent and the term "oligomer product reactor effluent" refers to oligomer product within the reaction zone effluent.

The term "oligomerization," and its derivatives, refers to processes which produce a mixture of products containing at least 70 wt. % products containing from 2 to 30 monomer units. Similarly, an "oligomer" is a product that contains from 2 to 30 monomer units while an "oligomer product" or an "oligomerization product" includes all products made by the "oligomerization" process including the "oligomers" and products which are not "oligomers" (e.g., products which contain more than 30 monomer units). It should be noted that the monomer units in the "oligomer" or "oligomerization product" do not have to be the same. For example, an "oligomer," "oligomer product," or "oligomerization product" of an "oligomerization" process using ethylene and propylene as monomers can contain both ethylene and/or propylene units.

"K value" (sometimes referred to as Schulz-Flory chain growth factor, K or Schulz-Flory K value) can be defined the equation: $K=X_{q+1}/X_q$ wherein $X_{q+1}$ is the number of moles of oligomer product produced having q+1 monomer (e.g., ethylene) units and $X_q$ is the number of moles of oligomer product produced having q monomer (e.g., ethylene) units. Generally, the K value can be determined using any two oligomers of the oligomer product which differs in the number of monomer units by 1. However, one would appreciate that product isolation and analysis can lead to inaccuracies in a determined oligomer product distribution using particular oligomers (e.g., incomplete recovery of gaseous product and/or solid product during product isolation). One having ordinary skill in the art would recognize such issues and can choose the appropriate oligomers upon which to base the determination of the oligomer product distribution K value.

"Catalyst system productivity" is defined as grams of a product produced per gram (or mole) of metal in the catalyst system utilized in the oligomerization. Catalyst system activity is defined as grams of a product produced per gram (or mole) of metal per unit of time (e.g., hour) of an oligomerization. Catalyst system productivity and/or activity can be stated in terms of various products of an oligomerization and/or components of catalyst system. For example, in an ethylene oligomerization process utilizing a catalyst system comprising an iron salt complex and an organoaluminum compound, the catalyst system productivity which can be utilized include (g oligomer product)/(g Fe), among other productivities.

Unless otherwise specified, the terms contacted, combined, and "in the presence of" refer to any addition sequence, order, or concentration for contacting or combining the recited two or more components. The combining or contacting of the components, according to the various methods described herein can occur in one or more contact zones under suitable contact conditions such as temperature, pressure, contact time, flow rates, etc. . . . The contact zone can be disposed in a vessel (e.g., a storage tank, tote, container, mixing vessel, reactor, etc.), a length of pipe (e.g., a tee, inlet, injection port, or header for combining component feed lines into a common line), or any other suitable apparatus for bringing the components into contact, unless otherwise specified. The processes can be carried out in a batch or continuous process as is suitable for a given embodiment, unless otherwise specified.

The terms "simultaneously," "simultaneously contact," "contact simultaneously," and their derivatives when referring to a contact method refers to a contact method wherein the two or more recited compounds, mixtures, streams, and/or compositions are contacted by flowing into a common junction, pot, vessel, or reactor, among others, at the same time. The terms "substantially simultaneously," "substantially simultaneously contact," "contact substantially simultaneously," and their derivatives when referring to a contact method refers to a contact method wherein, during the contact of two or more recited compounds, mixtures, streams, and/or compositions, the two or more recited compounds, mixtures, streams, and/or compositions are contacted such that for some period during the contact process the two or more recited compounds, mixtures, streams, and/or compositions flow into a common junction, pot, vessel, or reactor at the same time. It should be noted that the terms "substantially simultaneously," "substantially simultaneously contact," "contact substantially simultaneously," and their derivatives do not mean that the two or more recited compounds, mixtures, streams, and/or compositions are contacted simultaneously over the entire addition of each of the two or more recited compounds, mixtures, streams, and/or compositions. The terms "substantially simultaneously," "substantially simultaneously contact," "contact substantially simultaneously," and it derivatives include scenarios where the flow of one of the (or less than all of the) recited compounds, mixtures, streams, and/or compositions can be initiated into the common junction, pot, vessel, or reactor before the others and/or the flow of one of the (or less than all of the) recited compounds, mixtures, streams, and/or compositions into the common junction, pot, vessel, or reactor can be completed, stopped, or discontinued before the other recited compounds, mixtures, streams, and/or compositions. In any embodiment or aspect described herein, the terms "simultaneously," "simultaneously contact," "contact simultaneously," and their derivatives, these terms can be modified by the inclusion of a term providing a quantity of the each of the recited compounds, mixtures, streams, and/or compositions which can be contacted simultaneously indicate scenarios of various degrees of "substantially simultaneously," "substantially simultaneously contact," "contact substantially simultaneously," and their derivatives. For example, at least 20%, 30%, 40%, 50%, 60%, 70%, 75%, 80%, 85%, 90%, 95% of each of the recited compounds, mixtures, streams, and/or compositions can be "simultaneously contacted" or "contacted simultaneously." Generally, the percentages of the recited compounds, mixtures, streams, and/or compositions that can be "simultaneously contacted" or "contacted simultaneously" can be by weight (wt.), by volume (volume %), or by mole (mole %). Unless otherwise specified, recited compounds, mixtures, streams, and/or compositions that are "substantially simultaneously," "substantially simultaneously contact," "contact substantially simultaneously," and their derivatives shall mean that at least 50% of each of the recited compounds, mixtures, streams, and/or compositions can be "simultaneously contacted" or "contacted simultaneously."

It should be further noted, that in reference to contact method or process, "simultaneously," "simultaneously contact," "contact simultaneously," "substantially simultaneously contact," "contact substantially simultaneously," and their derivatives is different than a process or method wherein one or more a first materials (e.g., compound, mixture, stream, and/or composition) already resides in a pot, vessel, or reactor and one or more other compounds, mixtures, streams, and/or compositions are added to the pot, vessel, or reactor. In this instance the first material in the pot, vessel, or reactor does not flow into the pot, vessel, or reactor concurrently with the other compounds, mixtures, streams, and/or compositions and the material in the pot. Thus, the first material and the other compounds, mixtures, streams, and/or compositions cannot be said to be "simultaneously contacted," "contacted simultaneously," "substantially simultaneously contacted," or "contacted substantially simultaneously" with the other component(s).

In an aspect, the processes disclosed herein can relate to processes comprising A) continuously introducing into a reaction zone i) ethylene, ii) a pyridine bisimine iron salt complex, iii) an organoaluminum compound, and iv) an organic reaction medium; and B) forming an oligomer product in the reaction zone; or alternatively, comprising A) continuously introducing into a reaction zone i) ethylene, ii) an iron salt, iii) a pyridine bisimine, iv) an organoaluminum compound, and v) an, at least one, or one or more, organic reaction medium(s); and B) forming an oligomer product in the reaction zone. Optionally, the processes can further comprise continuously introducing hydrogen into the reaction zone. In embodiments utilizing hydrogen, the oligomer product can be formed at, the reaction zone can have, or the reaction zone can operate at a specified hydrogen partial pressure. In an embodiment, the processes can further comprise continuously discharging a reaction zone effluent from the reaction zone. In another embodiment, the processes can further comprise a) introducing the, the at least one, or the one or more, organic reaction mediums to the reaction zone prior to introducing the iron salt pyridine bisimine complex (or the iron salt and/or the pyridine bisimine compound) or the ethylene to the reaction zone and/or b) introducing 1) the pyridine bisimine iron salt complex (or alternatively the iron salt and the pyridine bisimine) to the reaction zone prior to introducing ethylene to the reaction zone. In an aspect, the oligomer product can be formed at, the reaction zone can have, or the reaction zone can operate at conditions capable of forming an oligomer product. Generally, the pyridine bisimine iron salt complex, the pyridine bisimine, the iron salt, the organoaluminum compound, the, the at least one, or the one or more, organic reaction medium(s), the reaction zone, the conditions at which the oligomer product can be formed, the conditions which the reaction zone can have, and/or the conditions at which the reaction can operate, where applicable, are independent elements of process described herein and are independently described herein. These independently described process elements can be utilized in any combination, and without limitation to further described the processes provided herein.

In one aspect, the process described herein can comprise A) continuously introducing into a reaction zone i) ethylene, ii) a pyridine bisimine iron salt complex, iii) an organoaluminum compound, and iv) an organic reaction medium comprising, or consisting essentially of, a, at least one, or one or more, specific organic reaction medium(s); and B) forming an oligomer product in the reaction zone, the reaction zone having a specified average temperature; or alternatively, comprise i) ethylene, ii) an iron salt, iii) a pyridine bisimine, iv) an organoaluminum compound, and v) an organic reaction medium comprising, or consisting essentially of, a at least one, or one or more, specific organic reaction medium(s); and B) forming an oligomer product in the reaction zone, the reaction zone having a specified average temperature. In an embodiment, the processes can further comprise continuously discharging a reaction zone effluent from the reaction zone. In another embodiment, the processes can further comprise a) introducing the, the at least one, or the one or more, organic reaction medium(s) to the reaction zone prior to introducing the iron salt pyridine bisimine complex, the iron salt, the pyridine bisimine compound, or ethylene to the reaction zone and/or b) introducing 1) the pyridine bisimine iron salt complex (or alternatively the iron salt and the pyridine bisimine) to the reaction zone prior to introducing ethylene to the reaction zone. In an embodiment wherein an iron salt and a pyridine bisimine are continuously introduced into a reaction zone, the oligomer product can be formed at, the reaction zone can have, or the reaction zone can operate at a specified an iron salt to pyridine bisimine equivalent ratio. In an embodiment of these processes, the oligomer product can be formed at, the reaction zone can have, or the reaction zone can operate at a specified iron of the pyridine bisimine iron salt complex concentration, a specified aluminum of the organo aluminum compound to iron of the pyridine bisimine iron salt complex molar ratio, a specified ethylene partial pressure, a specified ethylene to organic reaction medium mass ratio, a specified average temperature, a specified aluminum of the organoaluminum compound concentration, and/or a specified ethylene to organic reaction medium mass ratio. In other embodiments, these processes can optionally continuously introduce hydrogen into the reaction zone. In embodiments utilizing hydrogen, the oligomer product can be formed at, the reaction zone can have, or the reaction zone can operate at a specified hydrogen partial pressure. Generally, the pyridine bisimine iron salt complex, the pyridine bisimine, the iron salt, the organoaluminum compound, the organic reaction medium, the reaction zone, the specified iron of the pyridine bisimine iron salt complex concentration, the specified aluminum of the organo aluminum compound to iron of the pyridine bisimine iron salt complex molar ratio, the specified iron salt to pyridine bisimine equivalent ratio, the specified ethylene partial pressure, the specified ethylene to organic reaction medium mass ratio, the specified average temperature, the specified aluminum of the organoaluminum compound concentration, the specified ethylene to organic reaction medium mass ratio, the specified hydrogen partial pressure, and the specified organic reaction medium, where applicable, are independent elements of process described herein and are independently described herein. These independently described process elements can be utilized in any combination, and without limitation to further describe the processes provided herein.

In another aspect, the process described herein can comprise A) continuously introducing into a reaction zone i) ethylene, ii) a pyridine bisimine iron salt complex, iii) an organoaluminum compound, and iv) an, at least one, or one or more, organic reaction medium(s); and B) forming an oligomer product in the reaction zone, where the oligomer product can be formed at, the reaction zone can have, or the reaction zone can operate at i) a specified iron of the pyridine bisimine iron salt complex concentration, ii) a specified aluminum of the organo aluminum compound to iron of the pyridine bisimine iron salt complex molar ratio, iii) a specified ethylene partial pressure, iv) a specified ethylene to organic reaction medium mass ratio, and v) a specified average temperature; or alternatively, comprising A) continuously introducing into a reaction zone i) ethylene, ii) an iron salt, iii) a pyridine bisimine, iv) an organoaluminum compound, and v) an organic reaction medium comprising, or consisting essentially of, at least one, or one or more, specific aliphatic hydrocarbon(s); and B) forming an oligomer product in the reaction zone, where the oligomer product can be formed at, the reaction zone can have, or the reaction zone can operate at i) a specified iron of the pyridine bisimine iron salt complex concentration, ii) a specified aluminum of the organo aluminum compound to iron of the pyridine bisimine iron salt complex molar ratio, iii) a specified ethylene partial pressure, iv) a specified ethylene to organic reaction medium mass ratio, and v) a specified average temperature. In an embodiment, the processes can further comprise continuously discharging a reaction zone effluent from the reaction zone. In another embodiment, the processes can further comprise a) introducing the, at least one, or one or more, organic reaction medium(s) to the reaction zone prior to introducing the iron salt pyridine bisimine complex, the iron salt, the pyridine bisimine compound, or the ethylene to the reaction zone and/or b) introducing 1) the pyridine bisimine iron salt complex (or alternatively the iron salt and the pyridine bisimine) to the reaction zone prior to introducing ethylene to the reaction zone. In an embodiment, these processes can utilize a, at least one, or one or more, specified organic reaction medium(s). In other embodiments, these processes can operate such that the oligomer product can be formed at, the reaction zone can have, or the reaction zone can operate at a specified aluminum of the organoaluminum compound concentration, and/or a specified ethylene to organic reaction medium mass ratio. In an embodiment wherein an iron salt and a pyridine bisimine are continuously introduced into a reaction zone, the oligomer product can be formed at, the reaction zone can have, or the reaction zone can operate at a specified iron salt to pyridine bisimine equivalent ratio. In other embodiments, these processes can optionally continuously introduce hydrogen into the reaction zone. In embodiments utilizing hydrogen, the oligomer product can be formed at, the reaction zone can have, or the reaction zone can operate at a specified hydrogen partial pressure. Generally, the pyridine bisimine iron salt complex, the pyridine bisimine, the iron salt, the organoaluminum compound, the organic reaction medium, the reaction zone, the specified iron of the pyridine bisimine iron salt complex concentration, the specified aluminum of the organo aluminum compound to iron of the pyridine bisimine iron salt complex molar ratio, the specified iron salt to pyridine bisimine equivalent ratio, the specified ethylene partial pressure, the specified ethylene to organic reaction medium mass ratio, the specified average temperature, the specified aluminum of the organoaluminum compound concentration, the specified ethylene to organic reaction medium mass ratio, the specified hydrogen partial pressure, and the specified organic reaction medium, where applicable, are independent elements of process described herein and are independently described herein. These independently described process elements can be utilized in any combination, and without limitation to further described the processes provided herein.

In any aspect or embodiment of the processes described herein, the oligomer product formed in the reaction zone can have a specified Schulz-Flory K value and/or can have a molecular weight distribution such that a specified amount of the oligomer product adhering to the reaction zone wall comprises polyethylene having an $M_r$ greater than 1000 g/mol. In any aspect or embodiment of the processes described herein, the reaction zone can be online a specified amount of time.

In various aspects and embodiments, a pyridine bisimine or a pyridine bisimine iron salt complex can be utilized in the processes described herein. Generally, the pyridine bisimine or the pyridine bisimine iron salt complex can be any pyridine bisimine or any pyridine bisimine iron salt complex that when contacted with ethylene and any other appropriate reagent(s) under the appropriate conditions can form an oligomer product. Generally, the pyridine bisimine and the iron salt of the pyridine bisimine iron salt complex are independent elements of the pyridine bisimine iron salt complex and are independently disclosed herein. The independent descriptions of the pyridine bisimine and the iron salt of the pyridine bisimine iron salt complex can be used without limitation and in any combination to further describe the pyridine bisimine iron salt complex that can be utilized in aspects and/or embodiments of the processes described herein. In an embodiment, the pyridine bisimine or the pyridine bisimine of the pyridine bisimine iron salt complex can comprise only one pyridine bisimine group; or alternatively, the pyridine bisimine can comprise only two pyridine bisimine groups.

In an aspect, the pyridine bisimine or the pyridine bisimine of the pyridine bisimine iron salt complex can have Structure PBI I or Structure PBI II; alternatively, Structure PBI I; or alternatively, Structure PBI II. In an aspect, the pyridine bisimine iron salt complex can have Structure PBIFe I or Structure PBIFe II; alternatively, Structure PBIFe I; or alternatively, Structure PBIFe II.

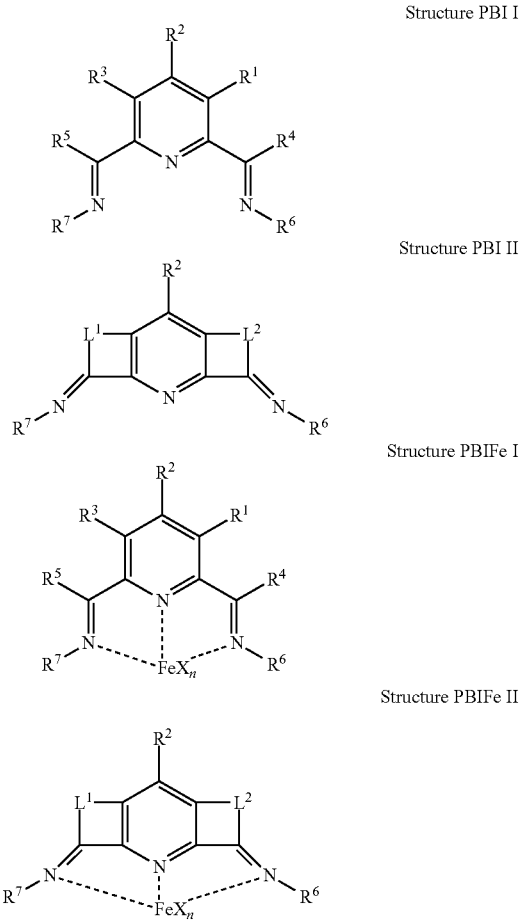

Structure PBI I

Structure PBI II

Structure PBIFe I

Structure PBIFe II $R^1$, $R^2$, $R^3$, $R^4$, $R^5$, $R^6$, and $R^7$ of the pyridine bisimine having Structure PBI I or the pyridine bisimine iron salt complex having Structure PBIFe I are independent elements of the pyridine bisimine having Structure PBI I and the pyridine bisimine iron salt complex having Structure PBIFe I and are independently described herein. The independent descriptions of $R^1$, $R^2$, $R^3$, $R^4$, $R^5$, $R^6$, and $R^7$ can be utilized without limitation, and in any combination, to further describe the pyridine bisimine having Structure PBI I and/or the pyridine bisimine iron salt complex having Structure PBIFe I. Similarly, $R^2$, $R^6$, $R^7$, $L^1$, and $L^2$ of the pyridine bisimine having Structure PBI II or the pyridine bisimine iron salt complex having Structure PBIFe II are independent elements of the pyridine bisimine having Structure PBI II and the pyridine bisimine iron salt complex having Structure PBIFe II and are independently described herein. The independent descriptions of $R^2$, $R^6$, $R^7$, $L^1$, and $L^2$ can be utilized without limitation, and in any combination, to further describe the pyridine bisimine having Structure PBI II and/or the pyridine bisimine iron salt complex having Structure PBIFe II. Additionally, the iron salt, $FeX_n$, is independently described herein can be combined, without limitation, with the independently described $R^1$, $R^2$, $R^3$, $R^4$, $R^5$, $R^6$, $R^7$, $L^1$, and $L^2$ to further describe the appropriate pyridine bisimine iron salt complex structure described herein which have an $R^1$, $R^2$, $R^3$, $R^4$, $R^5$, $R^6$, $R^7$, $L^1$, and/or Generally, $R^1$, $R^2$, and/or $R^3$ of the respective pyridine bisimines and pyridine bisimine iron salt complexes, which have an $R^1$, $R^2$, and/or $R^3$, independently can be hydrogen, an inert functional group, or an organyl group; alternatively, hydrogen or an organyl group; alternatively, an inert functional group or an organyl group; alternatively, hydrogen, an inert functional group, or an organyl group consisting essentially of inert functional groups; alternatively, hydrogen or an organyl group consisting essentially of inert functional groups; alternatively, an inert functional group or an organyl group consisting essentially of inert functional groups; alternatively, hydrogen, an inert functional group, or a hydrocarbyl group; alternatively, hydrogen or a hydrocarbyl group; alternatively, an inert functional group or a hydrocarbyl group; alternatively, hydrogen or an inert functional group; alternatively, hydrogen; alternatively, an organyl group; alternatively, organyl group consisting essentially of inert functional groups; or alternatively, a hydrocarbyl group. In any aspect and/or embodiment disclosed herein, the $R^1$, $R^2$, and/or $R^3$ organyl groups of the pyridine bisimines and/or pyridine bisimine iron salt complexes which have an $R^1$, $R^2$, and/or $R^3$ group, independently can be a $C_1$ to $C_{20}$, a $C_1$ to $C_{15}$, a $C_1$ to $C_{10}$, or a $C_1$ to $C_5$ organyl group. In any aspect or embodiment disclosed herein, the $R^1$, $R^2$, and/or $R^3$ organyl groups consisting essentially of inert functional groups, of the pyridine bisimines and/or pyridine bisimine iron salt complexes which have an $R^1$, $R^2$, and/or $R^3$ group, independently can be a $C_1$ to $C_{20}$, a $C_1$ to $C_{15}$, a $C_1$ to $C_{10}$, or a $C_1$ to $C_5$ organyl group consisting essentially of inert functional groups. In any aspect and/or embodiment disclosed herein, the $R^1$, $R^2$, and/or $R^3$ hydrocarbyl groups of the pyridine bisimines and/or pyridine bisimine iron salt complexes which have an $R^1$, $R^2$, and/or $R^3$ group, independently can be a $C_1$ to $C_{20}$, a $C_1$ to $C_{15}$, a $C_1$ to $C_{10}$, or a $C_1$ to $C_5$ hydrocarbyl group.

In any aspect and/or embodiment disclosed herein, the $R^1$, $R^2$, and/or $R^3$ hydrocarbyl groups of the pyridine bisimines and pyridine bisimine iron salt complexes which have an $R^1$, $R^2$, and/or $R^3$ group, independently can be a $C_1$ to $C_{20}$, a $C_1$ to $C_{10}$, or a $C_1$ to $C_5$ alkyl group. In an embodiment, the $R^1$, $R^2$, and/or $R^3$ alkyl groups of the pyridine bisimines and pyridine bisimine iron salt complexes which have an $R^1$, $R^2$, and/or $R^3$ group, independently can be a methyl group, an ethyl group, a propyl group, a butyl group, a pentyl group, a hexyl group, a heptyl group, or an octyl group. In some embodiments, the $R^1$, $R^2$, and/or $R^3$ alkyl groups of the pyridine bisimines and pyridine bisimine iron salt complexes which have an $R^1$, $R^2$, and/or $R^3$ group, independently can be a methyl group, an ethyl group, an iso-propyl (2-propyl) group, a tert-butyl (2-methyl-2-propyl) group, or a neopentyl (2,2-dimethyl-1-propyl) group; alternatively, a methyl group; alternatively, an ethyl group; alternatively, a n-propyl (1-propyl) group; alternatively, an iso-propyl (2-propyl) group; alternatively, a tert-butyl (2-methyl-2-propyl) group; or alternatively, a neopentyl (2,2-dimethyl-1-propyl) group.

In a particular aspect, $R^1$, $R^2$, and/or $R^3$ of the pyridine bisimines which have an $R^1$, $R^2$, and/or $R^3$ group, each can be hydrogen. In these aspects, the pyridine bisimine can have Structure PBI III or Structure PBI IV; alternatively, Structure PBI III; or alternatively, Structure PBI IV. Similarly, in a particular aspect, $R^1$, $R^2$, and $R^3$ of the pyridine bisimine iron salt complexes which have an $R^1$, $R^2$, and/or $R^3$ group, each can be hydrogen. In these aspects, the pyridine bisimine iron salt complexes can have Structure PBIFe III or Structure PBIFe IV; alternatively, Structure PBIFe III; or alternatively, Structure PBIFe IV.

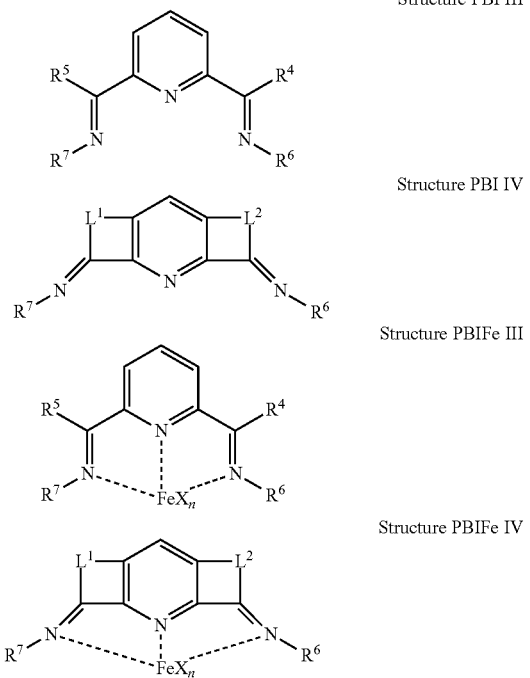

Structure PBI III

Structure PBI IV

Structure PBIFe III

Structure PBIFe IV $R^4$, $R^5$, $R^6$, and $R^7$ of the pyridine bisimine having Structure PBI III or the pyridine bisimine iron salt complex having Structure PBIFe III are independent elements of the pyridine bisimine having Structure PBI III and the pyridine bisimine iron salt complex having Structure PBIFe III and are independently described herein. The independent descriptions of $R^4$, $R^5$, $R^6$, and $R^7$ can be utilized without limitation, and in any combination, to further describe the pyridine bisimine having Structure PBI III and/or the pyridine bisimine iron salt complex having Structure PBIFe III. Similarly, $R^6$, $R^7$, $L^1$, and $L^2$ of the pyridine bisimine having Structure PBI IV or the pyridine bisimine iron salt complex having Structure PBIFe IV are independent elements of the pyridine bisimine having Structure PBI IV and the pyridine bisimine iron salt complex having Structure PBIFe IV and are independently described herein. The independent descriptions of $R^6$, $R^7$, $L^1$, and $L^2$ can utilized without limitation, and in any combination, to further describe the pyridine bisimine having Structure PBI IV and/or the pyridine bisimine iron salt complex having Structure PBIFe IV. Additionally, the iron salt, $FeX_n$, is independently described herein and can be combined, without limitation, with the independently described $R^4$, $R^5$, $R^6$, $R^7$, $L^1$, and $L^2$ to further describe the appropriate pyridine bisimine iron salt complex structure described herein which have an $R^4$, $R^5$, $R^6$, $R^7$, $L^1$, and/or $L^2$.

Generally, $R^4$ and/or $R^5$ of the pyridine bisimines and pyridine bisimine iron salt complexes, which have an $R^4$ and/or $R^5$, independently can be hydrogen or an organyl group; alternatively, hydrogen or an organyl group consisting essentially of inert functional groups; alternatively, hydrogen and a hydrocarbyl group; alternatively, hydrogen; alternatively, an organyl group; alternatively, an organyl group consisting essentially of inert functional groups; or alternatively, a hydrocarbyl group. In any aspect and/or embodiment disclosed herein, the $R^4$ and/or $R^5$ organyl groups of the pyridine bisimines and pyridine bisimine iron salt complexes which have an $R^4$ and/or $R^5$ group, independently can be a $C_1$ to $C_{20}$, a $C_1$ to $C_{15}$, a $C_1$ to $C_{10}$, or a $C_1$ to $C_5$ organyl group. In any aspect and/or embodiment disclosed herein, the $R^4$ and/or $R^5$ organyl groups consisting essentially of inert functional groups, of the pyridine bisimines and pyridine bisimine iron salt complexes which have an $R^4$ and/or $R^5$ group, independently can be a $C_1$ to $C_{20}$, a $C_1$ to $C_{15}$, a $C_1$ to $C_{10}$, or a $C_1$ to $C_5$ organyl group consisting essentially of inert functional groups. In any aspect and/or embodiment disclosed herein, the $R^4$ and/or $R^5$ hydrocarbyl groups of the pyridine bisimines and pyridine bisimine iron salt complexes which have an $R^4$ and/or $R^5$ group, independently can be a $C_1$ to $C_{20}$, a $C_1$ to $C_{15}$, a $C_1$ to $C_{10}$, or a $C_1$ to $C_5$ hydrocarbyl group.

In any aspect or embodiment disclosed herein, the $R^4$ and/or $R^5$ hydrocarbyl groups of the pyridine bisimines and pyridine bisimine iron salt complexes which have an $R^4$ and/or $R^5$ group, independently can be a $C_1$ to $C_{20}$, a $C_1$ to $C_{15}$, a $C_1$ to $C_{10}$, or a $C_1$ to $C_5$ alkyl group. In an embodiment, the $R^4$ and/or $R^5$ alkyl groups of the pyridine bisimines and pyridine bisimine iron salt complexes which have an $R^4$ and/or $R^5$ group, independently can be a methyl group, an ethyl group, a propyl group, a butyl group, a pentyl group, a hexyl group, a heptyl group, or an octyl group. In some embodiments, the $R^4$ and/or $R^5$ alkyl groups of the pyridine bisimines and pyridine bisimine iron salt complexes which have an $R^4$ and/or $R^5$ group, independently can be a methyl group, an ethyl group, an iso-propyl (2-propyl) group, a tert-butyl (2-methyl-2-propyl) group, or a neopentyl (2,2-dimethyl-1-propyl) group; alternatively, a methyl group; alternatively, an ethyl group; alternatively, a n-propyl (1-propyl) group; alternatively, an iso-propyl (2-propyl) group; alternatively, a tert-butyl (2-methyl-2-propyl) group; or alternatively, a neopentyl (2,2-dimethyl-1-propyl) group.

In an aspect, $R^1$ and $R^4$ and/or $R^3$ and $R^5$ can be joined to form a ring or a ring system containing two carbon atoms of the pyridine group and the carbon atom of the imine group. In such aspects, $L^1$ represents the joined $R^3$ and $R^5$ while $L^2$ represents the joined $R^1$ and $R^4$. Generally, $L^1$ and/or $L^2$ of a pyridine bisimine or pyridine bisimine iron salt complex having an $L^1$ and/or $L^2$ independently can be an organylene group; alternatively, an organylene group consisting essentially of inert functional groups; or alternatively, a hydrocarbylene group. In any aspect or embodiment disclosed herein, the $L^1$ and/or $L^2$ organylene groups of a pyridine bisimine or pyridine bisimine iron salt complex which have an $L^1$ and/or $L^2$ group, independently can be a $C_2$ to $C_{20}$, a $C_2$ to $C_{15}$, a $C_2$ to $C_{10}$, or a $C_2$ to $C_5$ organylene group. In any aspect or embodiment disclosed herein, the $L^1$ and/or $L^2$ organylene groups consisting essentially of inert functional groups of a pyridine bisimine or pyridine bisimine iron salt complex which have an $L^1$ and/or $L^2$ group, independently can be a $C_2$ to $C_{20}$, a $C_2$ to $C_{15}$, a $C_2$ to $C_{10}$, or alternatively, a $C_2$ to $C_5$ organylene group consisting essentially of inert functional groups. In any aspect or embodiment disclosed herein, the $L^1$ and/or $L^2$ hydrocarbylene groups of a pyridine bisimine or pyridine bisimine iron salt complex which have an $L^1$ and/or $L^2$ group, independently can be a $C_2$ to $C_{20}$, a $C_2$ to $C_{15}$, a $C_2$ to $C_{10}$, or a $C_2$ to $C_5$ hydrocarbylene group. In any aspect or embodiments disclosed herein, the $L^1$ and/or $L^2$ hydrocarbylene groups of the pyridine bisimines and pyridine bisimine iron salt complexes which have an $L^1$ and/or $L^2$, independently can be a $C_2$ to $C_{20}$, a $C_2$ to $C_{10}$, or a $C_2$ to $C_5$ alkylene group. In any aspect or embodiment where the pyridine bisimine or the pyridine bisimine iron salt complex has an $L^1$ and an $L^2$ group, $L^1$ and $L^2$ can be different; or alternatively, $L^1$ and $L^2$ can be the same.

In an aspect, $L^1$ and/or $L^2$ independently can have the structure $—(C(R^{11})_2)_p—$. Generally, $R^{11}$ and p are independent features of $L^1$ and/or $L^2$ having the structure $—(C(R^{11})_2)_p—$ and are independently described herein. The independent descriptions of $R^{11}$ and p can be utilized without limitation, and in any combination, to describe $L^1$ and/or $L^2$ having the structure $—(CR^{11})_p—$ and can be further utilized to describe the pyridine bisimines and/or the pyridine bisimine iron salt complexes which have an $L^1$ and/or $L^2$. In an embodiment, each $R^{11}$ independently can be hydrogen, an inert functional group, or a hydrocarbyl group; alternatively, hydrogen or a hydrocarbyl group; alternatively, hydrogen; or alternatively, a hydrocarbyl group. General and specific inert functional groups and hydrocarbyl groups are independently described herein (e.g., as potential substituent groups) and these descriptions can be utilized without limitation to further describe $L^1$ and $L^2$. In an aspect, each p independently can be an integer from 2 to 5; alternatively, an integer from 2 to 3; alternatively, 2; or alternatively, 3. In a non-limiting embodiment, $L^1$ and $L^2$ independently can be —CH$_2$CH$_2$—, —CH$_2$CH$_2$CH$_2$—, —CH(CH$_3$)CH$_2$—, —C(CH$_3$)$_2$—, or —CH$_2$CH$_2$CH$_2$CH$_2$—; alternatively, —CH$_2$CH$_2$- or —CH$_2$CH$_2$CH$_2$—; alternatively, —CH$_2$CH$_2$—; or alternatively, —CHCH$_2$CH$_2$-. In an embodiment, $L^1$ and $L^2$ can be different. In other embodiments, $L^1$ and $L^2$ can be the same.

Generally, $R^6$ and/or $R^7$ of the pyridine bisimines and the pyridine bisimine iron salt complexes independently can be an aryl group, a substituted aryl group, a phenyl group, or a substituted phenyl group; alternatively, aryl group or a substituted aryl group; alternatively, a phenyl group or a substituted phenyl group; alternatively, an aryl group; alternatively, a substituted aryl group; alternatively, a phenyl group; or alternatively, a substituted phenyl group. In any aspect and/or embodiment disclosed herein, the $R^6$ and/or $R^7$ aryl groups of the pyridine bisimines and/or pyridine bisimine iron salt complexes independently can be a $C_6$ to $C_{20}$, a $C_6$ to $C_{15}$, or a $C_6$ to $C_{10}$ aryl group. In any aspect and/or embodiment disclosed herein, the $R^6$ and/or $R^7$ substituted aryl groups of the pyridine bisimines and/or pyridine bisimine iron salt complexes independently can be a $C_6$ to $C_{20}$, a $C_6$ to $C_{15}$, or a $C_6$ to $C_{10}$ substituted aryl group. In any aspect or embodiment disclosed herein, the $R^6$ and/or $R^7$ substituted phenyl groups of the pyridine bisimines and/or pyridine bisimine iron salt complexes independently can be a $C_6$ to $C_{20}$, a $C_6$ to $C_{15}$, or a $C_6$ to $C_{15}$ substituted phenyl group. Each substituent of a substituted aryl group (general or specific) or a substituted phenyl group (general or specific) which can be utilized as $R^6$ and/or $R^7$ can be a halide, an alkyl group, or a hydrocarboxy group; alternatively, a halide or an alkyl group; alternatively, a halide or a hydrocarboxy group; alternatively, an alkyl group or a hydrocarboxy group; alternatively, a halide; alternatively, an alkyl group; or alternatively, a hydrocarboxy group. Halides, alkyl groups (general and specific), and hydrocarboxy groups (general and specific) that can be utilized as substituents are independently disclosed herein and can be utilized without limitation, and in any combination, to further describe $R^6$ and/or $R^7$ of the pyridine bisimines and the pyridine bisimine iron salt complexes.

In an embodiment, each substituted phenyl group which can be utilized as $R^6$ and/or $R^7$ of the pyridine bisimines and the pyridine bisimine iron salt complexes independently can be a substituted phenyl group comprising a substituent at the 2-position, a substituted phenyl group comprising a substituent at the 3-position, a substituted phenyl group comprising a substituent at the 4-position, a substituted phenyl group comprising substituents at the 2- and 3-positions, a substituted phenyl group comprising substituents at the 2- and 4-positions, a substituted phenyl group comprising substituents at the 2- and 5-positions, a substituted phenyl group comprising substituents at the 3- and 5-positions, a substituted phenyl group comprising substituents at the 2- and 6-positions, or a substituted phenyl group comprising substituents at the 2-, 4-, and 6-positions; alternatively, a substituted phenyl group comprising a substituent at the 2-position, a substituted phenyl group comprising a substituent at the 4-position, a substituted phenyl group comprising substituents at the 2- and 4-positions, a substituted phenyl group comprising substituents at the 2- and 6-positions, or a substituted phenyl group comprising substituents at the 2-, 4-, and 6-position; alternatively, a substituted phenyl group comprising substituents at the 2- and 6-positions or a substituted phenyl group comprising substituents at the 2-, 4-, and 6-positions; alternatively, a substituted phenyl group comprising a substituent at the 2-position; alternatively, a substituted phenyl group comprising a substituent at the 3-position; alternatively, a substituted phenyl group comprising a substituent at the 4-position; alternatively, a substituted phenyl group comprising substituents at the 2- and 3-positions; alternatively, a substituted phenyl group comprising substituents at the 2- and 4-positions; alternatively, a substituted phenyl group comprising substituents at the 2- and 5-positions; alternatively, a substituted phenyl group comprising substituents at the 3- and 5-positions; alternatively, a substituted phenyl group comprising substituents at the 2- and 6-position; or alternatively, a substituted phenyl group comprising substituents at the 2-, 4-, and 6-positions. In some embodiments, each substituted phenyl group which can be utilized as $R^6$ and/or $R^7$ of the pyridine bisimines and the pyridine bisimine iron salt complexes independently can be selected such that (1) one, or two of the 2- and 6-positions of the $R^6$ and $R^7$ phenyl groups and/or substituted phenyl groups independently can be a halogen, a primary carbon atom group, or a secondary carbon atom group and the remainder of the positions of the $R^6$ and $R^7$ phenyl groups and/or substituted phenyl groups can be hydrogen, (2) one of the 2- and 6-positions of the $R^6$ and $R^7$ phenyl groups and/or substituted phenyl groups can be a tertiary carbon atom group, none, one, or two of the 2- and 6-positions of the $R^6$ and $R^7$ phenyl groups and/or substituted phenyl groups independently can be a halogen, a primary carbon atom group or a secondary carbon atom group, and the remainder of the positions of the $R^6$ and/or $R^7$ phenyl groups and/or substituted phenyl groups can be hydrogen, (3) two of the 2- and 6-positions of the $R^6$ and $R^7$ phenyl groups and/or substituted phenyl groups can be a tertiary carbon atom group, none, or one of the 2- and 6-positions of the $R^6$ and $R^7$ phenyl groups and/or substituted phenyl groups independently can be a halogen, a primary carbon atom group, or a secondary carbon atom group, and the remainder of the positions of the $R^6$ and $R^7$ phenyl groups and/or substituted phenyl groups can be hydrogen, (4) one or two of the 2- and 6-positions of the $R^6$ and $R^7$ phenyl groups and/or substituted phenyl groups can be a tertiary carbon atom group and the remainder of the 2- and 6-positions of the $R^6$ and $R^7$ phenyl groups and/or substituted phenyl groups can be hydrogen, 5) one or two of the 2- and 6-positions of the $R^6$ and $R^7$ phenyl groups and/or substituted phenyl groups can be a quaternary carbon atom group and the remainder of the 2- and 6-positions of the $R^6$ and $R^7$ phenyl groups and/or substituted phenyl groups can be hydrogen, or 6) all four of the 2- and 6-positions of the $R^6$ and $R^7$ substituted phenyl groups can be fluorine. Each substituent of a substituted aryl group (general or specific) or a substituted phenyl group (general or specific) which can be utilized as $R^6$ and/or $R^7$ can be a halide, an alkyl group, or a hydrocarboxy group; alternatively, a halide or an alkyl group; alternatively, a halide and a hydrocarboxy group; alternatively, an alkyl group or a hydrocarboxy group; alternatively, a halide; alternatively, an alkyl group; or alternatively, a hydrocarboxy group. Halides, alkyl groups (general and specific), and hydrocarboxy groups (general and specific) that can be utilized as substituents are independently disclosed herein and can be utilized without limitation, and in any combination, to further describe $R^6$ and/or $R^7$ of the pyridine bisimines and the pyridine bisimine iron salt complexes. Further, one having ordinary skill in the art can recognize the independently described substituted phenyl group(s) which meet the criteria for a substituted phenyl groups (e.g., primary, secondary, tertiary, and quaternary carbon atom groups, among other criteria) and choose the appropriate substituted phenyl group(s) to meet any particular criteria for a substituted phenyl group(s) for a pyridine bisimine and/or a pyridine bisimine iron salt described herein.

In an embodiment, each substituted phenyl group which can be utilized as $R^6$ and/or $R^7$ of the pyridine bisimines and the pyridine bisimine iron salt complexes independently can be a 2-substituted phenyl group, a 3-substituted phenyl group, a 4-substituted phenyl group, a 2,3-disubstituted phenyl group, a 2,4-disubstituted phenyl group, a 2,5-disubstituted phenyl group, a 3,5-disubstituted phenyl group, a 2,6-disubstituted phenyl group, or a 2,4,6-trisubstituted phenyl group; alternatively, a 2-substituted phenyl group, a 4-substituted phenyl group, a 2,4-disubstituted phenyl group, a 2,6-disubstituted phenyl group, or a 2,4,6-trisubstituted phenyl group; alternatively, a 2,6-disubstituted phenyl group, or a 2,4,6-trisubstituted phenyl group; alternatively, a 2-substituted phenyl group; alternatively, a 4-substituted phenyl group; alternatively, a 2,3-disubstituted phenyl group; alternatively, a 2,4-disubstituted phenyl group; alternatively, a 2,5-disubstituted phenyl group; alternatively, a 3,5-disubstituted phenyl group; alternatively, a 2,6-disubstituted phenyl group; or alternatively, a 2,4,6-trisubstituted phenyl group. In some embodiments, each substituted phenyl group which can be utilized as $R^6$ and/or $R^7$ of the pyridine bisimines and the pyridine bisimine iron salt complexes independently can be selected such that (1) one, two, or three of the 2- and 6-positions of the $R^6$ and $R^7$ phenyl groups and/or substituted phenyl groups independently can be a halogen, a primary carbon atom group, or a secondary carbon atom group and the remainder of the 2- and 6-positions of the $R^6$ and $R^7$ phenyl groups and/or substituted phenyl groups can be hydrogen, (2) one of the 2- and 6-positions of the $R^6$ and $R^7$ phenyl groups and/or substituted phenyl groups can be a tertiary carbon atom group, none, one, or two of the 2- and 6-positions of the $R^6$ and $R^7$ phenyl groups and/or substituted phenyl groups independently can be a halogen, a primary carbon atom group or a secondary carbon atom group, and the remainder of the 2- and 6-positions of the $R^6$ and $R^7$ phenyl groups and/or substituted phenyl groups can be hydrogen, (3) two of the 2- and 6-positions of the $R^6$ and $R^7$ phenyl groups and/or substituted phenyl groups can be a tertiary carbon atom group, none, or one of the 2- and 6-positions of the $R^6$ and $R^7$ phenyl groups and/or substituted phenyl groups independently can be a halogen, a primary carbon atom group, or a secondary carbon atom group, and the remainder of the 2- and 6-positions of the $R^6$ and $R^7$ phenyl groups and/or substituted phenyl groups can be hydrogen, (4) one or two of the 2- and 6-positions of the $R^6$ and $R^7$ phenyl groups and/or substituted phenyl groups can be a tertiary carbon atom group and the remainder of the 2- and 6-positions of the $R^6$ and $R^7$ phenyl groups and/or substituted phenyl groups can be hydrogen, 5) one or two of the 2- and 6-positions of the $R^6$ and $R^7$ phenyl groups and/or substituted phenyl groups can be a quaternary carbon atom group and the remainder of the 2- and 6-positions of the $R^6$ and $R^7$ phenyl groups and/or substituted phenyl groups can be hydrogen, or 6) all four of the 2- and 6-positions of the $R^6$ and $R^7$ substituted phenyl groups can be fluorine. Each substituent of a substituted aryl group (general or specific) or a substituted phenyl group (general or specific) which can be utilized as $R^6$ and/or $R^7$ can be a halide, an alkyl group, or a hydrocarboxy group; alternatively, a halide or an alkyl group; alternatively, a halide and a hydrocarboxy group; alternatively, an alkyl group or a hydrocarboxy group; alternatively, a halide; alternatively, an alkyl group; or alternatively, a hydrocarboxy group. Halides, alkyl groups (general and specific), and hydrocarboxy groups (general and specific) that can be utilized as substituents are independently disclosed herein and can be utilized without limitation, and in any combination, to further describe $R^6$ and/or $R^7$ of the pyridine bisimines and the pyridine bisimine iron salt complexes. Further, one having ordinary skill in the art can recognize the independently described substituted phenyl group(s) which meet the criteria for a substituted phenyl groups (e.g., primary, secondary, tertiary, and quaternary carbon atom groups, among other criteria) and choose the appropriate substituted phenyl group(s) to meet any particular criteria for a substituted phenyl group(s) for a pyridine bisimine and/or a pyridine bisimine iron salt described herein.

In an embodiment, $R^6$ and/or $R^7$ of the pyridine bisimines and the pyridine bisimine iron salt complexes independently can a phenyl group, a 2-methylphenyl group, a 2-ethylphenyl group, a 2-isopropylphenyl group, a 2-tert-butylphenyl group, a 2-(phenyl)phenyl group, a 2-trifluoromethylphenyl group, a 2-fluorophenyl group, a 2-methoxyphenyl group, a 4-methylphenyl group, a 4-ethylphenyl group, a 4-isopropylphenyl group, a 4-tert-butylphenyl group, a 4-fluorophenyl group, a 4-trifluoromethylphenyl group, a 4-methoxyphenyl group, a 2,3-dimethyl phenyl group, 2-fluoro-3-methylphenyl group, a 2,4-dimethylphenyl group, a 2,4-diethylphenyl group, a 2,4-diisopropylphenyl group, a 2,4-di-tert-butylphenyl group, a 2-fluoro-4-methylphenyl group, a 2,5-dimethylphenyl group, a 2,6-dimethylphenyl group, a 2,6-diethylphenyl group, a 2,6-diisopropylphenylgroup, a 2,6-diphenylphenyl group, a 2-fluoro-6-methylphenyl group, a 2,6-bis(trifluoromethyl)phenyl group, a 2,6-difluorophenyl group, a 3,5-dimethylphenyl group, a 3,5-diethylphenyl group, a 3,5-diisopropylphenyl group, a 3,5-di-tert-butylphenyl group, a 3,5-di(trifluoromethyl)phenyl group, or a 2,4,6-trimethylphenyl group. In some embodiments, $R^6$ and/or $R^7$ of the pyridine bisimines and the pyridine bisimine iron salt complexes independently can be selected such that (1) one, two, or three of the 2- and 6-positions of the $R^6$ and $R^7$ phenyl groups and/or substituted phenyl groups independently can be a halogen, a primary carbon atom group, or a secondary carbon atom group and the remainder of the 2- and 6-positions of the $R^6$ and $R^7$ phenyl groups and/or substituted phenyl groups can be hydrogen, (2) one of the 2- and 6-positions of the $R^6$ and $R^7$ phenyl groups and/or substituted phenyl groups can be a tertiary carbon atom group, none, one, or two of the 2- and 6-positions of the $R^6$ and $R^7$ phenyl groups and/or substituted phenyl groups independently can be a halogen, a primary carbon atom group or a secondary carbon atom group, and the remainder of the 2- and 6-positions of the $R^6$ and $R^7$ phenyl groups and/or substituted phenyl groups can be hydrogen, (3) two of the 2- and 6- positions of the $R^6$ and $R^7$ phenyl groups and/or substituted phenyl groups can be a tertiary carbon atom group, none, or one of the 2- and 6-positions of the $R^6$ and $R^7$ phenyl groups and/or substituted phenyl groups independently can be a halogen, a primary carbon atom group, or a secondary carbon atom group, and the remainder of the 2- and 6-positions of the $R^6$ and $R^7$ phenyl groups and/or substituted phenyl groups can be hydrogen, (4) one or two of the 2- and 6-positions of the $R^6$ and $R^7$ phenyl groups can be a tertiary carbon atom group and the remainder of the 2- and 6-positions of the $R^6$ and $R^7$ phenyl groups and/or substituted phenyl groups can be hydrogen, 5) one or two of the 2- and 6-positions of the $R^6$ and $R^7$ phenyl groups and/or substituted phenyl groups can be a quaternary carbon atom group and the remainder of the 2- and 6-positions of the $R^6$ and $R^7$ phenyl groups and/or substituted phenyl groups can be hydrogen, or 6) all four of the 2- and 6-positions of the $R^6$ and $R^7$ substituted phenyl groups can be fluorine. One having ordinary skill in the art can recognize the independently described substituted phenyl group(s) which meet the criteria for a substituted phenyl groups (e.g., primary, secondary, and tertiary carbon atom groups, among other criteria) and choose the appropriate substituted phenyl group(s) to meet any particular criteria for a substituted phenyl group(s) for a pyridine bisimine and/or a pyridine bisimine iron salt described herein.

In an aspect, the pyridine bisimine can comprise, consist essentially of, or can be, a 2,6-bis[(arylimine)hydrocarbyl]pyridine, a bis[(substituted arylimine)hydrocarbyl]pyridine, or a [(arylimine)hydrocarbyl], [(substituted arylimine)hydrocarbyl]pyridine; alternatively, a 2,6-bis[(arylimine)hydrocarbyl]pyridine; alternatively, a bis[(substituted arylimine)hydrocarbyl]pyridine; or alternatively, a [(arylimine)hydrocarbyl], [(substituted arylimine)hydrocarbyl]pyridine. In an aspect, the pyridine bisimine iron salt complex can comprise, consist essentially of, or can be, a 2,6-bis[(arylimine)hydrocarbyl]pyridine iron salt complex, bis[(substituted arylimine)hydrocarbyl]pyridine iron salt complex, or a [(arylimine)hydrocarbyl], [(substituted arylimine)hydrocarbyl]pyridine iron salt complex; alternatively, a 2,6-bis[(arylimine)hydrocarbyl]pyridine iron salt complex; alternatively, a bis[(substituted arylimine)hydrocarbyl]pyridine iron salt complex; or alternatively, a [(arylimine)hydrocarbyl], [(substituted arylimine)hydrocarbyl]pyridine iron salt complex. In some embodiments, the aryl groups of the 2,6-bis[(arylimine)hydrocarbyl]pyridine or the 2,6-bis[(arylimine)hydrocarbyl]pyridine iron salt complex can be the same or can be different; alternatively, the same; or alternatively, different. In some embodiments, the substituted aryl groups of the 2,6-bis[(substituted arylimine)hydrocarbyl]pyridine or the 2,6-bis[(substituted arylimine)hydrocarbyl]pyridine iron salt complex can be the same or can be different; alternatively, the same; or alternatively, different. In an embodiment, the pyridine bisimine or the pyridine bisimine of the pyridine bisimine iron salt complex can comprise, consist essentially of, or can be, 2,6-bis[(arylimine)hydrocarbyl]pyridine, a bis[(substituted arylimine)hydrocarbyl]pyridine, and/or a [(arylimine)hydrocarbyl], [(substituted arylimine)hydrocarbyl]pyridine wherein 1) one, two, or three of the aryl groups and/or substituted aryl groups positions ortho to the carbon atom attached to the imine nitrogen independently can be a halogen, a primary carbon atom group, or a secondary carbon atom group and the remainder of the aryl groups and/or substituted aryl groups positions ortho to the carbon atom attached to the imine nitrogen can be hydrogen, 2) one of the aryl groups and/or substituted aryl groups positions ortho to the carbon atom attached to the imine nitrogen can be a tertiary carbon atom group, none, one, or two of the aryl groups and/or substituted aryl groups positions ortho to the carbon atom attached to the imine nitrogen independently can be a halogen, a primary carbon atom group or a secondary carbon atom group, and the remainder of the aryl groups and/or substituted aryl groups positions ortho to the carbon atom attached to the imine nitrogen can be hydrogen, 3) two of the aryl groups and/or substituted aryl groups positions ortho to the carbon atom attached to the imine nitrogen independently can be a tertiary carbon atom group, none, or one of the aryl groups and/or substituted aryl groups positions ortho to the carbon atom attached to the imine nitrogen independently can be a halogen, a primary carbon atom group, or a secondary carbon atom group, and the remainder of the aryl groups and/or substituted aryl groups positions ortho to the carbon atom attached to the imine nitrogen can be hydrogen, 4) one or two of the aryl groups and/or substituted aryl groups positions ortho to the carbon atom attached to the imine nitrogen independently are a tertiary carbon atom group(s) and the remainder of the aryl groups and/or substituted aryl groups positions ortho to the carbon atom attached to the imine nitrogen can be hydrogen, 5) one or two of the aryl groups and/or substituted aryl groups positions ortho to the carbon atom attached to the imine nitrogen can be a quaternary carbon atom group and the remainder of the aryl groups and/or substituted aryl groups positions ortho to the carbon atom attached to the imine nitrogen can be hydrogen, or 6) all four of the substituted aryl groups positions ortho to the carbon atom attached to the imine nitrogen are fluorine. Hydrocarbyl groups (general and specific), aryl groups (general and specific), and substituted aryl groups (general and specific) are independently described herein. The independent descriptions of the hydrocarbyl group, aryl groups, and substituted aryl groups can be utilized without limitation, an in any combination, to further describe the 2,6-bis[(arylimine)hydrocarbyl]pyridine, the bis[(substituted arylimine)hydrocarbyl]pyridine, or the [(arylimine)hydrocarbyl], [(substituted arylimine)-hydrocarbyl]pyridine which can be utilized as the pyridine bisimine or the pyridine bisimine iron salt complex that can be utilized in the processes described herein. One having ordinary skill in the art can recognize the independently described aryl group(s) and/or substituted aryl group(s) which meet the criteria for aryl group and/or substituted aryl groups (e.g., primary, secondary, and tertiary carbon atom groups, among other criteria) and choose the appropriate aryl group(s) and/or substituted aryl group(s) to meet any particular criteria for the aryl group(s) and/or substituted phenyl group(s) for a pyridine bisimine and/or a pyridine bisimine iron salt complex described herein. Further, the iron salt, $FeX_n$, is independently described herein can be combined, without limitation, with the independently described aryl group(s) and substituted aryl group(s) to further describe the appropriate pyridine bisimine iron salt complexes which can be utilized in the processes described herein.

In an embodiment, the pyridine bisimine and/or the pyridine bisimine of the pyridine bisimine iron salt complex can be 2,6-bis[(phenylimine) methyl]pyridine, 2,6-bis[(2-methylphenylimine)methyl]-pyridine, 2,6-bis[(2-ethylphenylimine)methyl]pyridine, 2,6-bis[(2-isopropylphenylimine)methyl]pyridine, 2,6-bis[(2,4-dimethylphenylimine)methyl]pyridine, 2,6-bis[(2,6-diethylphenylimine)methyl]pyridine, 2-[(2,4,6-trimethylphenylimine)methyl]-6-[(4-methylphenylimine)methyl]pyridine, 2-[(2,4,6-trimethyl-phenylimine)methyl]-6-[(3,5-dimethylphenylimine)methyl]pyridine, or 2-[(2,4,6-trimethylphenylimine)-methyl]-6-[(4-t-butylphenylimine)methyl]pyridine. The iron salt, $FeX_n$, is independently described herein can be combined, without limitation, with the pyridine bisimine(s) to further describe the appropriate pyridine bisimine iron salt complexes which can be utilized in the processes described herein.

Additional descriptions of pyridine bisimine iron salt complexes suitable for use in the present disclosure can be found in U.S. Pat. Nos. 5,955,555, 6,103,946, 6,291,733, 6,489,497, 6,451,939, 6,455,660, 6,458,739, 6,472,341, 6,545,108, 6,559,091, 6,657,026, 6,683,187, 6,710,006, 6,911,505, 6,911,506, 7,001,964, 7,045,632, 7,056,997, 7,223,893, 7,456,284, 7,683,149, 7,902,415, 7,994,376 and EP 1229020A1.

Generally, the iron salt or the iron salt of the pyridine bisimine iron salt complex can have the formula $FeX_n$. Within the formula of the iron salt having the formula $FeX_n$, X represents a monoanionic specie, and n represent the number of monoanionic species (or the iron oxidation state). Generally, the monoanionic specie, X, and the number of anionic species (or the iron oxidation state), n, are independent elements of the iron salt and are independently described herein. The iron salt having the formula $FeX_n$ can be described utilizing any aspect or embodiment of the monoanionic specie described herein, and any aspect and/or embodiment of the number of monoanionic species (or iron oxidation state) described herein.

Generally, the number of monoanionic species (or the iron oxidation state) of the iron salt or the iron salt of the pyridine bisimine iron salt complex can be any positive value that corresponds to an oxidation state available to an iron atom. In an embodiment, the number of monoanionic species, n, of the iron salt or the iron salt of the pyridine bisimine iron salt complex can be 1, 2 or 3; alternatively, 2 or 3; alternatively, 1; alternatively, 2; or alternatively, 3.

Generally, the monoanionic specie, X, of the iron salt or the iron salt of the pyridine bisimine iron salt complex can be any monoanionic specie. In an embodiment, the monoanionic specie, X, can be a halide, a carboxylate, a β-diketonate, a hydrocarboxide, a nitrate, or a chlorate. In some embodiments, the monoanionic specie, X, of the iron salt or the iron salt of the pyridine bisimine iron salt complex can be a halide, a carboxylate, a β-diketonate, or a hydrocarboxide; or alternatively, a halide, a carboxylate, or a β-diketonate. In any aspect and/or embodiment, the hydrocarboxide can be an alkoxide, an aryloxide, or an aralkoxide. Generally, hydrocarboxide (and subdivisions of hydrocarboxide) are the anion analogues of the hydrocarboxy group. In other embodiments, the monoanionic specie, X, of the iron salt or the iron salt of the pyridine bisimine iron salt complex can be a halide, a carboxylate, a β-diketonate, or an alkoxide. In other embodiments, the monoanionic specie, X, of the iron salt or the iron salt of the pyridine bisimine iron salt complex can be a halide; alternatively, a carboxylate; alternatively, a β-diketonate; alternatively, a hydrocarboxide; alternatively, an alkoxide; or alternatively, an aryloxide.

Generally, each halide monoanionic specie, X, of the iron salt or the iron salt of the pyridine bisimine iron salt complex independently can be fluorine, chlorine, bromine, or iodine; or alternatively, chlorine, bromine, or iodine. In an embodiment, each halide monoanionic specie, X, of the iron salt or the iron salt of the pyridine bisimine iron salt complex can be chlorine; alternatively, bromine; or alternatively, iodine.

Generally, each carboxylate monoanionic specie, X, of the iron salt or the iron salt of the pyridine bisimine iron salt complex can be a $C_1$ to $C_{20}$ carboxylate; or alternatively, a $C_1$ to $C_{10}$ carboxylate. In an embodiment, each carboxylate of the iron salt or the iron salt of the pyridine bisimine iron salt complex independently can be acetate, a propionate, a butyrate, a pentanoate, a hexanoate, a heptanoate, an octanoate, a nonanoate, a decanoate, an undecanoate, or a dodecanoate; or alternatively, a pentanoate, a hexanoate, a heptanoate, an octanoate, a nonanoate, or a decanoate. In some embodiments, each carboxylate monoanionic specie, X, of the iron salt or the iron salt of the pyridine bisimine iron salt complex independently can be acetate, propionate, n-butyrate, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, or laurate (n-dodecanoate); alternatively, valerate (n-pentanoate), neo-pentanoate, capronate (n-hexanoate), n-heptanoate, caprylate (n-octanoate), 2-ethylhexanoate, n-nonanoate, or caprate (n-decanoate; alternatively, n-heptanoate; alternatively, caprylate (n-octanoate); or alternatively, 2-ethylhexanoate. In some embodiments, the carboxylate can be triflate (trifluoroacetate).

Generally, each β-diketonate monoanionic specie, X, of the iron salt or the iron salt of the pyridine bisimine iron salt complex can be a $C_1$ to $C_{20}$ a β-diketonate; or alternatively, a $C_1$ to $C_{10}$ β-diketonate. In an embodiment, each β-diketonate monoanionic specie, X, of the iron salt or the iron salt of the pyridine bisimine iron salt complex independently can be acetylacetonate (i.e., 2,4-pentanedionate), hexafluoroacetylacetonate (i.e., 1,1,1,5,5,5-hexafluoro-2,4-pentanedionate), or benzoylacetonate; alternatively, acetylacetonate; alternatively, hexafluoroacetylacetone; or alternatively, benzoylacetonate.

Generally, each hydrocarboxide monoanionic specie, X, of the iron salt or the iron salt of the pyridine bisimine iron salt complex can be any $C_1$ to $C_{20}$ hydrocarboxide; or alternatively, any $C_1$ to $C_{10}$ hydrocarboxide. In an embodiment, each hydrocarboxide monoanionic specie, X, of the iron salt or the iron salt of the pyridine bisimine iron salt complex can be a $C_1$ to $C_{20}$ alkoxide; alternatively, a $C_1$ to $C_{10}$ alkoxide; alternatively, a $C_6$ to $C_{20}$ aryloxide; or alternatively, a $C_6$ to $C_{10}$ aryloxide. In an embodiment, each alkoxide monoanionic specie, X, of the iron salt or the iron salt of the pyridine bisimine iron salt complex independently can be methoxide, ethoxide, a propoxide, or a butoxide. In some embodiments, each alkoxide monoanionic specie, X, of the iron salt or the iron salt of the pyridine bisimine iron salt complex independently can be methoxide, ethoxide, isopropoxide, or tert-butoxide; alternatively, methoxide; alternatively, an ethoxide; alternatively, an iso-propoxide; or alternatively, a tert-butoxide. In an aspect, each aryloxide monoanionic specie, X, of the iron salt or the iron salt of the pyridine bisimine iron salt complex independently can be phenoxide.

In an embodiment, the iron salt or the iron salt of the pyridine bisimine iron salt complex can comprise, or consist essentially of, or can be an iron halide, an iron acetylacetonate, an iron carboxylate, or any combination thereof. In some embodiments, the iron salt or the iron salt of the pyridine bisimine iron salt complex can comprise, consist essentially of, or can be, iron(II) fluoride, iron(III) fluoride, iron(II) bromide, iron(III) bromide, iron(II) iodide, iron(III) iodide, iron(II) acetate, iron(III) acetate, iron(II) acetylacetonate, iron(III) acetylacetonate, iron(II) 2-ethylhexanoate, iron(III) 2-ethylhexanoate, iron(II) triflate, iron(III) triflate, iron(II) nitrate, iron(III) nitrate, or any combination thereof;

alternatively, iron(II) chloride, iron(III) chloride, iron(II) acetate, iron(III) acetate, iron(II) acetylacetonate, iron(III) acetylacetonate, or any combination thereof; alternatively, iron(II) chloride, iron(III) chloride, iron(II) acetylacetonate, iron(III) acetylacetonate, or any combination thereof; alternatively, iron(II) chloride; alternatively, iron(III) chloride; or alternatively, iron(II) acetylacetonate.

In an embodiment, the pyridine bisimine iron salt complex can be selected from the group consisting of a 2,6-bis[(phenylimine) methyl]pyridine iron salt complex, a 2,6-bis[(2-methylphenylimine)methyl]pyridine iron salt complex, a 2,6-bis[(2-ethylphenylimine)methyl]pyridine iron salt complex, a 2,6-bis[(2-isopropylphenylimine)methyl]pyridine iron salt complex, a 2,6-bis[(2,4-dimethylphenylimine) methyl]pyridine, a 2-[(2,4,6-trimethylphenylimine)methyl]-6-[(4-methylphenyl-imine)methyl]pyridine iron salt complex, a 2-[(2,4,6-trimethylphenylimine)methyl]-6-[(3,5-dimethyl-phenylimine)methyl]pyridine iron salt complex, and a 2-[(2,4,6-trimethylphenylimine)methyl]-6-[(4-t-butylphenylimine)methyl]pyridine iron salt complex. In another embodiment, the pyridine bisimine iron salt complex can be selected from the group consisting of a 2,6-bis[(phenylimine) methyl]pyridine iron dichloride complex, a 2,6-bis[(2-methylphenylimine)methyl]pyridine iron dichloride complex, a 2,6-bis[(2-ethylphenylimine)methyl]pyridine iron dichloride complex, a 2,6-bis[(2-isopropylphenylimine)-methyl]pyridine iron dichloride complex, a 2,6-bis[(2,4-dimethylphenylimine)methyl]pyridine, a 2-[(2,4,6-trimethylphenylimine)methyl]-6-[(4-methylphenylimine) methyl]pyridine iron dichloride complex, a 2-[(2,4,6-trimethylphenylimine)methyl]-6-[(3,5-dimethylphenylimine)methyl]pyridine iron dichloride complex, and a 2-[(2,4,6-trimethylphenylimine)methyl]-6-[(4-t-butylphenylimine)methyl]pyridine iron dichloride complex. In another embodiment, the pyridine bisimine iron salt complex can be selected from the group consisting of a 2,6-bis[(phenylimine) methyl]pyridine iron diacetylacetonate complex, a 2,6-bis[(2-methylphenylimine)methyl]pyridine iron diacetylacetonate complex, a 2,6-bis[(2-ethylphenylimine)methyl]pyridine iron diacetylacetonate complex, a 2,6-bis[(2-isopropylphenylimine)methyl]pyridine iron diacetylacetonate complex, a 2,6-bis[(2,4-dimethylphenylimine)methyl]pyridine, a 2-[(2,4,6-trimethylphenylimine)methyl]-6-[(4-methylphenyl-imine)methyl]pyridine iron diacetylacetonate complex, a 2-[(2,4,6-trimethylphenylimine)methyl]-6-[(3,5-dimethylphenylimine)methyl] pyridine iron diacetylacetonate complex, and a 2-[(2,4,6-trimethyl-phenylimine)methyl]-6-[(4-t-butylphenylimine) methyl]pyridine iron diacetylacetonate complex.

It should be noted that while not explicitly shown or stated, the iron salts and/or the pyridine bisimine iron salt complexes can further comprise a neutral ligand. While the non-pyridine bisimine neutral ligand for the iron salts or the pyridine bisimine iron salt complexes are not shown in the structure or the formulas provided herein, it should be understood that the iron salts and/or the pyridine bisimine iron salt complexes depictions do not limit the iron salts or the pyridine bisimine iron salt complexes to those not having a non-pyridine bisimine neutral ligand. In fact the iron salts or the pyridine bisimine iron salt complexes which can be utilized in any aspect disclosed herein or any embodiment disclosed herein can include a non-pyridine bisimine neutral ligand and that these depictions provided herein do not limit iron complexes to those which do not comprise a non-pyridine bisimine neutral ligand regardless of the language utilized to describe the iron complexes. Non-pyridine bisimine neutral ligands are provided herein and can be utilized without limitation to further describe the iron salts and/or the pyridine bisimine iron salt complexes.

Generally, the neutral ligand, if present, can be any neutral ligand that forms an isolatable compound with the iron salt or the pyridine bisimine iron salt complex. In an aspect, each neutral ligand independently can be a nitrile, an ether, or an amine; alternatively, a nitrile; alternatively, an ether; or alternatively, an amine. The number of neutral ligands of the iron salt or the pyridine bisimine iron salt complex can be any number that forms an isolatable compound with the iron salts or the pyridine bisimine iron salt complexes. In an embodiment, the number of neutral ligands, if the iron salt or the pyridine bisimine iron salt complex has non-pyridine bisimine neutral ligands, can be 1, 2, 3, 4, 5, or 6; alternatively, 1; alternatively, 2; alternatively, 3; alternatively, 4; alternatively, 5; or alternatively, 6.

Generally, each nitrile ligand which can be utilized as the non-pyridine bisimine neutral ligand independently can be a $C_2$ to $C_{20}$ nitrile; or alternatively, a $C_2$ to $C_{10}$ nitrile. In an embodiment, each nitrile ligand independently can be a $C_2$ to $C_{20}$ aliphatic nitrile, a $C_7$ to $C_{20}$ aromatic nitrile, a $C_8$ to $C_{20}$ aralkane nitrile, or any combination thereof; alternatively, a $C_2$ to $C_{20}$ aliphatic nitrile; alternatively, a $C_7$ to $C_{20}$ aromatic nitrile; or alternatively, a $C_8$ to $C_{20}$ aralkane nitrile. In some embodiments, each nitrile ligand which can be utilized as the non-pyridine bisimine neutral ligand independently can be a $C_2$ to $C_{10}$ aliphatic nitrile, a $C_7$ to $C_{10}$ aromatic nitrile, a $C_8$ to $C_{10}$ aralkane nitrile, or any combination thereof; alternatively, a $C_1$ to $C_{10}$ aliphatic nitrile; alternatively, a $C_7$ to $C_{10}$ aromatic nitrile; or alternatively, a $C_8$ to $C_{10}$ aralkane nitrile. In an embodiment, each aliphatic nitrile which can be utilized as the non-pyridine bisimine neutral ligand independently can be acetonitrile, propionitrile, a butyronitrile, benzonitrile, or any combination thereof; alternatively, acetonitrile; alternatively, propionitrile; alternatively, a butyronitrile; or alternatively, benzonitrile.

Generally, each ether ligand which can be utilized as the non-pyridine bisimine neutral ligand independently can be a $C_2$ to $C_{40}$ ether; alternatively, a $C_2$ to $C_{30}$ ether; or alternatively, a $C_2$ to $C_{20}$ ether. In an embodiment, each ether ligand which can be utilized as the non-pyridine bisimine neutral ligand independently can be a $C_2$ to $C_{40}$ aliphatic ether, a $C_3$ to $C_{40}$ aliphatic cyclic ether, a $C_4$ to $C_{40}$ aromatic cyclic ether; alternatively, a $C_2$ to $C_{40}$ aliphatic acyclic ether or a $C_3$ to $C_{40}$ aliphatic cyclic ether; alternatively, a $C_2$ to $C_{40}$ aliphatic acyclic ether; alternatively, a $C_3$ to $C_{40}$ aliphatic cyclic ether; or alternatively, a $C_4$ to $C_{40}$ aromatic cyclic ether. In some embodiments, each ether ligand which can be utilized as the non-pyridine bisimine neutral ligand independently can be a $C_2$ to $C_{30}$ aliphatic ether, a $C_3$ to $C_{30}$ aliphatic cyclic ether, a $C_4$ to $C_{30}$ aromatic cyclic ether; alternatively, a $C_2$ to $C_{30}$ aliphatic acyclic ether or a $C_3$ to $C_{30}$ aliphatic cyclic ether; alternatively, a $C_2$ to $C_{30}$ aliphatic acyclic ether; alternatively, a $C_3$ to $C_{30}$ aliphatic cyclic ether; or alternatively, a $C_4$ to $C_{30}$ aromatic cyclic ether. In other embodiments, each ether ligand which can be utilized as the non-pyridine bisimine neutral ligand independently can be a $C_2$ to $C_{20}$ aliphatic ether, a $C_3$ to $C_{20}$ aliphatic cyclic ether, a $C_4$ to $C_{20}$ aromatic cyclic ether; alternatively, a $C_2$ to $C_{20}$ aliphatic acyclic ether or a $C_3$ to $C_{20}$ aliphatic cyclic ether; alternatively, a $C_2$ to $C_{20}$ aliphatic acyclic ether; alternatively, a $C_3$ to $C_{20}$ aliphatic cyclic ether; or alternatively, a $C_4$ to $C_{20}$ aromatic cyclic ether. In some embodiments, each ether ligand which can be utilized as the non-pyridine bisimine neutral ligand independently can be dimethyl ether, diethyl ether, a dipropyl ether, a dibutyl ether, methyl ethyl ether, a methyl propyl ether, a methyl butyl ether, tetrahydrofuran, a dihydrofuran, 1,3-dioxolane, tetrahydropyran, a dihydropyran, a pyran, a dioxane, furan, benzofuran, isobenzofuran, isobenzofuran, dibenzofuran, diphenyl ether, a ditolyl ether, or any combination thereof; alternatively, dimethyl ether, diethyl ether, a dipropyl ether, a dibutyl ether, methyl ethyl ether, a methyl propyl ether, a methyl butyl ether, or any combination thereof; tetrahydrofuran, a dihydrofuran, 1,3-dioxolane, tetrahydropyran, a dihydropyran, a pyran, a dioxane, or any combination thereof; furan, benzofuran, isobenzofuran, isobenzofuran, dibenzofuran, or any combination thereof; diphenyl ether, a ditolyl ether, or any combination thereof; alternatively, dimethyl ether; alternatively, diethyl ether; alternatively, a dipropyl ether; alternatively, a dibutyl ether; alternatively, methyl ethyl ether; alternatively, a methyl propyl ether; alternatively, a methyl butyl ether; alternatively, tetrahydrofuran; alternatively, a dihydrofuran; alternatively, 1,3-dioxolane; alternatively, tetrahydropyran; alternatively, a dihydropyran; alternatively, a pyran; alternatively, a dioxane; alternatively, furan; alternatively, benzofuran; alternatively, isobenzofuran; alternatively, isobenzofuran; alternatively, dibenzofuran; alternatively, diphenyl ether; or alternatively, a ditolyl ether.

In an embodiment, each amine which can be utilized as the non-pyridine bisimine neutral ligand independently can be a monohydrocarbylamine, a dihydrocarbylamine, or a trihydrocarbylamine, or any combination thereof; alternatively, monohydrocarbylamine; alternatively, a dihydrocarbylamine; or alternatively, a trihydrocarbylamine. Monohydrocarbylamines which can be utilized as the non-pyridine bisimine neutral ligand can be a $C_1$ to $C_{30}$, a $C_1$ to $C_{20}$, a $C_1$ to $C_{10}$, or a $C_1$ to $C_5$ monohydrocarbylamine. Dihydrocarbylamines which can be utilized as the non-pyridine bisimine neutral ligand can be a $C_2$ to $C_{30}$, a $C_2$ to $C_{20}$, a $C_2$ to $C_{10}$, or a $C_2$ to $C_5$ dihydrocarbylamine. Trihydrocarbylamines which can be utilized as the non-pyridine bisimine neutral ligand can be a $C_3$ to $C_{30}$, a $C_3$ to $C_{20}$, or a $C_3$ to $C_{10}$ dihydrocarbylamine. Hydrocarbyl groups (general and specific) are disclosed herein (e.g., as substituent groups, among other places) and can be utilized without limitation to further describe the monohydrocarbylamines, dihydrocarbylamines, and/or trihydrocarbylamines which can be utilized as the non-pyridine bisimine neutral ligand. Generally, each hydrocarbyl group of the dihydrocarbylamine (or trihydrocarbylamine) is independent of each other and can be the same: or alternatively, can be different. In a non-limiting embodiment, the monohydrocarbylamine, which can be utilized as the non-pyridine bisimine neutral ligand can be, comprise, or consist essentially of, methyl amine, ethyl amine, propyl amine, butyl amine, or any combination thereof; alternatively, methyl amine; alternatively, ethyl amine; alternatively, propyl amine; or alternatively, butyl amine. In some embodiments, the dihydrocarbylamine, which can be utilized as the non-pyridine bisimine neutral ligand can be, comprise, or consist essentially of, dimethyl amine, diethyl amine, dipropyl amine, dibutylamine, or any combination thereof; alternatively, dimethyl amine; alternatively, diethyl amine; alternatively, dipropyl amine; or alternatively, dibutylamine. In some embodiments, the trihydrocarbylamine, which can be utilized as the non-pyridine bisimine neutral ligand can be, comprise, or consist essentially of, trimethyl amine, triethyl amine, tripropyl amine, tributyl amine, or any combination thereof; alternatively, trimethyl amine; alternatively, triethyl amine; alternatively, tripropyl amine; or alternatively, tributyl amine.

In an embodiment, the organoaluminum compound which can be utilized in the processes described herein can comprise an aluminoxane, an alkylaluminum compound, or a combination thereof; alternatively, an aluminoxane; or alternatively, an alkylaluminum compound. In an embodiment, the alkylaluminum compound can be a trialkylaluminum, an alkylaluminum halide, an alkylaluminum alkoxide, or any combination thereof. In some embodiments, the alkylaluminum compound can be a trialkylaluminum, an alkylaluminum halide, or any combination thereof; alternatively, a trialkylaluminum, an alkylaluminum halide, or any combination thereof; or alternatively, a trialkylaluminum. In other embodiments, the alkylaluminum compound can be a trialkylaluminum; alternatively, an alkylaluminum halide; or alternatively, an alkylaluminum alkoxide.

In an aspect, each alkyl group of any organoaluminum compound or any alkylaluminum compound disclosed herein (e.g., trialkylaluminum, alkylaluminum halide, alkylaluminum alkoxide or aluminoxane) independently can be a $C_1$ to $C_{20}$, a $C_1$ to $C_{10}$, or a $C_1$ to $C_6$ alkyl group. In an embodiment, each alkyl group of any organoaluminum compound or any alkylaluminum compound disclosed herein (e.g., trialkylaluminum, alkylaluminum halide, alkylaluminum alkoxide, or aluminoxane) independently can be a methyl group, an ethyl group, a propyl group, a butyl group, a pentyl group, a hexyl group, a heptyl group, or an octyl group; alternatively, a methyl group, a ethyl group, a butyl group, a hexyl group, or an octyl group. In some embodiments, each alkyl group of any organoaluminum compound or any alkylaluminum compound disclosed herein (e.g., trialkylaluminum, alkylaluminum halide, alkylaluminum alkoxide, or aluminoxane) independently can be a methyl group, an ethyl group, an n-propyl group, an n-butyl group, an iso-butyl group, an n-hexyl group, or an n-octyl group; alternatively, a methyl group, an ethyl group, an n-butyl group, or an iso-butyl group; alternatively, a methyl group; alternatively, an ethyl group; alternatively, an n-propyl group; alternatively, an n-butyl group; alternatively, an iso-butyl group; alternatively, an n-hexyl group; or alternatively, an n-octyl group.

In an aspect, each halide of any alkylaluminum halide disclosed herein independently can be chloride, bromide, or iodide. In some embodiments, each halide of any alkylaluminum halide disclosed herein can be chloride or bromide; or alternatively, or chloride.

In an aspect, each alkoxide group of any alkylaluminum alkoxide disclosed herein independently can be a $C_1$ to Cm, a $C_1$ to $C_{10}$, or a $C_1$ to $C_6$ alkoxy group. In an embodiment, each alkoxide group of any alkylaluminum alkoxide disclosed herein independently can be a methoxy group, an ethoxy group, a propoxy group, a butoxy group, a pentoxy group, a hexoxy group, a heptoxy group, or an octoxy group; alternatively, a methoxy group, a ethoxy group, a butoxy group, a hexoxy group, or an octoxy group. In some embodiments, each alkoxide group of any alkylaluminum alkoxide disclosed herein independently can be a methoxy group, an ethoxy group, an n-propoxy group, an n-butoxy group, an iso-butoxy group, an n-hexoxy group, or an n-octoxy group; alternatively, a methoxy group, an ethoxy group, an n-butoxy group, or an iso-butoxy group; alternatively, a methoxy group; alternatively, an ethoxy group; alternatively, an n-propoxy group; alternatively, an n-butoxy group; alternatively, an iso-butoxy group; alternatively, an n-hexoxy group; or alternatively, an n-octoxy group.

In a non-limiting embodiment, the trialkylaluminum compound can comprise, can consist essentially of, or can be, trimethylaluminum, triethylaluminum, tripropylaluminum, tributylaluminum, trihexylaluminum, trioctylaluminum, or mixtures thereof. In some non-limiting embodiments, the trialkylaluminum compound comprise, can consist essentially of, or can be, trimethylaluminum, triethylaluminum, tripropylaluminum, tri-n-butylaluminum, tri-isobutylaluminum, trihexylaluminum, tri-n-octylaluminum, or mixtures thereof; alternatively, triethylaluminum, tri-n-butylaluminum, tri-isobutylaluminum, trihexylaluminum, tri-n-octylaluminum, or mixtures thereof; alternatively, triethylaluminum, tri-n-butylaluminum, trihexylaluminum, tri-n-octylaluminum, or mixtures thereof. In other non-limiting embodiments, the trialkylaluminum compound can comprise, can consist essentially of, or can be, trimethylaluminum; alternatively, triethylaluminum; alternatively, tripropylaluminum; alternatively, tri-n-butylaluminum; alternatively, tri-isobutylaluminum; alternatively, trihexylaluminum; or alternatively, tri-n-octylaluminum.

In a non-limiting embodiment, the alkylaluminum halide can comprise, can consist essentially of, or can be, diethylaluminum chloride, diethylaluminum bromide, ethylaluminum dichloride, ethylaluminum sesquichloride, and mixtures thereof. In some non-limiting embodiments, the alkylaluminum halide can comprise, can consist essentially of, or can be diethylaluminum chloride, ethylaluminum dichloride, ethylaluminum sesquichloride, and mixtures thereof; or alternatively, diethylaluminum chloride; alternatively, diethylaluminum bromide; alternatively, ethylaluminum dichloride; or alternatively, ethylaluminum sesquichloride.

In a non-limiting embodiment, the aluminoxane can have a repeating unit characterized by the Formula I:

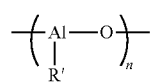

Formula I wherein R' is a linear or branched alkyl group. Alkyl groups for organoaluminum compounds are independently described herein and can be utilized without limitation to further describe the aluminoxanes having Formula I. Generally, n of Formula I is greater than 1; or alternatively, greater than 2. In an embodiment, n can range from 2 to 15; or alternatively, range from 3 to 10.

In a non-limiting embodiment, the aluminoxane can comprise, can consist essentially of, or can be, methylaluminoxane (MAO), ethylaluminoxane, modified methylaluminoxane (MMAO), n-propylaluminoxane, iso-propylaluminoxane, n-butylaluminoxane, sec-butylaluminoxane, iso-butylaluminoxane, t-butylaluminoxane, 1-pentyl-aluminoxane, 2-entylaluminoxane, 3-pentyl-aluminoxane, iso-pentyl-aluminoxane, neopentylaluminoxane, or mixtures thereof. In some non-limiting embodiments, the aluminoxane can comprise, can consist essentially of, or can be, methylaluminoxane (MAO), modified methylaluminoxane (MMAO), isobutyl aluminoxane, t-butyl aluminoxane, or mixtures thereof. In other non-limiting embodiments, the aluminoxane can be, comprise, or consist essentially of, methylaluminoxane (MAO); alternatively, ethylaluminoxane; alternatively, modified methylaluminoxane (MMAO); alternatively, n-propylaluminoxane; alternatively, iso-propyl-aluminoxane; alternatively, n-butylaluminoxane; alternatively, sec-butylaluminoxane; alternatively, iso-butylaluminoxane; alternatively, t-butyl aluminoxane; alternatively, 1-pentyl-aluminoxane; alternatively, 2-pentylaluminoxane; alternatively, 3-pentyl-aluminoxane; alternatively, iso-pentyl-aluminoxane; or alternatively, neopentyl-aluminoxane.

In an aspect, the processes described herein can utilize an organic reaction medium. Generally, the organic reaction medium can act as a solvent and/or a diluent in the processes described herein. In an embodiment, the organic reaction medium can comprise, can consist essentially of, or can be, a, at least one, or one or more, hydrocarbon(s); or alternatively, an, at least one, or one or more, aliphatic hydrocarbon(s). In some embodiments, the organic reaction medium can comprise, can consist essentially of, or can be, a saturated aliphatic hydrocarbon, an olefinic aliphatic hydrocarbon, or any combination thereof; alternatively, a, at least one, or one or more, saturated aliphatic hydrocarbon(s); or alternatively, an, at least one, or one or more, olefinic aliphatic hydrocarbon(s). General and specific hydrocarbons, aliphatic hydrocarbons, saturated aliphatic hydrocarbons, and olefinic aliphatic hydrocarbons are described herein and can be utilized without limitation as the organic reaction medium.

In an embodiment, the hydrocarbon, aliphatic hydrocarbon, saturated aliphatic hydrocarbon, or olefinic aliphatic hydrocarbon which can be utilized as the organic reaction medium can comprise, can consist essentially of, or can be, a, at least one, or one or more, $C_8$ to $C_{18}$, a $C_8$ to $C_{16}$, or a $C_{10}$ to $C_{14}$ hydrocarbon(s), aliphatic hydrocarbon, saturated aliphatic hydrocarbon, or olefinic aliphatic hydrocarbon. The, the at least one, or the one or more, hydrocarbon(s), aliphatic hydrocarbon(s), saturated aliphatic hydrocarbon(s), or olefinic aliphatic hydrocarbon(s) can be cyclic or acyclic and/or can be linear or branched, unless otherwise specified. In some embodiments, the saturated aliphatic hydrocarbon which can be utilized as the organic reaction medium can be, comprise, or consist essentially of, octane(s), decane(s), dodecane(s), tetradecane(s), hexadecane(s), octadecane(s), or any combination thereof; alternatively, decane(s), dodecane(s), tetradecane(s), or any combination thereof; alternatively, octane(s); alternatively, decane(s); alternatively, dodecane(s); alternatively, tetradecane(s) alternatively, hexadecane(s) or alternatively, octadecane(s). In an embodiment, the specific carbon numbered saturated aliphatic hydrocarbon which can be utilized as the organic reaction medium can comprise, can consist essentially of, or can be, a, at least one, or one or more, specific carbon numbered saturated aliphatic hydrocarbon(s). In an embodiment, the olefinic aliphatic hydrocarbon which can be utilized as the organic reaction medium can comprise, can consist essentially of, or can be, a, at least one, or one or more, $C_8$ to $C_{18}$, $C_8$ to $C_{16}$, or $C_{10}$ to $C_{14}$ olefinic aliphatic hydrocarbon. In some embodiments, the olefinic aliphatic hydrocarbon which can be utilized as the organic reaction medium can comprise, can consist essentially of, or can be, an, at least one, or one or more, alpha olefin(s); or alternatively, a, at least one, or one or more, normal alpha olefin(s). In a non-limiting embodiment, the olefinic aliphatic hydrocarbon which can be utilized as the organic reaction medium can be, comprise, or consist essentially of, 1-octene, 1-decene, 1-dodecene, 1-tetradecene, 1-hexadecene, 1-octadecene, or any combination thereof; alternatively, 1-decene, 1-dodecene, 1-tetradecene, or any combination thereof; alternatively, 1-decene; alternatively, 1-dodecene; or alternatively, 1-tetradecene. In an aspect the organic reaction medium can be substantially devoid of a halogenated compound. As utilized herein, an organic reaction medium substantially devoid of halogenated compounds means that the organic reaction medium can contain less than 1 wt. %, 0.9 wt. %, 0.8 wt. %, 0.7 wt. %, 0.6 wt. %, 0.5 wt. %, 0.4 wt. %, 0.3 wt. %, 0.2 wt. %, 0.1 wt. %, 0.05 wt. %, or 0.0 wt. 1% halogenated compounds based upon the weight of the organic reaction medium.

In an aspect, the oligomer product can be formed in a reaction zone. In an embodiment, the reaction zone of any process described herein can comprise a continuous stirred tank reactor, a plug flow reactor, or any combination thereof; alternatively, a continuous stirred tank reactor; or alternatively, a plug flow reactor. In an embodiment, the reaction zone of any process described herein can comprise a continuous stirred tank reactor, a loop reactor, a solution reactor, a tubular reactor, a recycle reactor, a bubble reactor, or any combination thereof; alternatively, a continuous stirred tank reactor; alternatively, a loop reactor; alternatively, a solution reactor; alternatively, a tubular reactor; alternatively, a recycle reactor; or alternatively, a bubble reactor. In some embodiments, the reaction zone in which the oligomer product can be formed can comprise multiple reactors; or alternatively, only one reactor. When multiple reactors are present, each of the reactors can be the same or can be different types of reactors. Additionally, when reaction zone can comprise more than one reactor, each reactor independently can be any reactor described herein, and the reactors can be arranged in series, parallel, or any combination thereof; alternatively, in series; or alternatively, in parallel.

It should be noted that when the reaction zone can comprise multiple reactors, each reactor can be independent of each other (regardless of whether they are operated in series or parallel). As such, the contact modes (if needed), the conditions under which the oligomer product can be formed, the oligomer product formation parameters under which the oligomer product can be formed and/or the reaction zone conditions can be different for each reactor. In particular, when reaction zone comprises multiple reactors in series, each reactor can be operated to achieve different goals. For example, a first reactor can be operated to i) contact of the ethylene and one or more the pyridine bisimine iron salt complex, the alkylaluminum compound, and the organic reaction medium, ii) initiate production of the oligomer product under a first set of conditions capable of producing the oligomer product to some intermediate ethylene conversion and the effluent of the first reactor transferred to a second reactor operated to achieve the desired ethylene conversion under a second set of conditions capable of producing the oligomer product (with or without additional ethylene and one or more the pyridine bisimine iron salt complex, the alkylaluminum compound, and the organic reaction medium being added to the reactor/reaction zone).

In any aspect or embodiment, the oligomer product can be formed at, the reaction zone can have, or the reaction zone can operate at, conditions that can comprise, either singly or in any combination, an iron of the iron salt concentration or iron of the pyridine bisimine iron salt complex concentration, a pyridine bisimine to iron salt equivalent ratio charged to the reaction zone (depending upon the catalyst system utilized), aluminum of the organoaluminum compound to the iron of the iron salt molar ratio or iron of the pyridine bisimine iron salt complex molar ratio (depending upon the catalyst system utilized), aluminum of the organoaluminum compound concentration, an ethylene partial pressure, an ethylene to organic reaction medium mass ratio, a temperature (or an average temperature), a Schulz-Flory K value, a hydrogen partial pressure, or a hydrogen to ethylene mass ratio. In an embodiment, the oligomer product can be formed at, the reaction zone can have, or the reaction zone can operate at, conditions that can comprise, either singly or in any combination, an iron of the iron salt or iron of the pyridine bisimine iron salt complex concentration (depending upon the catalyst system utilized), aluminum of the organoaluminum compound to the iron of the iron salt or iron of the pyridine bisimine iron salt complex molar ratio (depending upon the catalyst system utilized), an ethylene partial pressure, and an ethylene to organic reaction medium mass ratio; or alternatively, an iron of the iron salt or iron of the pyridine bisimine iron salt complex concentration (depending upon the catalyst system utilized), aluminum of the organoaluminum compound to the iron of the iron salt or iron of the pyridine bisimine iron salt complex molar ratio (depending upon the catalyst system utilized), an ethylene partial pressure, an ethylene to organic reaction medium mass ratio, and optionally a hydrogen partial pressure or hydrogen to ethylene mass ratio. In another embodiment, the oligomer product can be formed at, the reaction zone can have, or the reaction zone can operate at, conditions that can comprise, either singly or in any combination an iron of the iron salt or iron of the pyridine bisimine iron salt complex concentration (depending upon the catalyst system utilized); alternatively, a pyridine bisimine to iron salt equivalent ratio charged to the reaction zone; alternatively, aluminum of the organoaluminum compound to the iron of the iron salt or iron of the pyridine bisimine iron salt complex molar ratio (depending upon the catalyst system utilized); alternatively, aluminum of the organoaluminum compound concentration; alternatively, an ethylene partial pressure; alternatively, an ethylene to organic reaction medium mass ratio; alternatively, a temperature (or an average temperature); alternatively, a Schulz-Flory K value; alternatively, hydrogen partial pressure; or alternatively, a hydrogen to ethylene mass ratio.

In any aspect and/or embodiment, the oligomer product can be formed at, the reaction zone can have, or the reaction zone can operate at, a minimum iron of the iron salt or iron of the pyridine bisimine iron salt complex concentration (hereafter iron concentration or Fe concentration) of $5 \times 10^{-4}$ mmol Fe/kg, $7 \times 10^{-4}$ mmol Fe/kg, or $9 \times 10^{-4}$ mmol Fe/kg; alternatively or additionally, a maximum reaction zone iron of the iron salt or iron of the pyridine bisimine iron salt complex concentration of $5 \times 10^{-3}$ mmol Fe/kg, $4 \times 10^{-3}$ mmol Fe/kg, or $3 \times 10^{-3}$ mmol Fe/kg. In an embodiment, the oligomer product can be formed at, the reaction zone can have, or the reaction zone can operate at, an iron concentration in the range of any minimum iron concentration disclosed herein to any maximum iron concentration disclosed herein. In a non-limiting embodiment, the oligomer product can be formed at, the reaction zone can have, or the reaction zone can operate at, an iron concentration in the range of $5 \times 10^{-4}$ mmol Fe/kg to $5 \times 10^{-3}$ mmol Fe/kg, $7 \times 10^{-4}$ mmol Fe/kg to $7 \times 10^{-3}$ mmol Fe/kg, or $9 \times 10^{-4}$ mmol Fe/kg to $3 \times 10^{-3}$ mmol Fe/kg. Other iron concentration ranges that can be utilized are readily apparent to those skilled in the art with the aid of this disclosure. As utilized herein the phrases "iron of the iron salt concentration" and "iron of the pyridine bisimine iron salt complex concentration" refer to the iron concentration within a solution, stream, or vessel (e.g., reaction zone) that is attributable to the iron of the iron salt or the iron of the pyridine bisimine iron salt complex, respectively.

In any aspect and/or embodiment, the oligomer product can be formed at, the reaction zone can have, or the reaction zone can operate at, a minimum pyridine bisimine to iron salt equivalent ratio charged to the reaction zone (also referred to as a minimum pyridine bisimine to iron salt equivalent ratio) of 0.8:1, 0.9:1, or 0.95:1; alternatively or additionally, a maximum pyridine bisimine to iron salt equivalent ratio equivalent ratio charged to the reaction zone (also referred to as a maximum pyridine bisimine to iron salt equivalent ratio) of 1.2:1, 1.15, 1.1:1, or 1.05:1. In an embodiment, the oligomer product can be formed at, the reaction zone can have, or the reaction zone can operate at, a pyridine bisimine to iron salt equivalent ratio charged to the reaction zone (hereafter, a pyridine bisimine to iron salt equivalent ratio) in the range of maximum pyridine bisimine to iron salt equivalent ratio disclosed herein to any maximum pyridine bisimine to iron salt equivalent ratio disclosed herein. In a non-limiting embodiment, the pyridine bisimine to iron salt equivalent ratio can be in the range of 0.8:1 to 5:1, from 0.9:1 to 4:1, from 0.90:1 to 3:1, from 0.95:1 to 3:1, or from 0.95:1 to 2.5:1. Other pyridine bisimine to iron salt equivalent ratio ranges that can be utilized are readily apparent to those skilled in the art with the aid of this disclosure.

In any aspect and/or embodiment, the oligomer product can be formed at, the reaction zone can have, or the reaction zone can operate at, a minimum reaction zone aluminum of the organoaluminum compound to the iron of the iron salt or pyridine bisimine iron salt complex molar ratio (also referred to as minimum aluminum:iron or Al:Fe molar ratio) of 300:1, 350:1, or 400:1; alternatively or additionally, a maximum reaction zone iron of the iron salt or iron of the pyridine bisimine iron salt complex concentration (also referred to as maximum aluminum:iron or Al:Fe molar ratio) of 800:1, 700:1, 600:1, or 500:1. In an embodiment, the oligomer product can be formed, the reaction zone can have, or the reaction zone can operate, at an aluminum:iron molar ratio in the range of any minimum iron of the iron salt or iron of the pyridine bisimine iron salt complex concentration disclosed herein to any maximum iron of the iron salt or iron of the pyridine bisimine iron salt complex concentration disclosed herein. In a non-limiting embodiment, the oligomer product can be formed, the reaction zone can have, or the reaction zone can operate, at an aluminum to iron molar ratio (also referred to as aluminum:iron or Al:Fe molar ratio) in the range of 300:1 to 800:1, 350:1 to 700:1, 350:1 to 600:1, 350:1 to 500:1, 400:1 to 600:1, or 400:1 to 500:1. Other iron of the iron salt or iron of the pyridine bisimine iron salt complex concentration ranges that can be utilized are readily apparent to those skilled in the art with the aid of this disclosure.

In any aspect and/or embodiment, the oligomer product can be formed at, the reaction zone can have, or the reaction zone can operate at, a minimum aluminum of the organoaluminum compound concentration (also referred to as minimum aluminum concentration) of 0.75 mmol Al/kg, 0.9 mmol Al/kg, or 1.1 mmol Al/kg; alternatively or additionally, a maximum aluminum concentration of the organoaluminum compound concentration (also referred to as maximum aluminum concentration) of 2.6 mmol Al/kg, 2.2 mmol Al/kg, 1.8 mmol Al/kg, or 1.5 mmol Al/kg. In an embodiment, the oligomer product can be formed at, the reaction zone can have, or the reaction zone can operate at, an aluminum of the organoaluminum compound concentration also referred to as aluminum concentration) in the range of any minimum aluminum concentration disclosed herein to any maximum aluminum concentration disclosed herein. In a non-limiting embodiment, the oligomer product can be formed, the reaction zone can have, or the reaction zone can operate, at an aluminum concentration in the range of 0.75 mmol Al/kg to 2.6 mmol Al/kg, 0.75 mmol Al/kg to 2.2 mmol Al/kg, 0.9 mmol Al/kg to 1.8 mmol Al/kg, 1.1 mmol Al/kg to 1.8 mmol Al/kg, or 1.1 mmol Al/kg to 1.5 mmol Al/kg. Other aluminum concentration ranges that can be utilized are readily apparent to those skilled in the art with the aid of this disclosure. As utilized herein the phrase "aluminum of the organoaluminum compound concentration" refers to the aluminum concentration within a solution, stream, or vessel (e.g., reaction zone) that is attributable to the aluminum of the organoaluminum compound.

In any aspect and/or embodiment, the oligomer product can be formed at, the reaction zone can have, or the reaction zone can operate at, a minimum ethylene partial pressure of 750 psi (5.17 MPa), 775 psi (5.34 kPa), or 800 psi (5.52 kPa); alternatively or additionally, a maximum ethylene partial pressure of 1,200 psi (8.27 MPa), 1,100 psi (7.58 MPa), or 1000 psi (6.89 MPa). In an embodiment, the oligomer product can be formed at, the reaction zone can have, or the reaction zone can operate at, an ethylene partial pressure in the range of any minimum ethylene partial pressure disclosed herein to any maximum ethylene partial pressure disclosed herein. In some non-limiting embodiments, the oligomer product can be formed at, the reaction zone can have, or the reaction zone can operate at, an ethylene partial pressure in the range of 750 psi (5.17 MPa) to 1,200 psi (8.27 MPa), from 775 psi (5.34 kPa) to 1,100 psi (7.58 MPa), or from 800 psi (5.52 kPa) to 1000 psi (6.89 MPa). Other ethylene partial pressure ranges are readily apparent to those skilled in the art with the aid of this disclosure.

In any aspect and/or embodiment, the oligomer product can be formed at, the reaction zone can have, or the reaction zone can operate at, a minimum ethylene:organic reaction medium mass ratio of 0.8:1, 1:1, 1.25:1, or 1.5:1; alternatively, or additionally, a maximum ethylene:organic reaction medium mass ratio of 4.5:1, 4:1, 3.5:1, 3:1, or 2.5:1. In an embodiment, the oligomer product can be formed at, the reaction zone can have, or the reaction zone can operate at, an ethylene:organic reaction medium mass ratio in the range of any minimum ethylene:organic reaction medium mass ratio disclosed herein to any maximum ethylene:organic reaction medium mass ratio disclosed herein. In some non-limiting embodiments, the oligomer product can be formed at, the reaction zone can have, or the reaction zone can operate at, an ethylene:organic reaction medium mass ratio in the range of 0.8:1 to 4.5:1, 1:1 to 4:1, 1:1 to 3.5:1, 1.25:1 to 3:1, or 1.5:1 to 2.5:1. Other ethylene:organic reaction medium mass ratio ranges that can be utilized are readily apparent to those skilled in the art with the aid of this disclosure.

In any aspect and/or embodiment, the oligomer product can be formed at, the reaction zone can have, or the reaction zone can operate at, a minimum reaction zone temperature of 75° C., 77° C., or 80° C.; alternatively or additionally, a maximum reaction zone reaction zone temperature 95° C., 93° C., or 90° C. In an embodiment, the oligomer product can be formed at, the reaction zone can have, or the reaction zone can operate at, a reaction zone temperature in the range of any minimum temperature disclosed herein to any maximum temperature disclosed herein. In a non-limiting embodiment, the oligomer product can be formed at, the reaction zone can have, or the reaction zone can operate at, a reaction zone temperature in the range of 75° C. to 95° C., 77° C. to 93° C., or 80° C. to 90° C. Other temperature ranges that can be utilized are readily apparent to those skilled in the art with the aid of this disclosure. In embodiments where the temperature can vary within the reaction zone, the temperature provided herein can alternatively be an average temperature.

In any aspect and/or embodiment, the oligomer product can have a minimum Schulz-Flory K value of (or can be at least) 0.4, 0.45, 0.5; or, 0.55; alternatively or additionally, a maximum Schulz-Flory K value of 0.9, 0.85, 0.8, 0.75, 0.7 or, 0.65. In an embodiment, the oligomer product can have a Schulz-Flory K value in the range of any minimum Schulz-Flory K value disclosed herein to any maximum Schulz-Flory K value disclosed herein. For example, in some non-limiting embodiments, the oligomer product can have a Schulz-Flory K value in the range from 0.4 to 0.9; alternatively, from 0.4 to 0.8; alternatively, from 0.5 to 0.8; alternatively, from 0.5 to 0.7; alternatively, from 0.55 to 0.7. Other oligomer product Schulz-Flory K value ranges are readily apparent from the present disclosure.

In any aspect and/or embodiment, the Schulz-Flory K value can be determined using any one or more of the $C_8$, $C_{10}$, $C_{12}$, $C_{14}$, or $C_{16}$ oligomer products. In an embodiment, the Schulz-Flory K value can be an average of any two or more Schulz-Flory K values using different adjacent pairs of produced oligomers described herein. In some embodiments, the Schulz-Flory K value can be an average of any two Schulz-Flory K values described herein; alternatively, any three Schulz-Flory K values described herein; or alternatively, any four Schulz-Flory K values described herein. For example, the Schulz-Flory K value can be determined using the $C_8$ and $C_{10}$ oligomer product; alternatively, the $C_{10}$ and $C_{12}$ oligomer product; alternatively, the $C_{12}$ and $C_{14}$ oligomer product; alternatively, the $C_{14}$ and $C_{16}$ oligomer product; alternatively, the $C_8$, Cm, and $C_{12}$ oligomer product.

In any aspect and/or embodiment wherein hydrogen is utilized, the oligomer product can be formed (or the reaction zone can operate) at a minimum hydrogen partial pressure of 1 psi (6.9 kPa), 2 psi (14 kPa); 5 psi (34 kPa), 10 psi (69 kPa), or 15 psi (103 kPa); alternatively or additionally a maximum hydrogen partial pressure of 200 psi (1.4 MPa), 150 psi (1.03 MPa), 100 psi (689 kPa), 75 psig (517 kPa), or 50 psi (345 kPa). In an embodiment, the oligomer product can be formed (or the reaction zone can operate) at a hydrogen partial pressure in the range of any minimum hydrogen partial pressure disclosed herein to any maximum hydrogen partial pressure disclosed herein. In some non-limiting embodiments wherein hydrogen is utilized, the oligomer product can be formed (or the reaction zone can operate) at a hydrogen partial pressure from 1 psi (6.9 kPa) to 200 psi (1.4 MPa), from 5 psi (34 kPa) to 150 psi (1.03 MPa), from 10 psi (69 kPa) to 100 psi (689 kPa), or from 15 psi (100 kPa) to 75 psig (517 kPa). Other hydrogen partial pressure ranges that can be utilized are readily apparent to those skilled in the art with the aid of this disclosure.

In any aspect and/or embodiment wherein hydrogen is utilized, the oligomer product can be formed (or the reaction zone can operate) at a minimum hydrogen to ethylene mass ratio of (0.05 g hydrogen)/(kg ethylene), (0.1 g hydrogen)/(kg ethylene), (0.25 g hydrogen)/(kg ethylene), (0.4 g hydrogen)/(kg ethylene), or (0.5 g hydrogen)/(kg ethylene); alternatively or additionally, at a maximum hydrogen to ethylene mass ratio can be (5 g hydrogen)/(kg ethylene), (3 g hydrogen)/(kg ethylene), (2.5 g hydrogen)/(kg ethylene), (2 g hydrogen)/(kg ethylene), or (1.5 g hydrogen)/(kg ethylene). In an embodiment, the oligomer product can be formed (or the reaction zone can operate) at a hydrogen to ethylene mass ratio in the range of any minimum hydrogen to ethylene mass ratio disclosed herein to any maximum hydrogen to ethylene mass ratio disclosed herein. In some non-limiting embodiments, the oligomer product can be formed (or the reaction zone can operate) at a hydrogen to ethylene mass ratio from (0.05 g hydrogen)/(kg ethylene) to (5 g hydrogen)/(kg ethylene), from (0.25 g hydrogen)/(kg ethylene) to (5 g hydrogen)/(kg ethylene), from (0.25 g hydrogen)/(kg ethylene) to (4 g hydrogen)/(kg ethylene), from (0.4 g hydrogen)/(kg ethylene) to (3 g hydrogen)/(kg ethylene), from (0.4 g hydrogen)/(kg ethylene) to (2.5 g hydrogen)/(kg ethylene), from (0.4 g hydrogen)/(kg ethylene) to (2 g hydrogen)/(kg ethylene), or from (0.5 g hydrogen)/(kg ethylene) to (2 g hydrogen)/(kg ethylene). Other hydrogen to ethylene mass ratio ranges that can be utilized are readily apparent to those skilled in the art with the aid of this disclosure.

In any aspect and/or embodiment, the processes described herein can produce an oligomer product with high selectivity to linear alpha olefins; or alternatively, to normal alpha olefins. In some embodiments, the processes described herein can produce a reactor effluent wherein the $C_6$ olefin oligomer product has a 1-hexene content of at least 98.5 wt. %; alternatively, at least 98.75 wt. %; alternatively, at least 99.0 wt. %; or alternatively, at least 99.25 wt. %. In other embodiments, the processes described herein can produce a reactor effluent wherein the $C_8$ olefin oligomer product has a 1-octene content of at least 98 wt. %; alternatively, at least 98.25 wt. %; alternatively, at least 98.5 wt. %; alternatively, at least 98.75 wt. %; or alternatively, at least 99.0 wt. %. In yet other embodiments, the processes described herein can produce a reactor effluent wherein the $C_{10}$ olefin oligomer product has a 1-decene content of at least 97.5 wt. %; alternatively, at least 97.75 wt. %; alternatively, at least 98 wt. %; alternatively, at least 98.25 wt. %; or alternatively, at least 98.5 wt. %. In yet other embodiments, the processes described herein can produce a reactor effluent wherein the $C_{12}$ olefin oligomer product has a 1-dodecene content of at least 96.5 wt. %; alternatively, at least 97 wt. %; alternatively, at least 97.5 wt. %; alternatively, at least 97.75 wt. %; or alternatively, at least 98.0 wt. %. In yet other embodiments, the processes described herein can produce a reactor effluent wherein the oligomer product can comprise any combination of any $C_6$ olefin oligomer product 1-hexene content described herein, any $C_8$ olefin oligomer product 1-octene content described herein, any $C_{10}$ olefin oligomer product 1-decene content described herein, and/or any $C_8$ olefin oligomer product 1-octene content described herein. In some non-limiting examples, the processes described herein can produce a reactor effluent having a $C_6$ olefin oligomer product 1-hexene content of at least 99 wt. % and a $C_{12}$ olefin oligomer product 1-dodecene content of at least 97.5 wt. %; alternatively, a $C_8$ olefin oligomer product 1-octene content of at least 98.5 wt. % and a $C_{12}$ olefin oligomer product 1-dodecene octene content of at least 97.5 wt. %; or alternatively, a $C_6$ olefin oligomer product 1-hexene content of at least 99 wt. %, a $C_8$ olefin oligomer product 1-octene content of at least 98.5 wt. %, a $C_{10}$ olefin oligomer product 1-decene content of at least 98 wt. %, and a $C_{12}$ olefin oligomer product 1-dodecene content of at least 97.5 wt. %. Other combinations of reactor effluent olefin oligomer 1-alkene contents are readily apparent from the present disclosure.

Without being limited to theory, it is believed that various combination of conditions at which the oligomer product can be formed, the reaction zone can have, or the reaction zone can operate, can lead to reduced reaction zone fouling though high molecular weight oligomer and/or polymer adherence to the reaction zone surfaces. Polymer adherence to the reaction zone surfaces such as heat transfer surfaces can reduce the ability to control the temperature conditions at which the oligomer product can be formed, the reaction zone can have, or the reaction zone can operate. In an aspect, the processes described herein can operate where the reaction zone (comprising a reactor) is online for a time ranging from any minimum online time disclosed herein to any maximum online time disclosed herein. In an embodiment, the reaction zone minimum online time can be at least 100 hours, 150 hours, 200 hours 300 hours, 400 hours, 500 hours, or 600 hours. In an embodiment, the reaction zone maximum online time can be 9000 hours, 18000 hours, 27000 hours, 36000 hours, or 45,000 hours. In a non-limiting embodiment, the reaction zone online time can range from 100 hours to 45,000 hours, 150 hours to 36,000 hours, 200 hours to 36,000 hours, 300 hours to 36,000 hours, 300 hours to 27,000 hours, 400 hours to 27,000 hours, 400 hours to 18,000 hours, 500 hours to 27,000 hours, 500 hours to 18,000 hours, or 500 hours to 9,000 hours. Other reaction zone online time ranges are readily apparent to those skilled in the art with the aid of this disclosure.

Without being limited to theory it is believed that various combination of conditions at which the oligomer product can be formed, the reaction zone can have, or the reaction zone can operate, enable reduced reaction zone fouling though high molecular weight oligomer and/or polymer adherence to the reaction heat transfer surfaces (including reactor zone walls) by reducing polymer swelling that can lead to polymer adhering to reaction zone surfaces (e.g., heat transfer surfaces, among other surfaces). Without being limited there unto, it has been discovered that a particular combinations of reaction zone temperatures and organic reaction medium selections can reduce polymer swelling and lead to improved process reaction zone operability (e.g., reaction zone online time, among other potential reaction zone operability improvements). In such non-limiting embodiments, the processes disclosed herein can be operated such that the oligomer product can be formed at, the reaction zone can have, or the reaction zone can operate at, a temperature within any range of and including 75° C. to 95° C. disclosed herein and using an organic reaction medium reaction medium comprising, or consisting essentially of any $C_8$ to $C_{18}$ aliphatic hydrocarbon (e.g., saturated aliphatic hydrocarbon or olefinic aliphatic hydrocarbon) disclosed herein. In further embodiments, the processes can be operated such that the oligomer product can be formed at, the reaction zone can have, or the reaction zone can operate at, conditions that can comprise, either singly or in any combination, any iron of the iron salt concentration disclosed herein or iron of the pyridine bisimine iron salt complex concentration disclosed herein, any pyridine bisimine to iron salt equivalent ratio charged to the reaction zone disclosed herein, aluminum of the organoaluminum compound to the iron of the iron salt molar ratio disclosed herein or iron of the pyridine bisimine iron salt complex molar ratio disclosed herein, aluminum concentration disclosed herein, any ethylene partial pressure disclosed herein, any ethylene to organic reaction medium mass ratio disclosed herein, Schulz-Flory K value disclosed herein, any hydrogen partial pressure disclosed herein, or any hydrogen to ethylene mass ratio disclosed herein.

In an aspect, the processes described herein can produce a reactor effluent wherein the polymer component of the reaction zone effluent comprises a maximum of 15 wt. % solids, alternatively a maximum of 10 wt. % solids, alternatively a maximum of 8 wt. % solids. In an non-limiting alternative aspect, the processes described herein can produce a reaction zone effluent wherein the polymer component of the reaction zone effluent comprises from 5 wt. % to 15 wt. % solids, alternatively from 7 wt. % to 12 wt. % solids, or alternatively from 7 wt. % to 10 wt. % solids.

In an aspect, the processes described herein can produce a reactor zone effluent wherein the polymer component comprises greater than 90 wt. %, greater 92 wt. %, greater than 94 wt. %, greater than 96 wt. %, greater than 98 wt. %, or greater than 99 wt. % polymer having a molecular weight of less than 1000 g/mol.

In an aspect, the processes described herein can produce an oligomer product such that the less than 50 wt. %, 60 wt. % 70 wt. % or 75 wt. % of the oligomer product adhering to the reaction zone wall comprises polyethylene has a $M_w$ greater than 1000 g/mol.

Various aspect and/or embodiments described herein can refer to substituted groups or compound. In an embodiment, each substituent of any aspect or embodiment calling for a substituent can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. In an embodiment, each hydrocarbyl substituent can be a $C_1$ to $C_{10}$, or a $C_1$ to $C_5$ hydrocarbyl group. In an embodiment, each hydrocarboxy group or substituent of any aspect or embodiment calling for a group substituent can be a $C_1$ to $C_{10}$, or a $C_1$ to $C_5$ hydrocarboxy group. In an embodiment, any halide substituent of any aspect or embodiment calling for a substituent can be a fluoride, chloride, bromide, or iodide; alternatively, a fluoride or chloride. In some embodiments, any halide substituent of any aspect or embodiment calling for a substituent can be a fluoride; alternatively, a chloride; alternatively, a bromide; or alternatively, an iodide.

In an embodiment, any hydrocarbyl substituent of any aspect and/or embodiment calling for a substituent can be an alkyl group, an aryl group, or an aralkyl group; alternatively, an alkyl group; alternatively, an aryl group; or alternatively, an aralkyl group. In an embodiment, any alkyl substituent of any aspect and/or embodiment calling for a substituent can be a methyl group, an ethyl group, an n-propyl group, an isopropyl group, an n-butyl group, a sec-butyl group, an isobutyl group, a tert-butyl group, an n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group; alternatively, a methyl group, an ethyl group, an isopropyl group, a tert-butyl group, or a neo-pentyl group; alternatively, a methyl group; alternatively, an ethyl group; alternatively, an isopropyl group; alternatively, a tert-butyl group; or alternatively, a neopentyl group. In an embodiment, any aryl substituent of any aspect and/or embodiment calling for a substituent can be phenyl group, a tolyl group, a xylyl group, or a 2,4,6-trimethylphenyl group; alternatively, a phenyl group; alternatively, a tolyl group, alternatively, a xylyl group; or alternatively, a 2,4,6-trimethylphenyl group. In an embodiment, any aralkyl substituent of any aspect or embodiment calling for a substituent can be benzyl group or an ethylphenyl group (2-phenyleth-1-yl or 1-phenyleth-1-yl); alternatively, a benzyl group; alternatively, an ethylphenyl group; alternatively a 2-phenyleth-1-yl group; or alternatively, a 1-phenyleth-1-yl group.

In an embodiment, any hydrocarboxy substituent of any aspect and/or embodiment calling for a substituent can be an alkoxy group, an aryloxy group, or an aralkoxy group; alternatively, an alkoxy group; alternatively, an aryloxy group, or an aralkoxy group. In an embodiment, any alkoxy substituent of any aspect and/or embodiment calling for a substituent can be a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, or a neo-pentoxy group; alternatively, a methoxy group, an ethoxy group, an isopropoxy group, a tert-butoxy group, or a neo-pentoxy group; alternatively, a methoxy group; alternatively, an ethoxy group; alternatively, an isopropoxy group; alternatively, a tert-butoxy group; or alternatively, a neo-pentoxy group. In an embodiment, any aryloxy substituent of any aspect and/or embodiment calling for a substituent can be phenoxy group, a toloxy group, a xyloxy group, or a 2,4,6-trimethylphenoxy group; alternatively, a phenoxy group; alternatively, a toloxy group, alternatively, a xyloxy group; or alternatively, a 2,4,6-trimethylphenoxy group. In an embodiment, any aralkoxy substituent of any aspect or embodiment calling for a substituent can be benzoxy group.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed above and throughout the text are provided solely for their disclosure prior to the filing date of the present application. Nothing herein is to be construed as an admission that the inventors are not entitled to antedate such disclosure by virtue of prior invention.

In any application before the United States Patent and Trademark Office, the Abstract of this application is provided for the purpose of satisfying the requirements of 37 C.F.R. § 1.72 and the purpose stated in 37 C.F.R. § 1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that can be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

The present disclosure is further illustrated by the following examples, which are not to be construed in any way as imposing limitations upon the scope thereof. On the contrary, it is to be clearly understood that resort can be had to various other aspects, embodiments, modifications, and equivalents thereof which, after reading the description herein, can suggest themselves to one of ordinary skill in the art without departing from the spirit of the present invention or the scope of the appended claims.

The data and descriptions provided in the following examples are given to show particular aspects and embodiments of the compounds, catalyst systems, and olefin oligomerization and/or olefin polymerization methods disclosed, and to demonstrate a number of the practices and advantages thereof. The examples are given as a more detailed demonstration of some of the aspects and embodiments described herein and are not intended to limit the disclosure or claims in any manner.

Additional Disclosure

The following enumerated aspects of the present disclosures are provided as non-limiting examples.

A first aspect which is a process comprising: A) continuously introducing into a reaction zone i) ethylene, ii) a pyridine bisimine iron salt complex, iii) an organoaluminum compound, and iv) an organic reaction medium comprising, or consisting essentially of, one or more $C_8$ to $C_{18}$ aliphatic hydrocarbons; and B) forming an oligomer product in the reaction zone, the reaction zone having an average temperature in a range of 75° C. to 95° C.

A second aspect which is a process comprising: A) continuously introducing into a reaction zone i) ethylene, ii) an iron salt, iii) a pyridine bisimine, iii) an organoaluminum compound, and iv) an organic reaction medium comprising, or consisting essentially of one or more $C_8$ to $C_{18}$ aliphatic hydrocarbons; and B) forming an oligomer product in the reaction zone, the reaction zone having an average temperature in a range of 75° C. to 95° C.

A third aspect which is the process of the second aspect, wherein the reaction zone has an iron salt to pyridine bisimine equivalent ratio in a range of 0.8:1 to 1.2:1.

A fourth aspect which is a process of any one of the first through the third aspects, wherein the reaction zone has an iron of the pyridine bisimine iron salt complex concentration of $5 \times 10^{-4}$ mmol/kg to $5 \times 10^{-3}$ mmol/kg.

A fifth aspect which is the process of any one of the first through the fourth aspects, wherein the reaction zone has an aluminum of the organoaluminum compound to iron of the pyridine bisimine iron salt complex molar ratio in a range of 300:1 to 800:1.

A sixth aspect which is the process of the fifth aspect, wherein the reaction zone aluminium of the organoaluminum compound to iron of the iron salt or iron of the pyridine bisimine iron salt complex molar ratio in a range of 300:1 to 500:1.

A seventh aspect which is the process of any one of the first through the sixth aspects, wherein the reaction zone has an ethylene partial pressure in a range of 750:1 psig to 1200 psig.

An eighth aspect which is the process of the seventh aspect, wherein the reaction zone ethylene partial pressure is in a range of 750 to 1000 psi.

A ninth aspect which is the process of any one of the first through the eight aspects, wherein the reaction zone has an ethylene to organic reaction medium mass ratio of 0.8 to 4.5.

A tenth aspect which is the process of any one of the first through the ninth aspects, wherein the reaction zone has an aluminum of the organoaluminum compound concentration in a range of 0.75 mmol Al/kg to 2.6 mmol Al/kg.

An eleventh aspect which is the process of any one of the first through the tenth aspects, wherein hydrogen is continuously introduced into the reaction zone and the reaction zone has a hydrogen partial pressure of at least 5 psi.

A twelfth aspect which is a process comprising: A) continuously introducing into a reaction zone i) ethylene, ii) an pyridine bisimine iron salt complex, iii) an organoaluminum compound, and iv) an organic reaction medium; B) forming an oligomer product in the reaction zone, the reaction zone having i) an iron of the pyridine bisimine iron salt complex concentration in a range of $5 \times 10^{-4}$ mmol/kg to $5 \times 10^{-3}$ mmol/kg, ii) an aluminum of the organo aluminum compound to iron of the pyridine bisimine iron salt complex molar ratio in a range of 300:1 to 800:1, iii) an ethylene partial pressure in a range of 750:1 psig to 1200 psig, iv) an ethylene to organic reaction medium mass ratio of 0.8 to 4.5, and v) an average temperature in a range of 75° C. to 95° C.; and optionally vi) a hydrogen partial pressure of at least 5 psi.

A thirteenth aspect which is a process comprising: A) continuously introducing into a reaction zone i) ethylene, ii) an iron salt, iii) a pyridine bisimine, iv) an organoaluminum compound, and v) an organic reaction medium, and B) forming an oligomer product in the reaction zone, the reaction zone having i) an iron of the iron salt concentration in a range of $5 \times 10^{-4}$ mmol/kg to $5 \times 10^{-3}$ mmol/kg, ii) an aluminum of the organo aluminum compound to iron of the iron salt molar ratio in a range of 300:1 to 800:1, iii) an ethylene partial pressure in a range of 750 psig to 1200 psig, iv) an ethylene to organic reaction medium mass ratio in a range of 0.8 to 4.5, v) a temperature in a range of 75° C. to 95° C., and optionally vi) a hydrogen partial pressure of at least 5 psi.

A fourteenth aspect which is the process of the thirteenth aspect, wherein the reaction zone has an iron salt to pyridine bisimine equivalent ratio in the range of 0.8:1 to 1.2:1.

A fifteenth aspect which is the process of any one of the twelfth through the fourteenth aspects, wherein the reaction zone has an aluminum of the organoaluminum compound concentration in a range of 0.75 mmol Al/kg to 2.6 mmol Al/kg.

A sixteenth aspect which is the process of any one of the twelfth through the fifteenth aspects, wherein the reaction zone aluminium of the organoaluminum compound to iron of the iron salt or iron of the pyridine bisimine iron salt complex molar ratio in the range of 300:1 to 500:1.

A seventeenth aspect which is the process of any one of the twelfth through the sixteenth aspects, wherein the reaction zone ethylene partial pressure in the range of 750 to 1000 psi.

An eighteenth aspect which is the process of any one of the twelfth through the seventeenth aspects, wherein the reaction zone ethylene to organic reaction medium mass ratio in the range of 0.8:1 to 4.5:1.

A nineteenth aspect which is the process of any one of the twelfth through the eighteenth aspects, wherein the organic reaction medium comprises, or consists essentially of, one or more aliphatic hydrocarbons.

A twentieth aspect which is the process of the nineteenth aspects, wherein the organic reaction medium comprises, or consists essentially of, one or more $C_8$ to $C_{18}$ aliphatic hydrocarbons.

A twenty first aspect which is the process of any one of the first through the eleventh aspects or the nineteenth aspect, wherein the organic reaction medium comprises, or consists essentially of, one or more $C_8$ to $C_{16}$ saturated aliphatic hydrocarbons.

A twenty second aspect which is the process of any one of the first through the eleventh aspects or the nineteenth aspect, wherein the organic reaction medium comprises, or consists essentially of, one or more $C_8$ to $C_{16}$ olefinic aliphatic hydrocarbons.

A twenty third aspect which is the process of the twenty second aspect, wherein the organic reaction medium comprises, or consists essentially of, 1-decene, 1-dodecene, 1-tetradecene, or any combination thereof.

A twenty fourth aspect which is the process of any one of the first through the twenty third aspects, wherein the organic reaction medium is substantially devoid of a halogenated compound.

A twenty fifth aspect which is the process of any one of the first through the twenty fourth aspects, wherein the reaction zone has a temperature in the range of 80° C. to 90° C.

A twenty sixth aspect which is the process of any one of the first through the twenty fifth aspects, wherein the oligomer product formed in the reaction zone has a Schulz-Flory K value in the range of 0.4 to 0.9 (or in the range of 0.5 to 0.8).

A twenty seventh aspect which is the process of any one of the first through the twenty sixth aspects, wherein greater than 50 wt. % of the oligomer product adhering to the reaction zone wall comprises polyethylene having an $M_w$ greater than 1000 g/mol.

A twenty eighth aspect which is the process of any one of the first through the twenty seventh aspects, wherein the reaction zone is online for at least 100 hours.

A twenty ninth aspect which is the process of any one of the first through the twenty eighth aspects, further comprising continuously discharging a reaction zone effluent from the reaction zone.

A thirtieth aspect which is the process of any one of the first through the twenty ninth aspects, further comprising introducing the organic reaction medium to the reaction zone prior to introducing the iron salt pyridine bisimine complex, the iron salt, the pyridine bisimine compound, or the ethylene to the reaction zone.

A thirty first aspect which is the process of any one of the first through the thirtieth aspects, further comprising introducing 1) the pyridine bisimine iron salt complex, or 2) the iron salt, the pyridine bisimine to the reaction zone prior to introducing ethylene to the reaction zone.

A thirty second aspect which is the process of any one of the first through the thirty first aspects, wherein the pyridine bisimine or the pyridine bisimine of the pyridine bisimine iron salt complex comprises i) a 2,6-bis[(arylimine)hydrocarbyl]pyridine wherein the aryl groups can be the same or different, ii) a bis[(substituted arylimine)hydrocarbyl]pyridine, wherein the substituted aryl groups can be the same or different, or iii) a [(arylimine)hydrocarbyl], [(substituted arylimine)hydrocarbyl]pyridine.

A thirty third aspect which is the process of the thirty second aspects, wherein 1) one, two, or three of the aryl groups and/or substituted aryl groups positions ortho to the carbon atom attached to the imine nitrogen independently are a halogen, a primary carbon atom group, or a secondary carbon atom group and the remainder of the aryl groups and/or substituted aryl groups positions ortho to the carbon atom attached to the imine nitrogen are hydrogen, 2) one of the aryl groups and/or substituted aryl groups positions ortho to the carbon atom attached to the imine nitrogen is a tertiary carbon atom group, none, one, or two of the aryl groups and/or substituted aryl groups positions ortho to the carbon atom attached to the imine nitrogen independently are a halogen, a primary carbon atom group or a secondary carbon atom group, and the remainder of the aryl groups and/or substituted aryl groups positions ortho to the carbon atom attached to the imine nitrogen are hydrogen, 3) two of the aryl groups and/or substituted aryl groups positions ortho to the carbon atom attached to the imine nitrogen independently are a tertiary carbon atom group, none, or one of the aryl groups and/or substituted aryl groups positions ortho to the carbon atom attached to the imine nitrogen independently are a halogen, a primary carbon atom group, or a secondary carbon atom group, and the remainder of the aryl groups and/or substituted aryl groups positions ortho to the carbon atom attached to the imine nitrogen are hydrogen, 4) one or two of the aryl groups and/or substituted aryl groups positions ortho to the carbon atom attached to the imine nitrogen independently are a tertiary carbon atom group(s) and the remainder of the aryl groups and/or substituted aryl groups positions ortho to the carbon atom attached to the imine nitrogen are hydrogen, 5) one or two of the aryl groups and/or substituted aryl groups positions ortho to the carbon atom attached to the imine nitrogen are a quaternary carbon atom group and the remainder of the aryl groups and/or substituted aryl groups positions ortho to the carbon atom attached to the imine nitrogen are hydrogen, or 6) all four of the substituted aryl groups positions ortho to the carbon atom attached to the imine nitrogen are fluorine.

A thirty fourth aspect which is the process of the thirty second aspects, wherein the pyridine bisimine is selected from the group consisting of 2,6-bis[(phenylimine) methyl] pyridine, 2,6-bis[(2-methylphenylimine)methyl]pyridine, 2,6-bis[(2-ethylphenylimine)methyl]pyridine, 2,6-bis[(2-isopropylphenylimine)methyl]pyridine, 2,6-bis[(2,4-dimethylphenylimine)methyl]pyridine, 2-[(2,4,6-trimethylphenylimine)methyl]-6-[(3,5-dimethylphenylimine)methyl] pyridine, and 2-[(2,4,6-trimethylphenylimine)methyl]-6-[(4-t-butylphenylimine)methyl]pyridine.

A thirty-fifth aspect which is a process comprising A) continuously introducing into a reaction zone i) ethylene, ii) an iron salt, iii) a pyridine bisimine, iv) an organoaluminum compound, and v) an organic reaction medium comprising a $C_8$ to $C_{18}$ aliphatic hydrocarbon; and B) forming an oligomer product in the reaction zone, the reaction zone having an average temperature in a range of 75° C. to 95° C.

A thirty-sixth aspect which is a process comprising A) continuously introducing into a reaction zone i) ethylene, ii) an pyridine bisimine iron salt complex, iii) an organoaluminum compound, and iv) an organic reaction medium comprising one or more $C_8$ to $C_{18}$ aliphatic hydrocarbons; and B) forming an oligomer product in the reaction zone, the reaction zone having an average temperature in a range of 75° C. to 95° C.

EXAMPLES

All manipulations were carried out using a nitrogen filled Vacuum Atmospheres drybox and standard Schlenk techniques using oven dried glassware (>1 h at 110° C. under vacuum, −30 mmHg). Dichloromethane (DCM) was anhydrous grade from Fisher utilized in the drybox and stored over molecular sieves. Toluene was anhydrous grade from Sigma-Aldrich utilized in the drybox and stored over molecular sieves. Organic reaction mediums, cyclohexane and 1-dodecene, were obtained from Chevron Phillips Chemical Company, LP. The organic reaction mediums were then charged to a N2 degassed feed tanks (10 or 20 gal), further degassed with N2 and further purified using molecular sieves, activated alumina, and a reduced copper bed to remove water, oxygen/polar compounds, and dissolved oxygen. MMAO-3A (typically 6 to 8 wt. % aluminum) was obtained from AkzoNobel Chemicals Company and stored in a N2 filled drybox. Meta-xylene was obtained from Sigma-Aldrich, degassed under N2 and stored over molecular sieves in the drybox. The pyridine bisimine ligands (2-[(2,4,6-trimethylphenylimine)methyl]-6-[(4-butylphenylimine)methyl]pyridine, 2-[(2,4,6-trimethylphenyl-imine) methyl]-6-[(4-methylphenylimine)methyl]pyridine, and 2-[(2,4,6-trimethylphenylimine)methyl]-6-[(3,5-dimethylphenylimine)methyl]pyridine) and the pyridine bisimine iron complexes ([2-[(2,4,6-trimethylphenylimine)methyl]-6-[(4-butylphenylimine)methyl]pyridine]$FeCl_2$) were prepared according to known procedures.

Ethylene oligomerizations were performed using the reaction system illustrated in the FIGURE. The reaction system 200 had 1) a reaction zone comprising a 500 mL autoclave reactor 10 having a) an overhead magnetic stirrer 20, b) an oil filled external jacket heating system controlled an internal TI probe 30, c) separate feed lines for i) ethylene 45, ii) the pyridine bisimine and the iron salt, or the pyridine bisimine iron salt complex (PBFe) 55, and iii) an organoaluminum compound (OAC) 65 and organic reaction medium (ORM) 75, d) an autoclave reactor effluent outlet line 85 (including a not shown reactor effluent sample port) heat traced to maintain a skin temperature of 135° C., e) an organic reaction medium diluent feed tank 70, f) an organic reaction medium feed pump 80 to provide the organic reaction medium to the reaction zone though the an organoaluminum compound and organic reaction medium inlet, g) an ISCO pump 105 coupled to an organoaluminum compound charger 101 to feed the organoaluminum compound to the suction side of the organic reaction medium feed pump, h) an ISCO pump 115 coupled to a charger 112 to feed the pyridine bisimine and iron salt solution, or the pyridine bisimine iron salt complex solution to the reaction zone through the pyridine bisimine and iron salt feed line, i) a regulated (0 to 600 g/hour) ethylene feed 120 to provide ethylene through the reaction zone ethylene feed inlet, j) a heat traced product tank 130 (to maintain an approximate temperature of 90° C.) to accept reaction zone effluent from the reaction zone outlet line, k) a Badger research control valve 140 (with the ability to maintain pressure from a minimum of 200 psig to a maximum of 1200 psig) on the product maintain pressure on the product tank and reaction zone, and 1) a nitrogen feed line 150 to maintain a nitrogen atmosphere on the reaction zone and product tank.

In a drybox, a clean dry 250 mL glass charging flask was washed with desired solvent/diluent. The 250 mL glass charging flask was then drained and charged with the desired quantity of the desired pyridine bisimine, the desired quantity of the desired iron salt, and desired quantity of solvent/diluent (or the desired quantity of pyridine bisimine iron salt complex and the desired quantity of solvent/diluent). The 250 mL charging flask was then sealed and removed from the drybox. The contents of the 250 mL charging flask were then charged to the pyridine bisimine/iron salt solution (or pyridine bisimine iron salt complex solution) ISCO pump and the pyridine bisimine/iron salt solution (or pyridine bisimine iron salt complex solution) charge lines flushed with approximately 15 mL of the pyridine bisimine/iron salt solution (or pyridine bisimine iron salt complex solution).

In a drybox, a clean dry 250 mL glass charging flask was washed with desired solvent/diluent. The 250 mL glass charging flask was then drained and charged with the desired quantity of nonane (used as an internal standard) and desired amount of organoaluminum solution to achieve a 10:1 ratio, by volume, of nonane to the organoaluminum compound solution. The desired quantity of organoaluminum compound solution. The 250 mL charging flask was then sealed and removed from the drybox. The contents of the 250 mL charging flask were then charged to the organoaluminum ISCO pump and the organoaluminum charge lines were flushed with approximately 15 mL of the organoaluminum solution.

The 500 mL autoclave reactor was prepared for the ethylene oligomerization using three cycles of filling the autoclave reactor to 800 prig with dry nitrogen and then venting the autoclave reactor. The product tank was then filled with dry nitrogen and brought to the desired operating temperature. A quick connect transfer line was then used to connect the organic reaction medium feed tank to the autoclave reactor. The autoclave reactor was then filled with organic reaction medium using nitrogen pressure. The quick connect transfer line was then disconnected from the autoclave reactor. The organic reaction medium pump was then started and the autoclave reactor was brought to the desired oligomerization pressure. Once the oligomerization pressure was achieved, the overhead magnetic stirrer was switched on and stirring set at a rate of approximately 1200 rpm. The external heating was then initiated and the autoclave reactor was brought up to the desired oligomerization temperature. The ISCO pumps for the organoaluminum compound and the pyridine bisimine and iron salt solution (or the pyridine bisimine iron salt solution) were turned on and set to the desired feed rates. Thirty minutes after initiating the organoaluminum compound feed and the pyridine bisimine and iron salt solution (or the pyridine bisimine iron salt solution) feed, ethylene was introduced to the autoclave reactor at a rate of approximately 250 g/h. After one hour, the reaction zone effluent sample port was purged with reactor effluent for a few minutes, a reaction effluent sample was taken, analyzed by low thermal mass gas chromatography (LTM-GC), and an estimate of catalyst system productivity determined. If the ethylene conversion and catalyst system productivity was determined to be within an acceptable range, the ethylene flow rate was then increased to the desired flow rate by slowly increasing the ethylene flow rate at a rate of 100 g/hour. Reaction zone effluent samples were then taken every 30 minutes by purging the reaction zone sample port for a few minutes and then collecting a reaction zone effluent sample. The reaction zone effluent samples were then analyzed by LTM-GC using a 30 m Agilent DB1 column operating with a flame ionization detector or a Agilent 6890 gas chromatographs using 50 m HP5 or DB5 column operating with a flame ionization detector.

After completion of the oligomerization reaction, the pressure on the autoclave reactor was released and the liquids and solids from the reactor body and head were collected. The collected solids were dried, and weighed. The reactor solids were then reported as Rx Solids/kg NAO product.

The contents of the product tank were homogenized and then analyzed by taking a 250 g of the product tank contents. The homogenized sample was subject to rotary evaporation for one hour at 100° C. and −30 in Hg to effectively remove the liquid. The mass of the remaining solids (wax and polyethylene) was recorded and a portion of the solids was analyzed by thermogravimetric analysis (TGA). The quantity of the types of materials in the solids sample was determined using the TGA temperature ranges of A) liquids—<175° C., B) waxes—175° C. to 420° C., and C) polyethylene (PE) >420° C. The amount of polyethylene produced is then reported as % $C_2H_4$ to polyethylene.

Examples 1-14

Ethylene oligomerizations utilizing three different catalyst systems were performed using the ethylene oligomerization procedure. Catalyst system 1 comprised ([2-[(2,4,6-trimethylphenylimine)methyl]-6-[(4-butylphenylimine) methyl]pyridine]$FeCl_2$) and MMAO-3A.

Catalyst system 2 comprised 2-[(2,4,6-trimethylphenylimine)methyl]-6-[(3,5-dimethylphenylimine)-methyl] pyridine), iron(III) acetylacetonate (hereafter Fe(acac)$_3$), and MMAO-3A. Catalyst system 3 comprised 2-[(2,4,6-trimethylphenylimine)methyl]-6-[(4-methylphenylimine) methyl]pyridine, iron(III) acetylacetonate (hereafter Fe(acac)$_3$), and MMAO-3A. Table 1 provides information regarding the preparation of the iron compound and MMAO-3A solution utilized for the catalyst system in the ethylene oligomerizations. Table 2 provides information regarding ethylene oligomerization run conditions. Table 3 provides information regarding the performance of the ethylene oligomerization.

TABLE 1

Ethylene Oligomerization Catalyst System Solution Data

| | | | | Catalyst System Component Solution Concentrations | | |
|---|---|---|---|---|---|---|
| Exam. | Catalyst System | Iron Compound Solvent | Catalyst Solvent Ratio | Iron Compound Concentration, mg/mL | Ligand Concentration, mg/mL | MMAO-3A Concentration mg/mL |
| 1 | 1 | Dichloromethane | — | 0.25 | — | 72.3 |
| 2 | 1 | Dichloromethane | — | 0.25 | — | 72.3 |
| 3 | 2 | Toluene | — | 0.047 | 0.078 | 72.3 |
| 4 | 2 | Toluene | — | 0.047 | 0.078 | 72.3 |
| 5 | 2 | m-xylene/ Cyclohexane | 103:47 | 0.047 | 0.078 | 72.3 |
| 6 | 2 | m-xylene/ Cyclohexane | 103:47 | 0.047 | 0.078 | 72.3 |
| 7 | 2 | m-xylene/ Cyclohexane | 103:47 | 0.047 | 0.078 | 72.3 |
| 8 | 2 | m-xylene/ Cyclohexane | 103:47 | 0.047 | 0.078 | 72.3 |
| 9 | 2 | Toluene/ Cyclohexane | 103:47 | 0.047 | 0.078 | 72.3 |
| 10 | 2 | Toluene | — | 0.047 | 0.078 | 72.3 |
| 11 | 2 | m-xylene/ Cyclohexane | 103:47 | 0.047 | 0.078 | 72.3 |
| 12 | 2 | m-xylene/ Cyclohexane | 103:47 | 0.047 | 0.078 | 72.3 |
| 13 | 2 | m-xylene/ Cyclohexane | 103:47 | 0.047 | 0.078 | 72.3 |
| 14 | 3 | m-xylene/ Cyclohexane | 103:47 | 0.047 | 0.078 | 72.3 |

TABLE 2

Ethylene Oligomerization Run Parameters

| | | | | Feed Rates | | | | | |
|---|---|---|---|---|---|---|---|---|---|
| Example | Organic Reaction Medium | Reactor Pressure, psig | Reactor Temperature, °C. | Organic Reaction, g/hour | Iron Compound Solution, mL/h | MMAO-3A Solution, mL/h | Ethylene, g/hour | Reactor Fe concentration, ppm by mass | Reactor Al concentration, ppm by mass |
| 1 | cyclohexane | 1000 | 100 | 350 | 3 | 5.4 | 300 | 0.1 | 34 |
| 2 | 1-dodecene | 1000 | 100 | 450 | 3 | 7 | 425 | 0.1 | 33 |
| 3 | 1-dodecene | 1000 | 100 | 500 | 9.4 | 7 | 400 | 0.1 | 32 |
| 4 | 1-dodecene | 1000 | 110 | 450 | 9.4 | 7 | 425 | 0.1 | 31 |
| 5 | cyclohexane | 1000 | 70 | 400 | 9.4 | 7 | 500 | 0.2 | 34 |
| 6 | cyclohexane | 1000 | 80 | 350 | 9.4 | 7 | 500 | 0.1 | 39 |
| 7 | cyclohexane | 1000 | 100 | 350 | 9.4 | 7 | 300 | 0.2 | 48 |
| 8 | 1-dodecene | 1000 | 80 | 350 | 9.4 | 7 | 500 | 0.1 | 36 |
| 9 | 1-dodecene | 1000 | 90 | 450 | 9.4 | 7 | 450 | 0.1 | 33 |
| 10 | 1-dodecene | 1000 | 100 | 450 | 9.4 | 7 | 550 | 0.1 | 26 |
| 11 | 1-dodecene | 1000 | 90 | 350 | 9.4 | 7 | 500 | 0.1 | 36 |
| 12 | 1-dodecene | 1000 | 90 | 250 | 9.4 | 7 | 500 | 0.1 | 37 |
| 13 | 1-dodecene | 1000 | 85 | 200 | 9.4 | 7 | 500 | 0.1 | 40 |
| 14 | 1-dodecene | 1000 | 85 | 200 | 9.4 | 7 | 500 | 0.1 | 41 |

TABLE 3

Ethylene Oligomerization Performance

| Example | $C_2H_4$ conversion, wt. % | K value, ($C_{12}/C_{10}$) | Peak Productivities kg product/g iron compound | Peak Productivities kg product/g Al | Rx Solids, g/kg prod. | Product Tank Solids, wt. % wax/wt. % PE | $C_2H_4$ to PE, wt. % | Reactor Discharge Solids, g solids/kg Product | STY, Lb/gal/hour | Carbon Number Purity $C_6$, wt. % | $C_8$, wt. % | $C_{14}$, wt. % | $C_{16}$, wt. % |
|---|---|---|---|---|---|---|---|---|---|---|---|---|---|
| 1 | 50.3 | 0.65 | 231 | 7.0 | 0.81 | — | — | — | 2.9 | — | — | 96.1 | 95.7 |
| 2 | 67.2 | 0.60 | 381 | 8.9 | 3.03 | — | — | — | 4.8 | — | — | 88.3 | 84.8 |
| 3 | 75.6 | 0.62 | 370 | 10.3 | 4.89 | — | — | — | 5.2 | — | — | 83.6 | 82.8 |
| 4 | 31.8 | 0.64 | 237 | 6.6 | 1.31 | — | — | — | 3.5 | — | — | 91.1 | 87.0 |
| 5 | 34.0 | 0.76 | 95 | 5.3 | 3.32 | 10.6/0.5 | 1.0 | 2238 | 1.7 | — | — | 96.5 | 95.0 |
| 6 | 48.1 | 0.69 | 209 | 5.8 | 1.86 | 6.3/0.2 | 0.9 | 12.0 | 3.1 | — | — | 97.6 | 97.2 |
| 7 | 56.5 | 0.68 | 157 | 4.4 | — | 2.8/0.26 | 0.7 | 11.4 | 2.3 | — | — | 97.5 | 97.1 |
| 8 | 74.2 | 0.69 | 473 | 13.2 | 3.78 | 15.1/0.40 | 0.9 | 26.0 | 7.1 | 99.1 | 98.1 | 93.0 | 91.2 |
| 9 | 72.2 | 0.65 | 412 | 11.5 | 3.81 | 1.9/0.15 | 0.5 | 29.8 | 6.2 | 98.9 | 97.8 | 91.1 | 89.0 |
| 10 | 70.7 | 0.55 | 387 | 10.8 | 10.8 | — | — | — | 5.8 | 98.5 | 98.5 | 92.5 | 87.6 |
| 11 | 65.3 | 0.64 | 447 | 12.4 | 0.87 | 10.1/0.54 | 1.1 | 19.7 | 6.7 | 99.3 | 98.4 | 93.5 | 91.0 |
| 12 | 79.9 | 0.66 | 451 | 12.5 | 6.21 | 15.2/0.94 | 2.4 | 38.1 | 6.7 | 98.3 | 96.7 | 89.5 | 85.2 |
| 13 | 77.5 | 0.67 | 430 | 12.0 | 8.58 | 8.6/0.48 | 0.9 | 18.0 | 6.4 | 99.2 | 98.4 | 94.3 | 93.6 |
| 14 | 78.8 | 0.66 | 439 | 12.2 | 1.72 | 17.3/1.41 | 1.9 | 32.2 | 6.6 | 98.8 | 97.5 | 94.2 | 93.6 |

Discussion of Ethylene Oligomerization Results

Ethylene oligomerizations Examples 1 and 2 were performed in cyclohexane and 1-dodecene, respectively, utilizing ([2-[(2,4,6-trimethylphenylimine)methyl]-6-[(4-butylphenylimine)methyl]-pyridine]$FeCl_2$). Since ([2-[(2,4,6-trimethylphenylimine)methyl]-6-[(4-butylphenylimine)methyl]-pyridine]$FeCl_2$) was not soluble in hydrocarbon solvent, dichloromethane was utilized as the solvent for ([2-[(2,4,6-trimethylphenylimine)methyl]-6-[(4-butylphenylimine)methyl]pyridine]$FeCl_2$). To test whether the metal complex could be prepared in-situ, and to determine whether the ethylene oligomerization could be performed in the absence of halogenated hydrocarbons, Examples 3 and 4 were performed in cyclohexane and 1-dodecene, respectively, by preparing a solution of 2-[(2,4,6-trimethylphenylimine)methyl]-6-[(3,5-dimethylphenylimine)methyl] pyridine) and Fe(acac)$_3$) in toluene. These examples show that ethylene oligomerization can be performed with catalyst systems using a pyridine bisimine iron complex or an in-situ prepared pyridine bisimine iron complex and that both methods provide ethylene oligomerization catalysts having comparable productivities. Comparison of Examples 1 and 2 shows that ethylene oligomerization using 1-dodecene as an organic reaction medium provided increased productivities but decreased 1-alkene purity in the $C_{14}$ and $C_{16}$ product fractions. Additionally, the use of 1-dodecene reduced downstream fouling and aided in polymer handling.

Ethylene oligomerization Examples 5-7 and Examples 8-10 were performed using cyclohexane and 1-dodecene, respectively, as the organic reaction medium to determine the effect of temperature and organic reaction medium on catalyst system productivities, polymer production, and product quality. Additionally, these Examples included a visual observation of the autoclave reactor body and autoclave head to provide a qualitative determination of the amount and type of polymer which collected in the autoclave reactor during the ethylene oligomerization. These qualitative results are tabulated in Table 4.

TABLE 4

| Example | Temp/ Organic Reaction Medium | Quantity | Type |
|---|---|---|---|
| 5 | 70° C./ cyclohexane | Heavy accumulation on reactor body wall, reactor head surfaces, and stirrer | Waxy and stringy with some strips wrapped around stirrer |
| 6 | 80° C./ cyclohexane | Moderate accumulation on reactor body wall, reactor head surfaces, and stirrer | Waxy and stringy with some strips wrapped around stirrer |
| 7 | 100° C./ cyclohexane | Light accumulation on reactor body surface and reactor head surface. Moderate stringy accumulation on stirrer | Stringy and wrapped around stirrer |
| 8 | 80° C./ 1-dodecene | Light dusting on reactor body wall, reactor head surfaces. Small amount of accumulation on stirrer | Waxy/Dusty/Film |
| 9 | 90° C./ 1-dodecene | Thin film on reactor body wall, reactor head surfaces. Small amount of accumulation on stirrer | Waxy/Dusty/Film |
| 10 | 100° C./ 1-dodecene | Light film on reactor body wall, reactor head surfaces. Moderate accumulation on reactor head surfaces, and stirrer | Waxy and slightly stringy |

Productivity data for the ethylene oligomerization in cyclohexane indicate that there appears to be a sweet spot for productivity around an ethylene oligomerization temperature of 80° C. The cyclohexane ethylene oligomerization data also indicates that increasing the ethylene oligomerization temperature can decrease product tank solids and that low ethylene oligomerization temperatures can negatively impact olefin quality via a reduction in carbon number alkene purity. Qualitative observations of the solids remaining in the autoclave reactor indicate that increasing the ethylene oligomerization with cyclohexane as the organic reaction medium can decrease the amount of solid retained in the ethylene oligomerization reactor.

Productivity data for the ethylene oligomerization in 1-dodecene indicate that increasing ethylene oligomerization data can cause a slight reduction in productivity and can decrease product tank solids. The 1-dodecene ethylene oligomerization data also indicates that increasing the ethylene oligomerization temperature can negatively impact olefin quality via a reduction in carbon number alkene purity. Qualitative observations of the solids remaining in the autoclave reactor indicate that increasing the ethylene oligomerization with 1-dodecene as the organic reaction medium can increase the amount of solids retained in the ethylene oligomerization reactor.

Comparing the qualitative observations of the solids remaining in the autoclave reactor between the cyclohexane ethylene oligomerizations and the 1-dodecene ethylene oligomerization runs, it appears using a higher carbon numbered hydrocarbon organic reaction medium can reduce the amount of solid remaining in the reactor. Additionally, it appears that the use of a higher carbon numbered hydrocarbon organic reaction medium can change the type of solid remaining in the reactor. In particular, it appears that using a higher carbon numbered organic reaction medium can change the type of reactor solids from a waxy stringy solid than can quickly foul reactor operations to a dusty filmy solid which can be more easily flushed from the reactor during normal operation.

Examples 8-14 provide information regarding the impact that temperature, organic reaction medium (1-dodecene) to ethylene flow ratio can have on an ethylene oligomerization. The experiments show that 1) temperature does not have a large impact on the K-vale at temperature of approximately 85° C. to 90° C., 2) space time yield can be maintained a high level at a temperature of approximately 85° C. to 90° C., and/or 3) increasing the organic reaction medium (1-dodecene) to ethylene flow rate can negatively impact the linear 1-alkene content of the $C_{14}$ and $C_{16}$ carbon number fractions.

Examples 13 and 14 show that the catalyst systems using the 2-[(2,4,6-trimethylphenylimine)methyl]-6-[(4-methylphenylimine)methyl]pyridine ligand and the 2-[(2,4,6-trimethylphenylimine)methyl]-6-[(3,5-dimethylphenylimine)methyl]pyridine) ligand provide ethylene oligomerization that 1) can have similar productivities, 2) can provide similar quantities of reactor and/or total product solids, and/or 3) can produce an oligomer product that can have a similar linear 1-alkene content for the $C_{14}$ and $C_{16}$ carbon number fractions.

What is claimed is:
1. A process comprising:
  A) continuously introducing into a reaction zone
    i) ethylene,
    ii) either
      a) a pyridine bisimine iron salt complex, or
      b) an iron salt and a pyridine bisimine,
      where the iron salt or the iron salt of the pyridine bisimine iron salt complex has the formula $FeX_n$, where X is a halide, a $C_1$ to $C_{20}$ carboxylate, or a C to $C_{20}$ β-diketonate and n is 2 or 3, and
      the pyridine bisimine or the pyridine bisimine of the pyridine bisimine iron salt complex comprises i) a 2,6-bis[(arylimine)hydrocarbyl]pyridine wherein the aryl groups can be the same or different, ii) a bis[(substituted arylimine)hydrocarbyl]pyridine, wherein the substituted aryl groups can be the same or different, or iii) a [(arylimine)hydrocarbyl], [(substituted arylimine)hydrocarbyl]pyridine,
    iii) an organoaluminum compound comprising an aluminoxane, and
    iv) an organic reaction medium comprising one or more $C_8$ to $C_{18}$ aliphatic hydrocarbons; and
  B) forming an oligomer product in the reaction zone, the reaction zone having an average temperature in a range of 75° C. to 95° C.,
    wherein greater than 50 wt. % of the oligomer product adhering to a wall of the reaction zone comprises polyethylene having an $M_w$ greater than 1000 g/mol.
2. The process of claim 1, wherein the reaction zone has an iron salt to pyridine bisimine equivalent ratio in the range of 0.8:1 to 1.2:1.
3. The process of claim 1, wherein the reaction zone has an iron of the pyridine bisimine iron salt complex, or iron of the iron salt, concentration of $5\times10^{-4}$ mmol/kg to $5\times10^{-3}$ mmol/kg, an aluminium of the organoaluminum compound to iron of the iron salt or iron of the pyridine bisimine iron salt complex molar ratio in a range of 300:1 to 800:1, an ethylene partial pressure in a range of 750:1 psig to 1200 psig, an ethylene to organic reaction medium mass ratio of 0.8:1 to 4.5:1, an aluminum of the organoaluminum compound concentration in a range of 0.75 mmol Al/kg to 2.6 mmol Al/kg, or any combination thereof.
4. The process of claim 1, wherein hydrogen is continuously introduced into the reaction zone and the reaction zone has a hydrogen partial pressure of at least 5 psi.

5. The process of claim 1, wherein the organic reaction medium comprises one or more $C_8$ to $C_{16}$ olefinic aliphatic hydrocarbons.

6. The process of claim 3, wherein the reaction zone has an aluminum of the organoaluminum compound concentration in a range of 0.75 mmol Al/kg to 2.6 mmol Al/kg, the aluminum of the organoaluminum compound to iron of the iron salt molar ratio is in the range of 300:1 to 500:1, the ethylene partial pressure is in the range of 750 to 1000 psi, and the temperature is in the range of 80° C. to 90° C.; wherein the oligomer product formed in the reaction zone has a Schulz-Flory K value in a range of 0.4 to 0.9 and wherein the organic reaction medium consists essentially of one or more of $C_8$ to $C_{16}$ olefinic aliphatic hydrocarbons.

7. The process of claim 1, wherein
1) one, two, or three of the aryl groups and/or substituted aryl groups positions ortho to the carbon atom attached to the imine nitrogen independently are a halogen a primary carbon atom group or a secondary carbon atom group; and the remainder of the aryl groups and/or substituted aryl groups positions ortho to the carbon atom attached to the imine nitrogen are hydrogen,
2) one of the aryl groups and/or substituted aryl groups positions ortho to the carbon atom attached to the imine nitrogen is a tertiary carbon atom group; none, one, or two of the aryl groups and/or substituted aryl groups positions ortho to the carbon atom attached to the imine nitrogen independently are a halogen, a primary carbon atom group or a secondary carbon atom group; and the remainder of the aryl groups and/or substituted aryl groups positions ortho to the carbon atom attached to the imine nitrogen are hydrogen,
3) two of the aryl groups and/or substituted aryl groups positions ortho to the carbon atom attached to the imine nitrogen independently are a tertiary carbon atom group; none, or one of the aryl groups and/or substituted aryl groups positions ortho to the carbon atom attached to the imine nitrogen independently are a halogen, a primary carbon atom group, or a secondary carbon atom group; and the remainder of the aryl groups and/or substituted aryl groups positions ortho to the carbon atom attached to the imine nitrogen are hydrogen,
4) one or two of the aryl groups and/or substituted aryl groups positions ortho to the carbon atom attached to the imine nitrogen independently are a tertiary carbon atom group(s); and the remainder of the aryl groups and/or substituted aryl groups positions ortho to the carbon atom attached to the imine nitrogen are hydrogen,
5) one or two of the aryl groups and/or substituted aryl groups positions ortho to the carbon atom attached to the imine nitrogen are a quaternary carbon atom group; and
the remainder of the aryl groups and/or substituted aryl groups positions ortho to the carbon atom attached to the imine nitrogen are hydrogen, or
6) all four of the substituted aryl groups positions ortho to the carbon atom attached to the imine nitrogen are fluorine.

8. The process of claim 1, wherein the pyridine bisimine or the pyridine bisimine of the pyridine bisimine iron salt complex is selected from the group consisting of 2,6-bis[(phenylimine) methyl]pyridine, 2,6-bis[(2-methylphenylimine)methyl]pyridine, 2,6-bis[(2-ethylphenylimine)methyl]pyridine, 2, 6-bis[(2-isopropylphenylimine)methyl] pyridine, 2,6-bis[(2,4-dimethylphenylimine)methyl]pyridine, 2-[(2,4,6-trimethylphenylimine)methyl]-6-[(4-methylphenylimine)methyl]pyridine, 2-[(2,4,6-trimethylphenylimine)methyl]-6-[(3,5-dimethylphenylimine)methyl]pyridine, and 2-[(2,4,6-trimethylphenylimine)methyl]-6-[(4-t-butylphenylimine)methyl]pyridine, and combinations thereof.

9. The process of claim 1, further comprising introducing the organic reaction medium to the reaction zone prior to introducing 1) the iron salt pyridine bisimine complex or the iron salt and the pyridine bisimine compound, or 2) the ethylene to the reaction zone.

10. The process of claim 1, further comprising introducing 1) the pyridine bisimine iron salt complex, or 2) the iron salt and the pyridine bisimine to the reaction zone prior to introducing ethylene to the reaction zone.

11. The process of claim 1, wherein the organic reaction medium comprises 1-decene, 1-dodecene, 1-tetradecene, or any combination thereof.

12. The process of claim 1, wherein the organic reaction medium contains less than 1 wt. % halogenated compounds based on the weight of the organic reaction medium.

13. A process comprising:
A) continuously introducing into a reaction zone;
 i) ethylene,
 ii) an iron salt having the formula $FeX_n$ where X is a halide, a $C_1$ to $C_{20}$ carboxylate, or a $C_1$ to $C_{20}$ β-diketonate and n is 2 or 3,
 iii) a pyridine bisimine having a structure selected from:

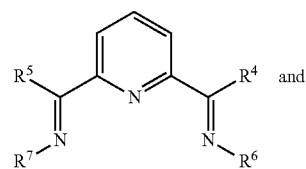

Structure PBI III and

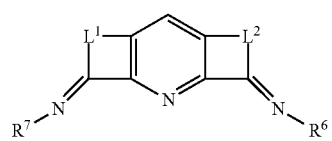

Structure PBI IV wherein $R^1$, $R^2$, and/or $R^3$ independently can be hydrogen, an inert functional group, or an organyl group; $R^4$ and/or $R^5$, independently can be hydrogen or an organyl group; $R^6$ and/or $R^7$ independently can be an aryl group, a substituted aryl group, a phenyl group, or a substituted phenyl group; and $L^1$ and/or $L^2$ independently can be an organylene group,
 iv) an organoaluminum compound comprising an aluminoxane, an alkylaluminum compound, or a combination thereof, and
 v) an organic reaction medium comprising one or more $C_8$ to $C_{18}$ aliphatic hydrocarbons; and
B) forming an oligomer product in the reaction zone, the reaction zone having:
 i) an iron of the iron salt concentration in a range of $5 \times 10^{-4}$ mmol/kg to $5 \times 10^{-3}$ mmol/kg,
 ii) an aluminum of the organoaluminum compound to iron of the iron salt molar ratio in a range of 300:1 to 800:1, ii) an ethylene partial pressure in a range of 750 psi to 1200 psi,
iv) an ethylene to organic reaction medium mass ratio in a range of 0.8 to 4.5,
v) an average temperature in a range of 75° C. to 95° C., and optionally
vi) a hydrogen partial pressure of at least 5 psi,
wherein greater than 50 wt. % of the oligomer product adhering to a wall of the reaction zone comprises polyethylene having an $M_W$ greater than 1000 g/mol..

14. The process of claim 13, wherein the organic reaction medium comprises one or more $C_8$ to $C_{16}$ olefinic aliphatic hydrocarbons.

15. The process of claim 13, wherein the organic reaction medium comprises 1-decene, 1-dodecene, 1-tetradecene, or any combination thereof.

16. The process of claim 13, wherein the pyridine bisimine comprises i) a 2,6-bis[(arylimine)hydrocarbyl]pyridine, wherein the aryl groups can be the same or different, ii) a bis[(substituted arylimine)hydrocarbyl]pyridine, wherein the substituted aryl groups can be the same or different, or iii) a [(arylimine)hydrocarbyl], [(substituted arylimine)hydrocarbyl]pyridine.

17. A process comprising:
A) continuously introducing into a reaction zone;
i) ethylene,
ii) a pyridine bisimine iron salt complex, wherein the pyridine bisimine iron salt complex has a structure selected from:

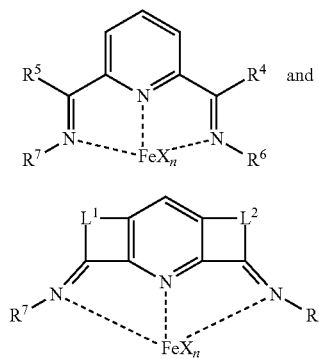

Structure PBIFe III and
Structure PBIFe IV wherein $R^1$, $R^2$, and/or $R^3$ independently can be hydrogen, an inert functional group, or an organyl group; $R^4$ and/or $R^5$, independently can be hydrogen or an organyl group; $R^6$ and/or $R^7$ independently can be an aryl group, a substituted aryl group, a phenyl group, or a substituted phenyl group; $L^1$ and/or $L^2$ independently can be an organylene group; and X where X is a halide, a $C_1$ to $C_{20}$ carboxylate, or a $C_1$ to $C_{20}$ β-diketonate and n is 2 or 3,
iii) an organoaluminum compound comprising an aluminoxane, an alkylaluminum compound, or a combination thereof and
iv) an organic reaction medium comprising one or more $C_8$ to $C_{18}$ aliphatic hydrocarbons; and
B) forming an oligomer product in the reaction zone, the reaction zone having:
i) an iron of the pyridine bisimine iron salt complex concentration in a range of $5 \times 10^{-4}$ mmol/kg to $5 \times 10^{-3}$ mmol/kg,
ii) an aluminum of the organoaluminum compound to iron of the iron salt molar ratio in a range of 300:1 to 800:1,
ii) an ethylene partial pressure in a range of 750 psi to 1200 psi,
iv) an ethylene to organic reaction medium mass ratio in a range of 0.8 to 4.5,
v) an average temperature in a range of 75° C. to 95° C., and optionally
vi) a hydrogen partial pressure of at least 5 psi,
wherein greater than 50 wt. % of the oligomer product adhering to a wall of the reaction zone comprises polyethylene having an $M_w$ greater than 1000 g/mol.

18. The process of claim 17, wherein the organic reaction medium comprises one or more $C_8$ to $C_{16}$ olefinic aliphatic hydrocarbons.

19. The process of claim 17, wherein the organic reaction medium comprises 1-decene, 1-dodecene, 1-tetradecene, or any combination thereof.

20. The process of claim 17, wherein the pyridine bisimine of the pyridine bisimine iron salt complex comprises i) a 2,6-bis[(arylimine)hydrocarbyl]pyridine, wherein the aryl groups can be the same or different, ii) a bis[(substituted arylimine)hydrocarbyl]pyridine, wherein the substituted aryl groups can be the same or different, or iii) a [(arylimine)hydrocarbyl], [(substituted arylimine)hydrocarbyl]pyridine.

21. The process of claim 1, wherein the pyridine bisimine or the pyridine bisimine of the pyridine bisimine iron salt complex comprises i) a 2,6-bis[(arylimine)hydrocarbyl]pyridine, wherein the aryl groups can be the same or different, ii) a bis[(substituted arylimine)hydrocarbyl]pyridine, wherein the substituted aryl groups can be the same or different, or iii) a [(arylimine)hydrocarbyl], [(substituted arylimine)hydrocarbyl]pyridine.

22. The process of claim 13, wherein the reaction zone has an iron salt to pyridine bisimine equivalent ratio in the range of 0.8:1 to 1.2:1.

23. The process of claim 17, wherein the reaction zone has an iron salt to pyridine bisimine equivalent ratio in the range of 0.8:1 to 1.2:1.

* * * * *